US012227522B2

(12) United States Patent
Williams et al.

(10) Patent No.: US 12,227,522 B2
(45) Date of Patent: Feb. 18, 2025

(54) SYNTHESIS OF STRUCTURAL ANALOGS OF LARGAZOLE AND ASSOCIATED COMPOUNDS

(71) Applicants: COLORADO STATE UNIVERSITY RESEARCH FOUNDATION, Fort Collins, CO (US); CETYA THERAPEUTICS, INC., Fort Collins, CO (US)

(72) Inventors: Robert M. Williams, Ft. Collins, CO (US); Sivanagireddy Koti, Ft. Collins, CO (US); Subhadip De, Ft. Collins, CO (US); Anil M. Shelke, Ft. Collins, CO (US); Ryan E. Cerbone, Ft. Collins, CO (US); Nobuyoshi Yasuda, Ft. Collins, CO (US)

(73) Assignees: COLORADO STATE UNIVERSITY RESEARCH FOUNDATION, Fort Collins, CO (US); CETYA THERAPEUTICS, INC., Fort Collins, CO (US)

( * ) Notice: Subject to any disclaimer, the term of this patent is extended or adjusted under 35 U.S.C. 154(b) by 0 days.

(21) Appl. No.: 18/255,969

(22) PCT Filed: Dec. 16, 2021

(86) PCT No.: PCT/US2021/063719
§ 371 (c)(1),
(2) Date: Jun. 5, 2023

(87) PCT Pub. No.: WO2022/140144
PCT Pub. Date: Jun. 30, 2022

(65) Prior Publication Data
US 2024/0059709 A1   Feb. 22, 2024

Related U.S. Application Data

(60) Provisional application No. 63/128,273, filed on Dec. 21, 2020.

(51) Int. Cl.
*C07D 513/18*   (2006.01)

(52) U.S. Cl.
CPC ................... *C07D 513/18* (2013.01)

(58) Field of Classification Search
CPC ..................................... C07D 513/18
See application file for complete search history.

(56) References Cited

U.S. PATENT DOCUMENTS

| | | | |
|---|---|---|---|
| 4,456,592 A | 6/1984 | Okumura et al. |
| 5,846,933 A | 12/1998 | Korngold et al. |
| 6,509,315 B1 | 1/2003 | Joullie et al. |
| 8,217,076 B2 | 7/2012 | Williams et al. |
| 8,513,290 B2 | 8/2013 | Williams et al. |
| 9,186,402 B2 | 11/2015 | Williams et al. |
| 10,538,534 B2 | 1/2020 | Williams et al. |
| 10,676,504 B2 | 6/2020 | Williams et al. |
| 2005/0119169 A1 | 6/2005 | Deslongchamps et al. |
| 2007/0129289 A1 | 6/2007 | Joullie et al. |
| 2012/0264794 A1 | 10/2012 | Williams et al. |
| 2014/0080802 A1 | 3/2014 | Holson et al. |
| 2014/0093449 A1 | 4/2014 | Williams et al. |
| 2014/0243501 A1 | 8/2014 | Jiang et al. |
| 2015/0010541 A1 | 1/2015 | Liu et al. |
| 2018/0044376 A1 | 2/2018 | Williams et al. |

FOREIGN PATENT DOCUMENTS

| | | |
|---|---|---|
| JP | 03-141296 A | 6/1991 |
| JP | 2003-505417 A | 2/2003 |
| JP | 2009-507065 A | 2/2009 |
| JP | 2013-528182 A | 7/2013 |
| JP | 2013-532132 A | 8/2013 |
| JP | 2014-523857 A | 9/2014 |
| WO | WO 2007/061939 A2 | 5/2007 |
| WO | WO 2007/100385 A2 | 9/2007 |
| WO | WO 2009/032352 A1 | 3/2009 |
| WO | WO 2009/126315 A2 | 10/2009 |
| WO | WO 2010/009334 A1 | 1/2010 |
| WO | WO 2011/146918 A2 | 11/2011 |
| WO | WO 2015/183897 A1 | 12/2015 |
| WO | WO 2016/144665 A1 | 9/2016 |
| WO | WO 2016/144814 A1 | 9/2016 |
| WO | WO 2022/140144 A1 | 6/2022 |

OTHER PUBLICATIONS

International Preliminary Report on Patentability, dated Jun. 13, 2023, corresponding to International Application No. PCT/US2021/063719, (from which the present application claims priority,) 8 pp.
International Search Report and Written Opinion, dated May 5, 2022, corresponding to International Application No. PCT/US2021/063719, (from which the present application claims priority,) 16 pp.
Pubchem-SID:53837011 Deposit Date: Oct. 6, 2008 {Oct. 6, 2008) pp. 1-5; p. 2. (4 pages).
Ren et al. (2008) "Total Synthesis of Largazole," Synlett., vol. 15. pp. 2379-2383; DOI: 10.1055/s-2008-1078270. (5 pages).
Ying (2010) "Total Syntheses and Biological Studies of Largazole and Brasilibactin A., II. Stereoselective Synthesis of 2,6-Cis- and 2,6-Trans-Piperidines through an Organocatalytic Aza-Michael Reaction," Dissertation submitted in partial fulfillment of the requirements for the degree of Doctor of Philosophy in the Department of Chemistry in the Graduate School of Duke University. pp. 34-35, scheme 2.17 p. 35; pp. 65-67 scheme—p. 66. (6 pages total).
"Can child leukemia be prevented?", https://www.cancer.org/cancer/leukemia-in-children/causes-risks-prevention/prevention.html, last revised Feb. 3, 2016, accessed Oct. 25, 2018 (Year: 2016).

(Continued)

*Primary Examiner* — Brenda L Coleman
(74) *Attorney, Agent, or Firm* — Leydig, Voit & Mayer, Ltd.

(57) ABSTRACT

Disclosed are various synthetic methods to prepare structural analogs of largazole and derivatives thereof. One structural analog is an amide isostere of largazole. Another structural analog replaces the thiazole ring of largazole with a pyridine moiety or an oxazole moiety. Also disclosed are various intermediate compounds obtained when preparing structural analogs of largazole and derivatives thereof, including macrocycle analogs having an alcohol functionality.

14 Claims, 10 Drawing Sheets

(56) References Cited

OTHER PUBLICATIONS

Avenoza et al. (2001) "Enantioselective synthesis of (S)- and (R)-methylserines: application to the synthesis of (S)- and (R)-N-Boc-N,O-isopropylidene-amethylserinals," Tetrahedron: Asymmetry 12(6):949-957.
Berge et al. (1977) "Pharmaceutical salts," J. Pharm. Sci. 66: 1-19.
Bolden et al. (2006) "Anticancer activities of histone deacetylase inhibitors," Nat. Rev. Drug Discovery 5:769-784.
Bowers et al. (2008) "Total Synthesis and Biological Mode of Action of Largazole: A Potent Class I Histone Deacetylase Inhibitor," J Am Chem Soc 130:11219-22.
Bowers et al. (Feb. 2009) "Synthesis and Histone Deacetylase Inhibitory Activity of Largazole Analogs: Alteration of the Zinc-Binding Domain and Macrocyclic Scaffold," Org. Letters 11(6) 1301-1304.
Bowers et al. (Mar. 2009) "Synthesis and Conformation-Activity Relationships of the Peptide Isosteres of FK228 and Largazole," J. Am. Chem. Soc. 131, 2900-2905.
Bradner (2010) "Chemical Phylogenetics of Histone Deacetylases," Nat. Chem Biol. 6(3):238-243.
Burger's Medicinal Chemistry and Drug Discovery (1995, Manfred E. Wolff ed., 5th ed. 172-178, 929-932).
Chen et al. (2003) "Total Synthesis of the Depsipeptide FR-901375," J Org Chem 68:8902-8905.
Chen et al. (2018) "Process Development and Scale-up Total Synthesis of Largazole, a Potent Class I Histone Deacetylase Inhibitor," Org. Process, Res. & Dev., 22, 190-199.
Clausen et al. (2015) "Modular Synthesis and Biological Activity of Pyridyl-based Analogs of the Potent Class 1 Histone Deacetylase Inhibitor Largazole," Bioorg. & Med. Chem. 23:5061-5074.
Cleve, Trip Report for 9th Tetrahedron Symposium, Berkeley, CA Klos, Jul. 22-25, 2008, "Discovery and Optimization of Diamine Analogues as Potent Inhibitors of Leukotriene A4 Hydrolase."
Freireich et al. (1966) "Quantitative comparison to toxicity of anticancer agents in mouse, rat, hamster, dog, monkey and man," Cancer Chemother Rep 50:219.
Furumai et al. (2001) "Potent Histone Deacetylase Inhibitors Built From Trichostatin A and Cyclic Tetrapeptide Antibiotics Including Trapoxin," PNAS USA 98:87-92.
Ghosh et al. (2008) "Enantioselective Total Synthesis of (+)-Largazole, a Potent Inhibitor of Histone Deacetylase," Org. Lett. 10:3907-3909.
Greshock et al. (2008) "Improved Total Synthesis of the Potent HDAC Inhibitor FK228 (FR-901228)," Org Lett 10:613-616.
Grozinger et al. (1999) "Three proteins define a class of human histone deacetylases related to yeast Hda1 p," Proc. Nat. Acad. Sci. USA 96:4868-4873.
Guerra-Bubb et al. (2013) "Synthesis and HDAC inhibitory activity of isosteric thiazoline-oxazole largazole analogs," Bioorganic & Medicinal Chemistry Letters, 23(21), pp. 6025-6028.
Han et al. (2014) "Spiroacetal Formation through Telescoped Cycloaddition and Carbon-Hydrogen Bond Functionalization: Total Synthesis of Bistramide A," Angew. Chem. Int. Ed. 53, 11075-11078.
Handbook of Pharmaceutical Salts. Properties, Selection, and Use (P. Heinrich Stahl and C. Wermuth, Eds., Verlag Helvetica Chica Acta, Zurich, Switzerland (2002)).
Hong et al. (2012) "Largazole: From discovery to broad-spectrum therapy," Natural Products Reports, 29, 449-56.
Jeanguenat et al. (1991) "Stereoselective chain elongation at C-3 of cysteine through 2,3-dihydrothiazoles, without racemization. Preparation of 2-amino-5-hydroxv-3-mercaptoalkanoic acid derivatives," J Chem Soc, Perkins Trans 1:2291-2298.
Johnstone (2002) "Histone deacetylase inhibitors: novel drugs for the treatment of cancer," Nature Rev. Drug Disc. 1:287-299.
Katsura et al. (1994) "Studies on antiulcer drugs. 7. 2-Guanidino-4-pyridylthiazoles as histamine H2-receptor antagonists with potent gastroprotective effects against nonsteroidal antiinflammatory drug-induced injury," J Med Chem 37(1):57-66.

Lange et al. (1999) "A new mild method for the synthesis of amidines," Tetrahedron Lett. 40:7067-7070.
Li et al. (1996) "Total Synthesis of the Antitumor depsipeptide FR-901, 228," J Am Chem Soc 118:7237-7238.
Liu et al. (2010) "Anticolon Cancer Activity of Largazole, a Marine-Derived Tunable Histone Deacetylase Inhibitor," Journal of Pharmacology and Experimental Therapeutics, 335, 351-361.
Marsault et al. (2006) "Discovery of a New Class of Macrocyclic Antagonists to the Human Motilin Receptor," Journal of Medicinal Chemistry pp. C-D.
Masuoka et al. (2001) "Spiruchostatins A and B, novel gene expression-enhancing substances produced by Pseudomonas sp.," Tetrahedron Lett. 42:41-44.
Miller et al. (2003) "Histone deacetylase inhibitors," J. Med. Chem. 46:5097-5116.
Minucci et al. (2006) "Histone deacetylase inhibitors and the promise of epigenetic (and more) treatments for cancer," Nature Rev. Cancer 6:38-51.
Moradei et al. (2005) "Histone deacetylase inhibitors: latest developments, trends and prospects," Curr. Med. Chem. Anti-Cancer Agents 5:529-560.
Mulqueen et al. (1993) "Synthesis of the thiazoline-based siderophore (S)-desferrithiocin," Tetrahedron 49:5359-5364.
Nasveschuk et al. (2008) "A Concise Total Synthesis of Largazole, Solution Structure, and Some Preliminary Structure Activity Relationships," Org. Lett. 10:3595-3598.
Nishino et al. (2003) "Cyclic tetrapeptides bearing a sulfhydryl group potently inhibit histone deacetylases," Org Lett 5:5079-5082.
Patani et al. (1996) "Bioisosterism: A Rational Approach in Drug Design," Chem. Rev. 96:3147-3176.
Phillips et al. (2000) "Synthesis of Functionalized Oxazolines and Oxazoles with DAST and Deoxo-Fluor," Org Lett 2(8): 1165-1168.
Pilon et al. (2015) "Comparative pharmacokinetic properties and antitumor activity of the marine HDACi Largazole and Largazole peptide isostere," Cancer Chemother Pharmacol. 75(4): 671-682.
Quintas-Cardama et al. (2011) "Histone deacetylase inhibitors for the treatment of myelodysplastic syndrome and acute myeloid leukemia," Leukemia, 25, 226-35.
Reiner et al. (2002) "Non-covalent thrombin inhibitors featuring p3-heterocycles with PI-monocyclic arginine surrogates," Bioorg Med Chem Lett 12(8):1203-1208.
Salvador et al. (2014) "Modulation of Activity Profiles for Largazole-Based HDAC Inhibitors through Alteration of Prodrug Properties," ACS Medicinal Chemistry Letters, 5, 905-10.
Scientific Tables, Geigy Pharmaceuticals, Ardley, N.Y., (1970) 537.
Seiser et al. (2008) "Synthesis and Biological Activity of Largazole and Derivatives," Angew. Chem. Int. Ed. 47:6483-6485.
Shigematsu et al. (1994) "A novel antitumor bicycle depsipeptide produced by Chromobacterium violaceum No. 968," J. Antibiot. 47:311-314.
Smith et al. (2003) "Enantioselective synthesis of alphamethyl-D-cysteine and lanthionine building blocks via alpha-methyl-D-serine-beta-lactone," Org. Lett. 5:1035-1037.
Somech et al. (2004) "Histone deacetylase inhibitors—a new tool to treat cancer," Cancer Treat. Rev. 30:461.
Souto et al. (2010) "Synthesis and Biological Characterization of the Histone Deacetylase Inhibitor Largazole and C7-Modified Analogues," Journal of Medicinal Chemistry, 53, 4654-67.
Sun et al. (2018) "Radical-Mediated Thiol-Ene Strategy: Photoactivation of Thiol Containing Drugs in Cancer Cells," Angew. Chem. Int. Ed. 57, 15832-15835.
Taori et al. (2008) "Structure and Activity of Largazole, a Potent Antiproliferative Agent from the Floridian Marine Cyanobacterium Symploca sp.," J. Am. Chem. Soc. 130:1806-1807 and 13506.
Taunton et al. (1996) "A Mammalian Histone Deacetylase Related to the Yeast Transcriptional Regulator Rpd3p," Science 272:408-411.
Townsend et al. (2007) "The bicyclic depsipeptide family of histone deacetylase inhibitors," in Chemical Biology; Schreiber, S.L., et al. Eds.Wiley-VCR Verlag GmbH & Co. 693-720.

(56) References Cited

OTHER PUBLICATIONS

Ueda et al. (1994) "Action of FR901228, a Novel Antitumor Bicyclic Depsipeptide Produced by Chromobacterium violaceum No. 968, on Ha-ras Transformed NIH3T3 Cells," Biosci. Biotech. Biochem., 58 (9), 1579-1583.
Ueda et al. (1994) "FR901228, a novel antitumor bicyclic depsipeptide produced by Chromobacterium violaceum No. 968 III. Antitumor activities on experimental tumors in mice," J. Antibiot. 47:315-323.
Ueda et al. (1994) "FR901228, a novel antitumor bicyclic depsipeptide produced by Chromobacterium violaceum No. 968. I. Taxonomy, fermentation, isolation, physico-chemical and biological properties, and antitumor activity," J. Antibiot. 47:301-310.
Vanommeslaeghe et al. (Jul. 2005) "DFT-based Ranking of Zink-chelating Groups in Histone Deacetylase Inhibitors," Bioorg. Med. Chem. 13:6070-6082.
Vanommeslaeghe et al. (May 2005) "Theoretical study revealing the functioning of a novel combination of catalytic motives in Histone Deacetylase," Bioorg. Med. Chem. 13:3987-3992.
Videnov et al. (1996) "Synthesis of Naturally Occurring, Conformationally Restricted Oxazole and Thiazole Containing Di- and Tripeptide Mimetics," Angew Chem Int Ed Eng 35:1503-1506.
Ying et al. (Aug. 2008) "Synthesis and Activity of Largazole Analogues with Linker and Macrocycle Modification," Organic Letters 10(18):4021-4024.
Ying et al. (May 2008) "Total Synthesis and Molecular Target of Largazole, a Histone Deacetylase Inhibitor," J. Am. Chem. Soc. 130:8455-8459.
Yoshida et al. (Oct. 1990) "Potent and specific inhibition of mammalian histone deacetylase both in vivo and in vitro by trichostatin A," J. Biol. Chem. 265:17174.
Yoshida et al. (Sep. 1990) "Structural Specificity for Biological Activity of Trichostatin A, A Specific Inhibitor of Mammalian Cell Cycle with Potent Differentiation-Inducing Activity in Friend Leukemia Cells," J. Antibiot. 43: 1101-1106.
Yurek-George (2007) "The First Biologically Active Synthetic Analogues of FK228, the Depsipeptide Histone Deacetylase Inhibitor," J. Med. Chem. 50:5720-5726.
Yurek-George et al. (2004) "Total synthesis of spiruchostatin A, a potent histone deacetylase inhibitor," J Am Chem Soc 126: 1030-1031.
Zawilska et al. (2013) "Prodrugs: A challenge for the drug development," Pharmacological Reports, 65, 1-14.
Zhang et al. (Nov. 2019—Available online Sep. 4, 2019) "A fluorine scan on the Zn2+-binding thiolate side chain of HDAC inhibitor largazole: Synthesis, biological evaluation, and molecular modeling," Eur. J. Med. Chem., 182, 111672.
Zhao et al. (2017) "Synthesis and Biochemical Evaluation of Biotinylated Conjugates of Largazole Analogues: Selective Class I Histone Deacetylase Inhibitors," Israel Journal of Chemistry, 57, 319-330.
Akoto et al. (May 2019) "Concise Seven-Membered Oxepene/Oxepane Synthesis—Structural Motifs in Natural and Synthetic Products," Synthesis 51, 3529-3535.
Awakura (2000) "Synthetic Studies on Pectenotoxins: Synthesis of the Common C8-C18 THF Fragment," Synlett, 12, 1733-1736.
Cao et al. (2011) "Caspase-3 controlled assembly of nanoparticles for fluorescence turn on," Chemical Communications, 47(37), 10320-10322.
Caron et al. (2010) "Versatile Strategy to Access Tricycles Related to Quassinoids and Triterpenes," Org. Lett., 12, 508-511.
Crimmins et al. (2000) "Titanium Enolates of Thiazolidinethione Chiral Auxiliaries: Versatile Tools for Asymmetric Aldol Additions," Org. Lett. 2, 775-777.
Crimmins et al. (2001) "Asymmetric Aldol Additions: Use of Titanium Tetrachloride and (−)-Sparteine for the Soft Enolization of N-Acyl Oxazolidinones, Oxazolidinethiones, and Thiazolidinethiones," J. Org. Chem. 66, 894-902.
Pellissier (2018) "Recent developments in the asymmetric Reformatsky-type reaction," Beilstein J. Org. Chem., 14, 325-344.
Pierry (2011) "Synthesis of fluorinated pseudopeptides: metal mediated reversal of stereochemistry in diastereoselective addition of organometallic reagents to N-(tert-butanesulfinyl)-a-fluoroenimines," Org. Biomol. Chem., 9, 2378.
Tungen et al. (2015) "Stereoselective synthesis of maresin 1," Tetrahedron Lett. 56, 1843-1846.
U.S. Appl. No. 15/555,792, filed Sep. 5, 2017.
Borgini et al. (2020) "Synthesis and Antiproliferative Activity of Nitric Oxide-Donor Largazole Prodrugs," ACS Med. Chem. Lett. 11(5): 846-851.
Bowers et al. (Feb. 2009) "Synthesis and Conformation—Activity Relationships of the Peptide Isosteres of FK228 and Largazole," J. Am. Chem. Soc. 131: 2900-2905.
European Search Report (Partial) issued in EP 21911912.0 on Nov. 6, 2024.
Kim et al. (2017) "Synthesis and biological evaluation of largazole zinc-binding group analogs", Bioorganic & Medicinal Chemistry 25(12): 3077-3086.

Scheme 1

Scheme 2

Scheme 3

Scheme 4

Scheme 5

Scheme 6

Scheme 7

Scheme 8

Scheme 9

Scheme 10

Scheme 11

Scheme 12

Scheme 13

Scheme 14

Scheme 15

Scheme 16

Scheme 17

SYNTHESIS OF STRUCTURAL ANALOGS OF LARGAZOLE AND ASSOCIATED COMPOUNDS

CROSS-REFERENCE TO RELATED APPLICATIONS

This patent application is a U.S. National Stage Application filed under 35 U.S.C. § 371 of International Application No. PCT/US2021/063719, filed Dec. 16, 2021, which claims the benefit of U.S. Provisional Patent Application No. 63/128,273, filed Dec. 21, 2020, which is incorporated herein by reference in its entirety for all purposes.

STATEMENT REGARDING FEDERALLY SPONSORED RESEARCH OR DEVELOPMENT

This invention was made with Government support under Grant Number 2R42HL136068-02 awarded by the National Institutes of Health through the National Heart, Lung, and Blood Institute. The Government has certain rights in this invention.

BACKGROUND OF INVENTION

Histone deacetylase (HDAC) inhibitors show great promise in the treatment of numerous forms of cancer and other conditions (see, e.g., Williams et al., WO 2016/144814, hereby incorporated by reference in its entirety). Various classes of HDAC inhibitors are known and generally fall into five categories: hydroxamates, benzamides, short-chain fatty acids, trifluoromethyloxadiazoles, and macrocycles. Specific examples of naturally occurring HDAC inhibitors include SAHA, trichostatin A, apicidin, trapoxin, azumamide, FK228, largazole, FR901375, and spiruchostatins. However, intense research efforts have focused on preparing structural analogs of these natural products in an attempt to understand the relationship between inhibitor structure and HDAC inhibition, to find more potent inhibitors, and to prepare inhibitors that have desired structural properties.

Particular interest has focused on the macrocycle largazole, as well as structural analogs thereof, including its amide isostere, in which the ester within the peptide ring is replaced with an amide functionality (see, e.g., Bowers et al., *J. Am. Chem. Soc.* 2009, 131, 2900-2905, and Pilon et al., *Cancer Chemother Pharmacol.* 2015, 75(4): 671-682, both of which are hereby incorporated herein by reference in their entireties). Largazole has been isolated as a natural product from the marine cyano-bacterium *Symploca* sp., and the total synthesis of largazole has been successfully completed by several research groups (see Ying et al., *J. Am. Chem. Soc.* 2008, 130, 8455-59, hereby incorporated by reference in its entirety). Largazole has several disadvantages in some circumstances, particularly its susceptibility to hydrolysis owing to its ester functionality within the macrocyclic ring, as well as conformational flexibility. The amide isostere of largazole addresses these disadvantages by being more stable to hydrolysis and having a more rigid structure, which affords increased HDAC binding, both of which are the result of replacing the ester functionality of largazole with an amide group.

Interest has also been focused on structural analogs of largazole, including those which retain the ester functionality in the macrocycle, but which vary other structural positions in the molecule. For example, in one structural analog of largazole, the thiazole ring in largazole can be replaced with a pyridine moiety or an oxazole moiety.

The known synthetic routes to the amide isosteres of largazole and other structural analogs thereof suffer from several drawbacks, including low yields, milligram scale production, complexity of synthesis, and high cost (see, e.g., Bowers et al.). Such known routes also pass through a macrocycle containing a reactive thiol group, such as the compound of formula (III), where $R^1$ is SH, which are highly biologically active, unstable, and difficult to handle. Therefore, there is a need for improved synthetic methods for the preparation of HDAC inhibitors, including improved methods for preparing structural analogs of largazole and derivatives thereof, as well as the chemical compounds prepared via these improved methods. The invention described herein is directed to these, as well as other, important needs.

SUMMARY

Some benefits of the invention described herein include, employing synthetic methods that make use of macrocycles containing an alcohol functionality shown in formula (I), rather than a macrocycle having a thiol functionality. A macrocycle having an alcohol functionality is more stable, biologically inactive (see Table 1), and easier to handle (e.g., can be prepared in a crystalline form, see FIG. 10 XRD) than a comparable macrocycle with a thiol functionality. Other benefits of the methods disclosed herein include higher yields, more consistent yields, gram-scale production, easier and less complex synthesis, using less expensive materials, and reduced toxicity of intermediate compounds.

Disclosed is a method for preparing a compound of formula (I):

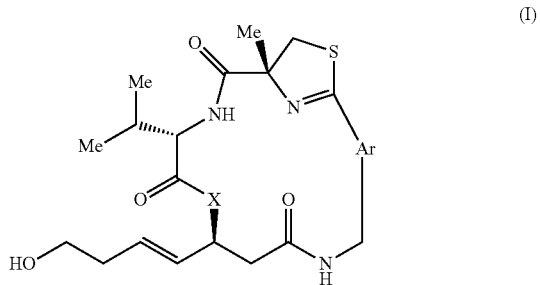

the method comprising reacting in one or more reactions: a compound of formula (IV), a compound of formula (V), and a compound of formula (VI), wherein the structures and variables are defined elsewhere herein.

Also disclosed is a method for preparing a compound of formula (III):

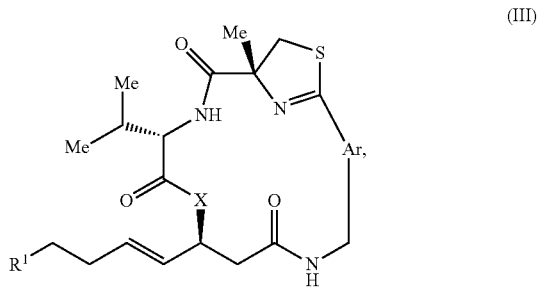

the method comprising reacting a compound of formula (I):

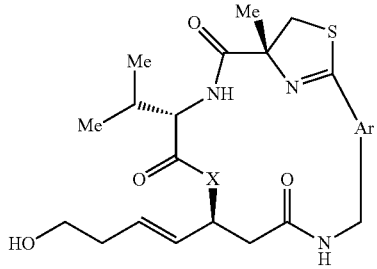
(I)

with an activating agent, thereby forming a compound of formula (II):

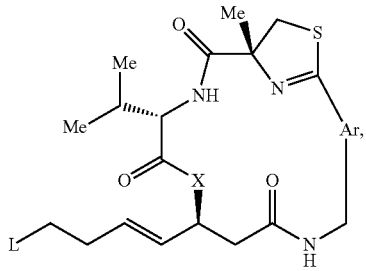
(II)

and reacting the compound of formula (II) with a nucleophile, thereby forming the compound of formula (III), wherein the structures, variables, activating agents, and nucleophile are as described elsewhere herein.

In some aspects, the compound of formula (I) is a compound of formula (I-a), (I-b), or (I-c):

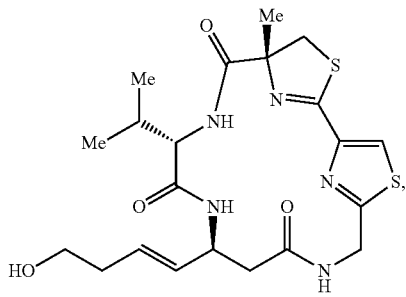
(I-a)

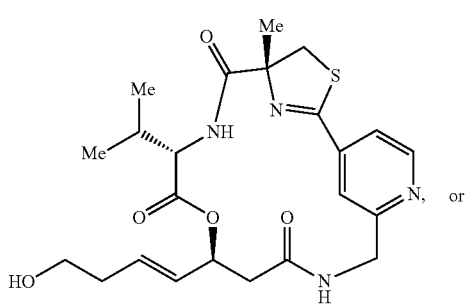
(I-b)

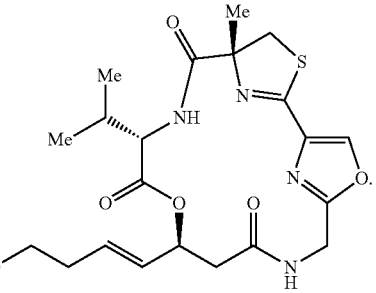
(I-c)

Additionally disclosed is a method for preparing a compound of formula (III):

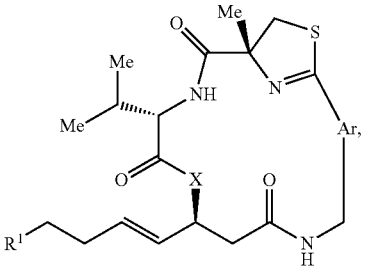
(III)

the method comprising reacting a compound of formula (II) with a nucleophile, wherein the structures, variables, activating agents, and nucleophile are as described elsewhere herein.

Also disclosed is a compound of formula (XXVI):

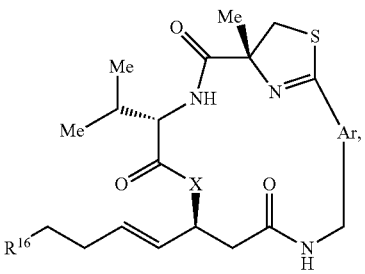
(XXVI)

wherein the structures, variables, activating agents, and nucleophile are as described elsewhere herein.

In some aspects, the compound of formula (XXVI) is a compound of formula (I-a), (I-b), or (I-c):

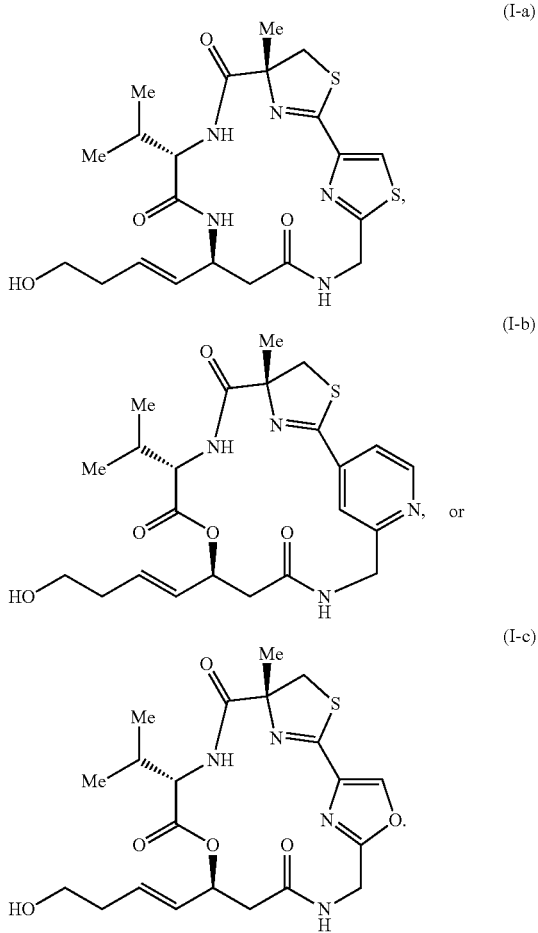

DETAILED DESCRIPTION

Figure 1:
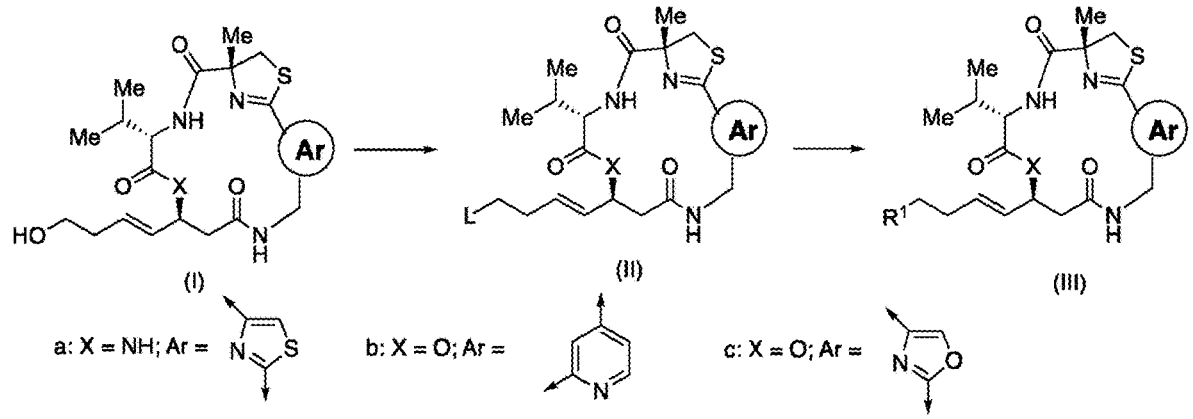
FIG. 1 depicts chemical reaction schemes, including Schemes 1, 2, and 3, that demonstrate certain methods and compounds disclosed herein.
Figure 1:
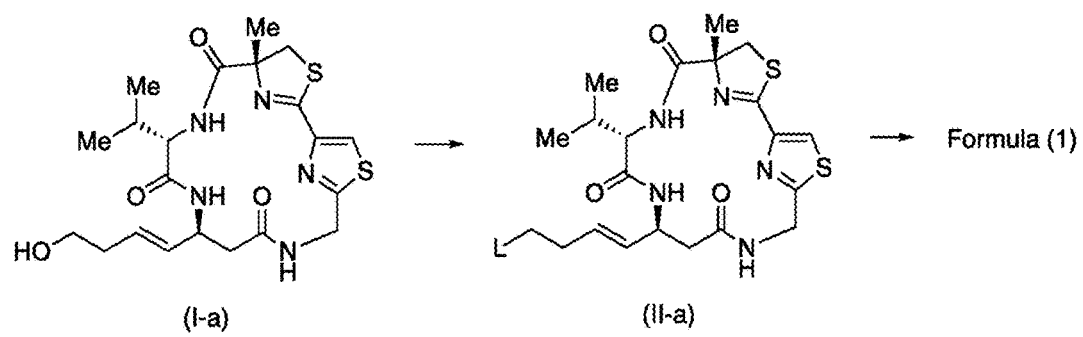
Figure 1:
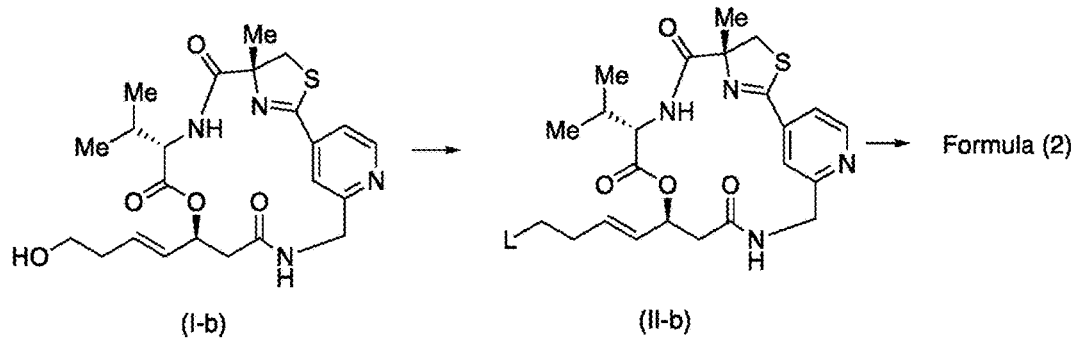

As used herein, a "suitable protecting group" is a chemical group that is used to temporarily block or protect a particular functional moiety, e.g., COOH, O, S, or N, on a molecule so that a reaction can be carried out selectively at another reactive site on the molecule. A suitable protecting group typically reacts with a COOH, O, S, or N functionality in acceptable yield to give a protected group that is stable to the projected reactions. A suitable protecting group typically should be selectively removable in acceptable yield by one or more reagents that do not react with other portions of the molecule, unless such reactions are desired. As detailed herein, a variety of suitable protecting groups may be employed to protect carboxylic acid, oxygen, sulfur, and nitrogen functionalities, and such protecting groups are termed herein, respectively, as "suitable carboxylic acid protecting groups," "suitable alcohol protecting groups," "suitable thiol protecting groups," and "suitable amine protecting groups." Such suitable protecting groups are well-known in the art and include those described in several published sources, including, for example, (1) Protective Groups in Organic Synthesis, Theodora W. Greene and Peter G. M. Wuts, 2006, published by John Wiley and Sons; and (2) Bioconjugate Techniques, Greg T. Hermanson, 2013, published by Academic Press; both of which are hereby incorporated by reference in their entireties.

"Suitable alcohol protecting groups" are well known in the art and include, for example, tert-butyldimethylsilyl (TBDMS or TBS), tert-butyldiphenylsilyl (TBDPS), or tetrahydropyran (THP).

"Suitable thiol protecting groups" are well known in the art and include, for example, triphenylmethyl (Trt or trityl).

"Suitable amine protecting groups" are well known in the art and include, for example, 9-fluorenylmethoxy carbamate (Fmoc), t-butyl carbamate (Boc), or benzyloxy carbamate (Cbz).

"Suitable carboxylic acid protecting groups" are well known in the art and include, for example, $C_1$-$C_6$ linear or branched alkyl, $C_1$-$C_6$ linear or branched alkyl substituted with one or more aryl or heteroaryl in any position, or alkylsilyl. In some aspects, the $C_1$-$C_6$ linear or branched alkyl is, for example, methyl, ethyl, propyl, isopropyl, allyl, butyl, 2-butyl, tert-butyl, benzyl, or substituted benzyl, each of which can be substituted with one or more aryl or heteroaryl in any position. In some aspects, the alkylsilyl is, for example, 2-(trimethylsilyl)ethyl.

In some aspects, any carboxylic, amine, or thiocarboxylic functionality on any compound disclosed herein can be present, e.g., as H, an alkali metal (or ion), an alkaline earth metal (or ion), a salt, or any combination thereof.

When a number of carbon atoms of a functional or other group (e.g., alkyl group) is specified herein, it is intended that the number refers to the exact number of carbon atoms, or range of carbon atoms, that is specified. For example, if an alkyl is specified to contain 4 to 8 carbon atoms, an alkyl group containing 12 carbon atoms would not qualify; rather, only an alkyl group that contains 4, 5, 6, 7, or 8 carbon atoms would qualify. In addition, when a number of carbon atoms is specified as a range, it is intended that any sub-range or individual number of carbon atoms falling within the indicated range are specifically contemplated, as if each such sub-range or individual carbon atom numbers are explicitly set forth herein. For example, a $C_1$-$C_{24}$ carbon atom range is intended to include 1, 2, 3, 4, 5, 6, 7, 8, 9, 10, 11, 12, 13, 14, 15, 16, 17, 18, 19, 20, 21, 22, 23, or 24 carbon atoms. In addition, all sub-ranges that can be made therefrom are also specifically contemplated, including, but not limited to, 1-2, 1-3, 1-4, 1-5, 1-6, 1-7, 1-8, 1-9, 1-10, 1-12, 1-14, 1-16, 1-18, 1-20, 1-22, 1-24, 2-3, 2-4, 2-5, 2-6, 2-7, 2-8, 2-9, 2-10, 2-12, 2-14, 2-16, 2-18, 2-20, 2-22, 2-24, 3-4, 3-5, 3-6, 3-7, 3-8, 3-9, 3-10, 3-12, 3-14, 3-18, 3-24, 4-5, 4-8, 4-10, 4-12, 4-16, 4-20, 4-24, 6-8, 6-10, 6-12, 6-16, 6-20, 6-24, 8-10, 8-12, 8-16, 8-20, 8-24, 10-14, 10-20, 10-24, 12-18, or 12-24 carbon atoms.

In performing the various reaction steps disclosed herein, any suitable reaction conditions may be used. Such reaction conditions may include a solvent, an acid, a base, a reagent, a catalyst, a time, a temperature, a pH, or any combination thereof. In some aspects, certain reaction products may be purified before proceeding to the next step, or certain reaction products may be carried forward crude to the next reaction step. The various reaction conditions and synthetic reactions disclosed herein are exemplary, but any suitable reaction conditions or synthetic reactions can be employed such as, for example, those disclosed in Advanced Organic Chemistry—Part B: Reactions and Synthesis, Francis A. Carey and Richard J. Sundberg, 4$^{th}$ Edition, 2001, published by Springer, hereby incorporated by reference in its entirety.

As shown in Scheme 1 in FIG. 1, disclosed herein is a method for preparing a compound of formula (III):

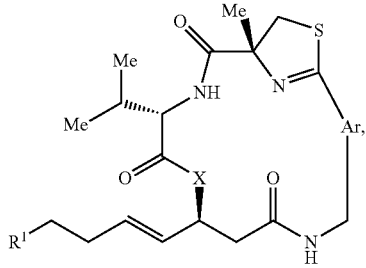
(III)

the method comprising:
reacting a compound of formula (I):

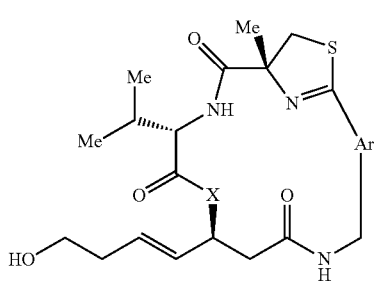
(I)

with an activating agent selected from $C_1$-$C_{20}$ linear or branched alkyl-sulfonyl halide, substituted alkyl-sulfonyl halide, arylsulfonyl halide, substituted arylsulfonyl halide, halo-phosphite (e.g., chlorophosphite), or a halogenating reagent, thereby forming a compound of formula (II):

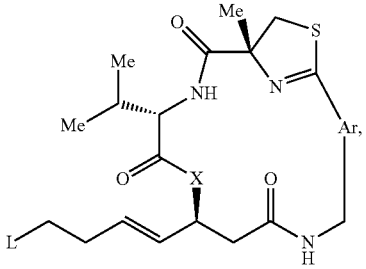
(II)

and reacting the compound of formula (II) with a nucleophile comprising an $R^1$ group, thereby forming the compound of formula (III).
wherein:
X is O or NH;
Ar is thiazolyl, pyridinyl, or oxazolyl;
L is a leaving group selected from $C_1$-$C_{24}$ linear or branched carbon sulfonate, substituted $C_1$-$C_{24}$ linear or branched sulfonate, arylsulfonate, substituted arylsulfonate, heteroarylsulfonate, substituted heteroarylsulfonate, phosphate, or halogen;
$R^1$ is $R^2COS$, $R^3S$, or $R^4R^5N$, and
$R^2$, $R^3$, $R^4$, and $R^5$ independently are hydrogen, $C_{1-24}$ linear alkyl (e.g., methyl, ethyl, n-propyl, n-butyl, n-pentyl, n-hexyl, n-heptyl, n-octyl and so forth), $C_1$-$C_{24}$ linear alkyl substituted with one or more aryl or heteroaryl in any position (e.g., substituted with phenyl, pyridinyl, furanyl, pyrrolyl, thiophenyl, and so forth, or any combination thereof), $C_1$-$C_{24}$ branched alkyl (e.g., isopropyl, isobutyl, sec-butyl, tert-butyl, and so forth), $C_1$-$C_{24}$ branched alkyl substituted with one or more aryl or heteroaryl in any position (e.g., isopropyl substituted with phenyl, isobutyl substituted with pyridinyl, and so forth), $C_3$-$C_{24}$ cyclic alkyl (e.g., cylopropyl, cyclobutyl, cyclopentyl, cyclohexyl, methylcyclopropyl, and so forth), $C_3$-$C_{24}$ cyclic alkyl substituted with one or more aryl or heteroaryl in any position (e.g., cyclohexyl substituted with phenyl, and so forth), $C_1$-$C_{24}$ alkenyl, $C_1$-$C_{24}$ alkynyl, aryl (e.g., naphthalenyl, phenyl, pryridinyl, furanyl, pyrrolyl, thiophenyl, and so forth), heteroaryl (e.g., pryridinyl, furanyl, pyrrolyl, thiophenyl, and so forth), diphenyl methyl, triphenylmethyl, or any substituted version thereof. In some aspects, $R^1$ is $R^2COS$ and $R^2$ is n-heptyl.

Also disclosed herein as shown in Scheme 1 in FIG. 1 is a method for preparing a compound of formula (III) comprising reacting the compound of formula (II) with a nucleophile comprising an $R^1$ group, wherein the variables in the compounds of formula (II) and (III) are as defined elsewhere herein. In other words, in some aspects, a method for preparing the compound of formula (III) starts from the compound of formula (II) rather than the compound of formula (I). However, in other aspects, a method for preparing the compound of formula (III) starts from the compound of formula (I) and passes through the compound of formula (II), as disclosed elsewhere herein.

In some aspects, L is any suitable leaving group. The term "leaving group" is well-known in the art, but, solely for illustration, a leaving group is a molecular fragment whose bond to an underlying molecule is broken, and the leaving group departs from the molecule with the pair of electrons from the broken bond. In a substitution reaction, a nucleophile typically forms a bond to the position on the underlying molecule where the leaving group was previously located. Suitable leaving groups include, for example, $C_1$-$C_{24}$ linear or branched carbon sulfonate, substituted $C_1$-$C_{24}$ linear or branched sulfonate (e.g., substituted with any group, such as alkyl, alkenyl, alkynyl, aryl, heteroaryl, heterocycle, halide, hydroxyl, alkoxyl, and so forth, or any combination thereof), arylsulfonate, substituted arylsulfonate (e.g., substituted with any group, such as alkyl, alkenyl, alkynyl, aryl, heteroaryl, heterocycle, halide, hydroxyl, alkoxyl, and so forth, or any combination thereof), heteroarylsulfonate, substituted heteroarylsulfonate (e.g., substituted with any group, such as alkyl, alkenyl, alkynyl, aryl, heteroaryl, heterocycle, halide, hydroxyl, alkoxyl, and so forth, or any combination thereof), phosphate, or halogen. For example, in some aspects, L is OMs, OTs, OTf, 2,2,2-trifluoroethanesulfonate, n-octanesulfonate, benzenesulfonate, OP(=O)(OMe)$_2$, OP(=O)(OEt)$_2$, OP(=O)(OPh)$_2$, I, Br, Cl, or F.

In some aspects, as shown in Scheme 1 in FIG. 1, disclosed herein is a method comprising producing the compound of formula (II) from a compound of formula (I):

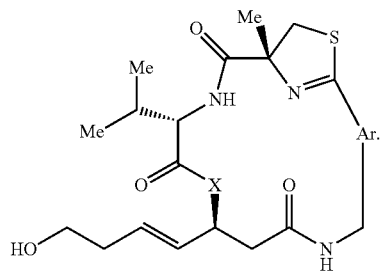

In some aspects, disclosed herein is a method comprising producing the compound of formula (II) from a compound of formula (IX):

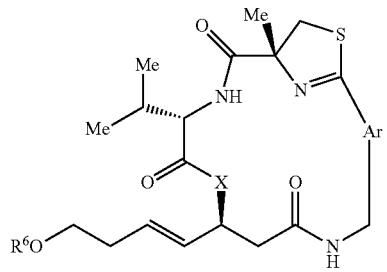

by converting OR$^6$ of the compound of formula (IX) into the leaving group L; wherein Re is H or a suitable alcohol protecting group.

In some aspects, converting ORe into the leaving group L comprises: when Re is the suitable alcohol protecting group, deprotecting the suitable alcohol protecting group to provide the compound of formula (IX) where R$^6$ is H; and reacting the compound of formula (IX) where Re is H with an activating agent selected from $C_1$-$C_{20}$ linear or branched alkyl-sulfonyl halide, substituted alkyl-sulfonyl halide, arylsulfonyl halide, substituted arylsulfonyl halide, halo-phosphite (e.g., chlorophosphite), or a halogenating reagent. Suitable specific activating agents are disclosed elsewhere herein.

In some aspects, the compound of formula (IX) is a compound of formula (I):

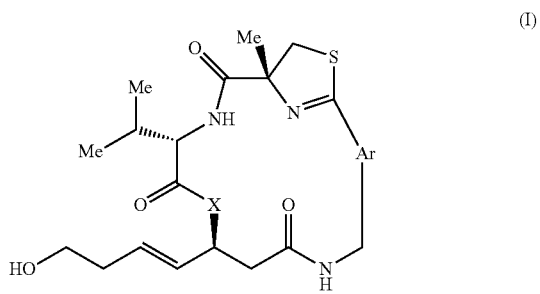

and the method comprises reacting the compound of formula (I) with an activating agent selected from $C_1$-$C_{20}$ linear or branched alkyl-sulfonyl halide, substituted alkyl-sulfonyl halide, arylsulfonyl halide, substituted arylsulfonyl halide, halo-phosphite (e.g., chlorophosphite), or a halogenating reagent, thereby forming the compound of formula (II).

In some aspects, the compound of formula (I) or the compound of formula (IX) is a compound of formula (I-a), (I-b), or (I-c):

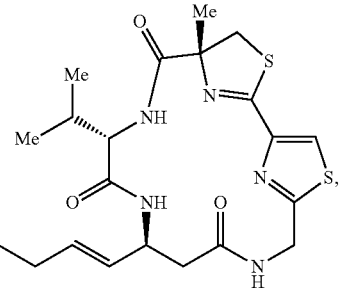

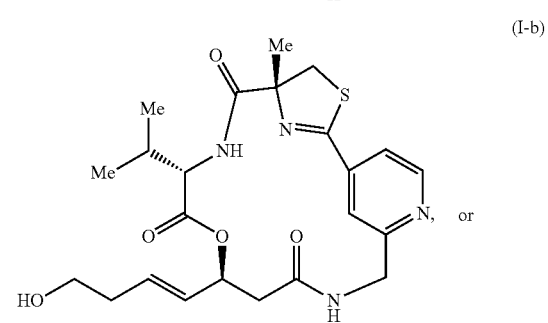

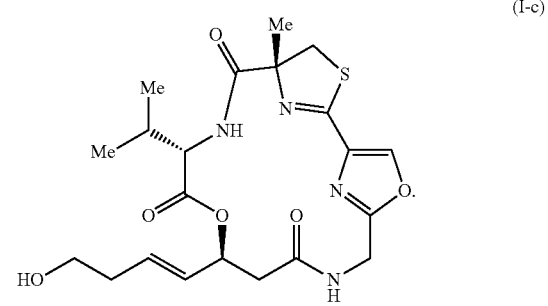

In some aspects, Ar is:

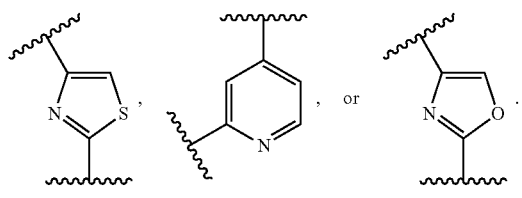 [SMILES: *c1csc(*)n1 ; *c1ccnc(*)c1 ; *c1coc(*)n1]

In some aspects, the nucleophile employed in the method is thiooctanoic acid, such that the compound of formula (III) is a compound of formula (XXV):

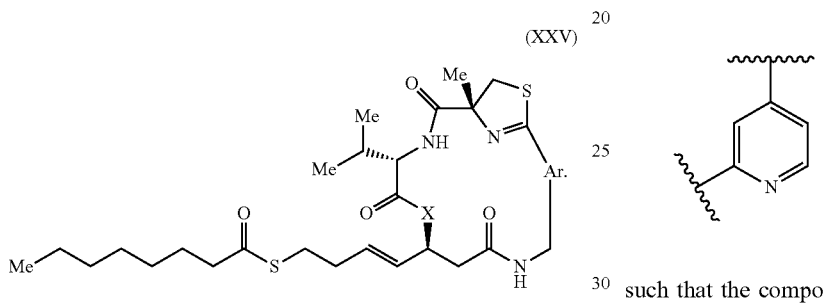

(XXV)

In some aspects, the nucleophile employed in the method is thiooctanoic acid, X is NH, and Ar is

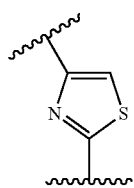 [SMILES: *c1csc(*)n1]

such that the compound of formula (III) is a compound of formula (1):

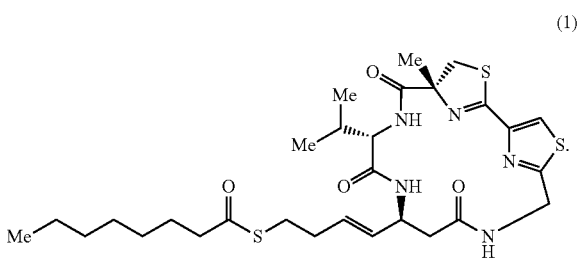 [SMILES: CCCCCCCC(=O)SCC/C=C/[C@@H]1CC(=O)NCc2nc(cs2)C2=N[C@@](C)(CS2)C(=O)N[C@@H](C(C)C)C(=O)N1]

(1)

In some aspects, disclosed herein is a method for preparing a compound of formula (1, III-a), depicted in Scheme 2 of FIG. 1:

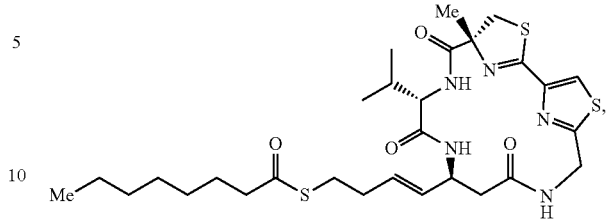

(1)

the method comprising producing the compound of formula (1) from a compound of formula (I-a) via formula (II-a), in which L is as defined elsewhere herein.

In some aspects, the nucleophile employed in the method is thiooctanoic acid, X is O, and Ar is such that the compound of formula (III) is a compound of formula (2):

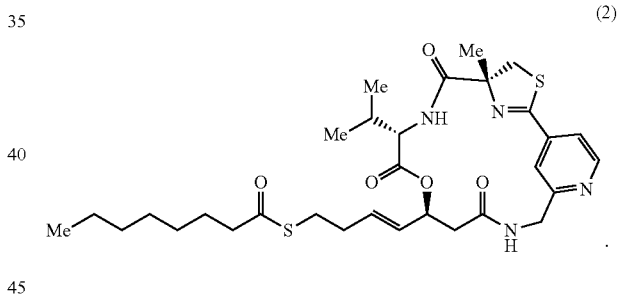

(2)

In some aspects, disclosed herein is a method for preparing a compound of formula (2, III-b), depicted in Scheme 3 of FIG. 1:

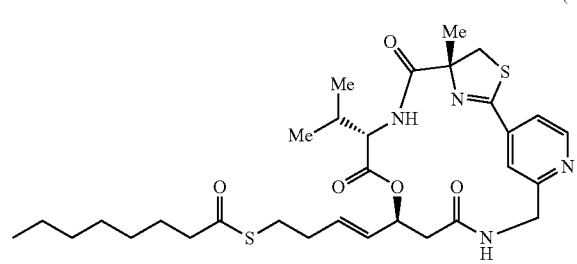

(2)

the method comprising producing the compound of formula (2) from a compound of formula (I-b) via formula (II-b), where L is a leaving group as defined elsewhere herein.

In some aspects, the nucleophile employed in the method is thiooctanoic acid, X is O, and Ar is

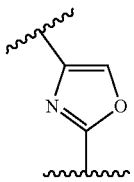 [SMILES: *c1coc(*)n1]

such that the compound of formula (III) is a compound of formula (3):

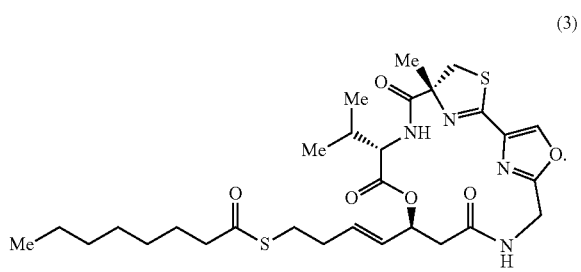 [SMILES: CCCCCCCC(=O)SCC/C=C/[C@@H]1CC(=O)NCc2nc(co2)C2=N[C@@](C)(CS2)C(=O)N[C@@H](C(C)C)C(=O)O1]

(3)

Figure 2:
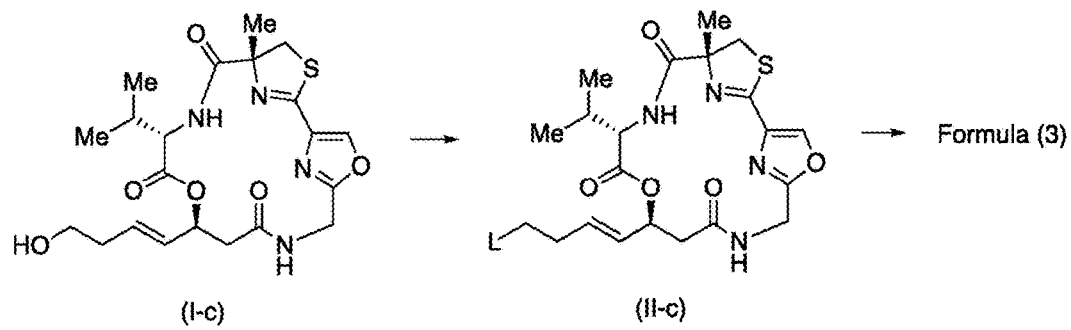
FIG. 2 depicts chemical reaction schemes, including Schemes 4 and 5, that demonstrate certain methods and compounds disclosed herein.
Figure 2:
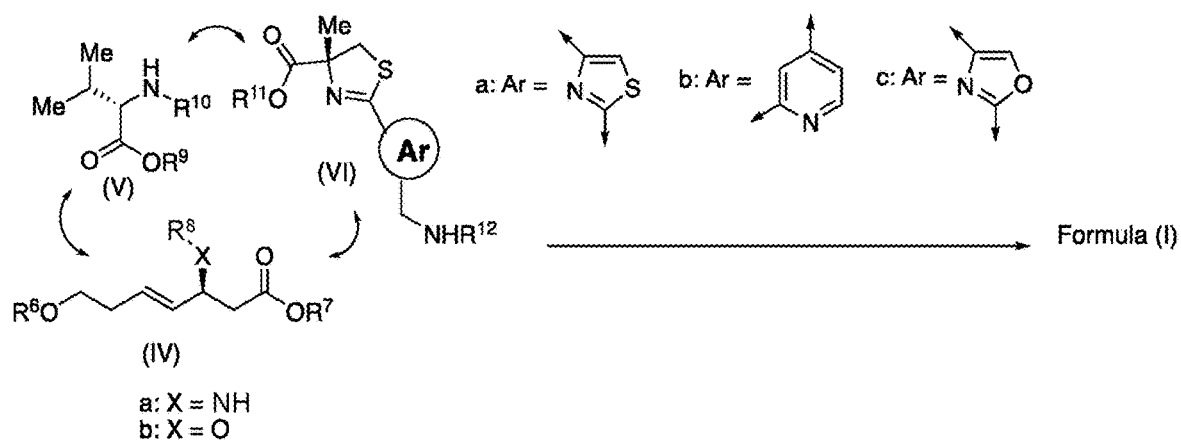

In some aspects, disclosed herein is a method for preparing a compound of formula (3, III-c), depicted in Scheme 4 of FIG. 2:

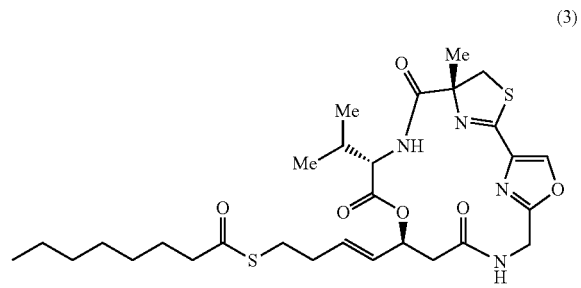 [SMILES: CCCCCCCC(=O)SCC/C=C/[C@@H]1CC(=O)NCc2nc(co2)C2=N[C@@](C)(CS2)C(=O)N[C@@H](C(C)C)C(=O)O1]

(3)

the method comprising producing the compound of formula (3) from a compound of formula (I-c) via formula (II-c), where L is a leaving group as defined elsewhere herein.

In some aspects, conversion of a compound of formula (I) to a compound of formula (II) with suitable activating reagent and suitable base in suitable solvent can be achieved at a temperature of −78 to 120° C., −50 to 80° C., −20 to 50° C., or −10 to 10° C.

In some aspects, suitable activating reagents include, but are not limited to, $C_1$-$C_{20}$ linear or branched alkyl-sulfonyl halide, substituted alkyl-sulfonyl halide, arylsulfonyl halide, substituted arylsulfonyl halide, halo-phosphite (e.g., chlorophosphite), halogenating reagents, mesyl chloride, tosyl chloride, trifluoromethanesulfonyl chloride, 2,2,2-trifluoroethanesulfonyl chloride, benzenesulfonyl chloride, n-octanesulfonyl chloride, or any combination thereof.

In some aspects, suitable bases include, but are not limited to, organic bases such as triethylamine, diisopropylethylamine, pyridine, lutidine, collidine, DBU, DABCO, and inorganic bases such as $NaHCO_3$, $KHCO_3$, $Na_2CO_3$, $K_2CO_3$, $Cs_2CO_3$, NaOH, KOH, or any combination thereof.

In some aspects, suitable solvents include, but are not limited to, hydrocarbon, toluene, chlorobenzene, isopropyl acetate, ethyl acetate, methyl acetate, diethyl ether, CPME, MTBE, THF, 2-methyl-THF, dioxane, acetone, methyl ethyl ketone, acetonitrile, DMF, DMAC, DMSO, DCM, water, or any combination thereof In some aspects, conversion of a compound of formula (II) to a compound of formula (III) with suitable nucleophile in a suitable solvent can be achieved at a temperature of −20 to 70° C., −10 to 60° C., 0 to 50° C., or 0 to 30° C.

In some aspects, suitable solvents include, but are not limited to, hydrocarbon, toluene, chlorobenzene, isopropyl acetate, ethyl acetate, methyl acetate, diethyl ether, CPME, MTBE, THF, 2-methyl-THF, dioxane, acetone, methyl ethyl ketone, acetonitrile, DMF, DMAc, DMSO, DCM, water, or any combination thereof.

In some aspects, suitable nucleophiles include, but are not limited to, $R^2COS^-$, $R^3S^-$, or $R^4R^5N^-$; $R^2$, $R^3$, $R^4$, $R^5$ are defined elsewhere herein. In some aspects, the nucleophile is n-$C_7H_{15}COS^-$.

In some aspects, disclosed herein is a method for the preparation of a compound of formula (I), depicted in Scheme 5 of FIG. 2. In some aspects, the method comprises producing the compound of formula (I) from a compound of formula (IV; beta-functioned ester), a compound of formula (V), and a compound of formula (VI). The compound of formula (I) can be prepared using standard ester formation and amide formation reactions with a suitable protecting group on nitrogen and/or oxygen atoms. The order of bond formation between three components (IV, V, and VI) generally is not important, and thus any order of bond formation is feasible. In Scheme 5 of FIG. 2, $R^6$ is H or a suitable alcohol protecting group; $R^7$, $R^9$, and $R^{11}$ independently are H, an alkali metal ion, an alkaline earth metal ion, or a suitable carboxylic acid protecting group, such as, for example, $C_1$-$C_6$ alkyl group, substituted $C_1$-$C_6$ alkyl group, 2-trimethylsilylethyl, benzyl, or substituted benzyl; $R^8$, $R^{10}$ and $R^{12}$ are independently, H, or a suitable nitrogen protecting group. Ar is thiazole, pyridine, or oxazole. X is O or NH. In some aspects, any N atom is a quaternary ammonium.

In some aspects, the method further comprises producing the compound of formula (I):

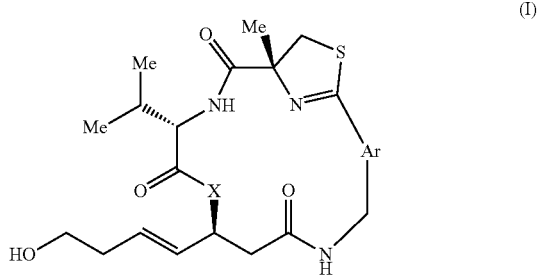

(I)

or the compound of formula (IX):

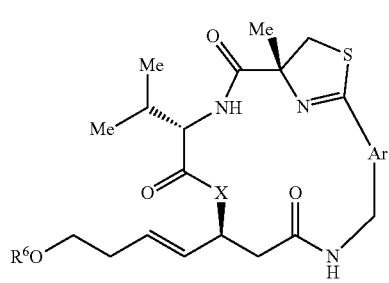

(IX)

from one or more reactions comprising:
a compound of formula (IV):

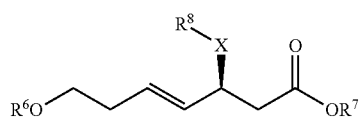

(IV)

a compound of formula (V):

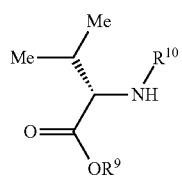

(V)

and a compound of formula (VI):

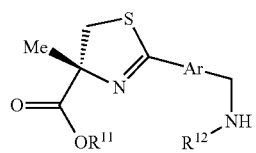

(VI)

wherein:
$R^8$ is H or a suitable alcohol protecting group;
$R^8$, $R^{10}$, and $R^{12}$ independently are H, a suitable amine protecting group, or a chiral group;
$R^7$, $R^9$, and $R^{11}$ independently are H, an alkali metal ion, an alkaline earth metal ion, or a suitable carboxylic acid protecting group;
optionally wherein the suitable carboxylic acid protecting group is selected from $C_1$-$C_6$ linear or branched alkyl, $C_1$-$C_6$ linear or branched alkyl substituted with one or more aryl or heteroaryl in any position, or alkylsilyl;
optionally wherein the $C_1$-$C_6$ linear or branched alkyl, or the $C_1$-$C_6$ linear or branched alkyl substituted with one or more aryl or heteroaryl in any position, is selected from methyl, ethyl, propyl, isopropyl, allyl, butyl, 2-butyl, tert-butyl, benzyl, or substituted benzyl;
optionally wherein the alkylsilyl is 2-(trimethylsilyl) ethyl; and
optionally wherein any N atom is a quaternary ammonium.

In some aspects, the compound of formula (I) or the compound of formula (IX) is a compound of formula (I-a), (I-b), or (I-c):

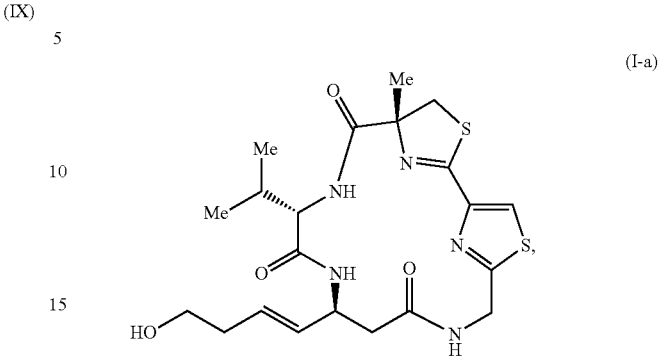

(I-a)

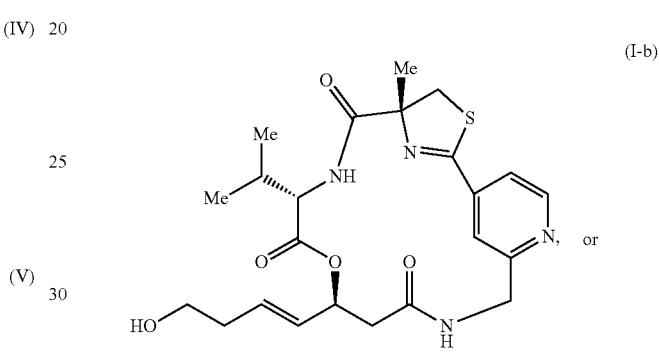

(I-b)

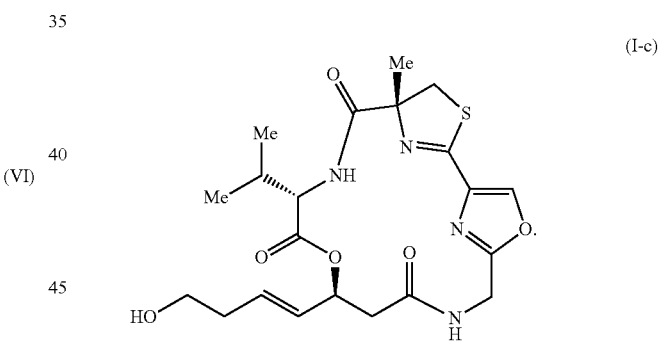

(I-c)

Figure 3:
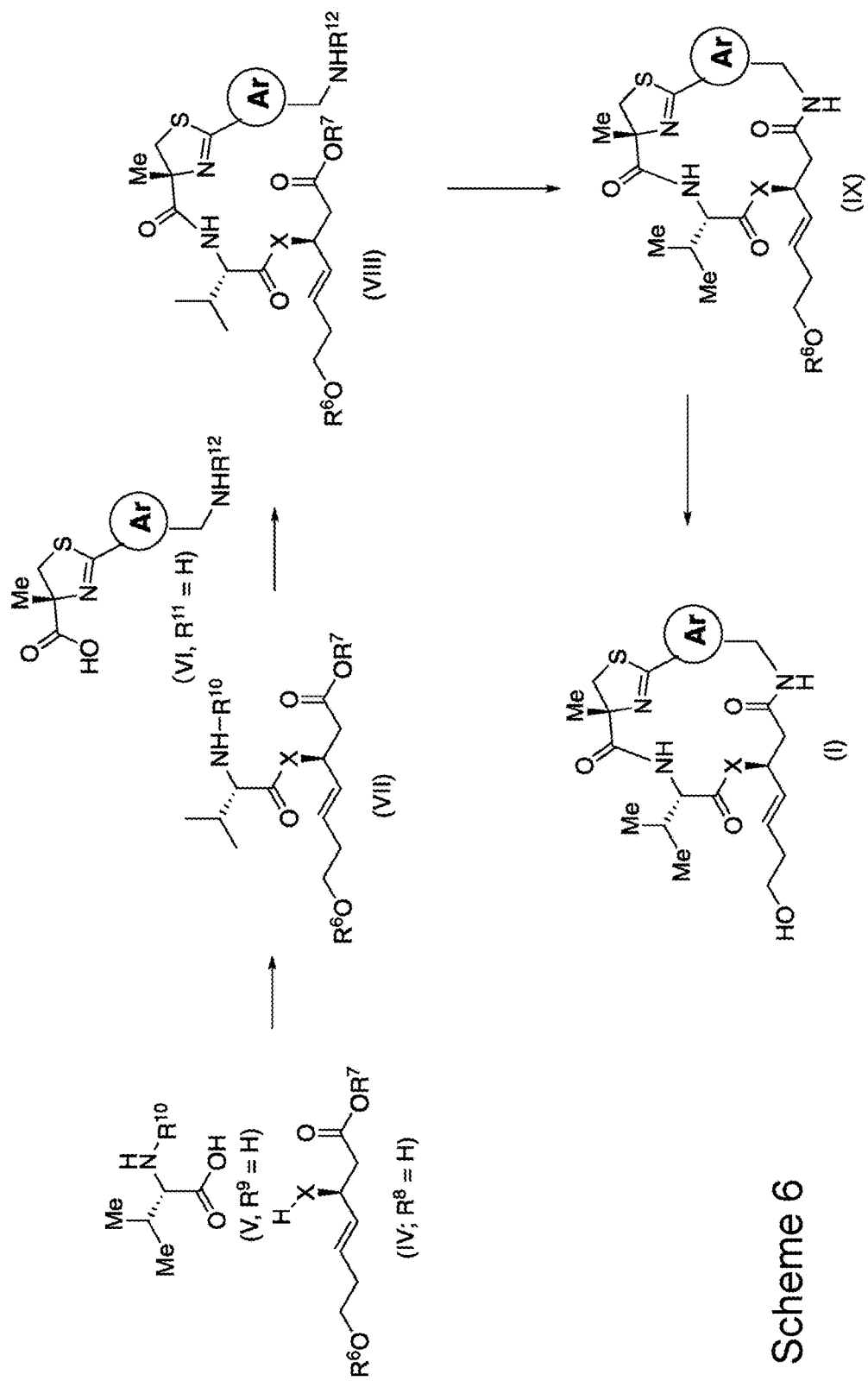
FIG. 3 depicts a chemical reaction scheme, including Scheme 6, that demonstrate certain methods and compounds disclosed herein.

In some aspects, the compound of formula (I) is produced by a method depicted in Scheme 6 of FIG. 3, comprising:
reacting via condensation of a compound of formula (IV, $R^8$=H) with a compound of formula (V, $R^9$=H) to form a compound of formula (VII);
reacting the compound of formula (VII, $R^{10}$=H) with a compound of formula (VI, $R^{11}$=H) under amidation conditions to form a compound of formula (VIII);
reacting the compound of formula (VIII, $R^7$ and $R^{11}$=H) under amidation conditions to from a macrocyclic compound of formula (IX);
reacting the compound of formula (IX) under deprotection conditions to remove the alcohol protecting group to from a compound of formula (I).

In some aspects, the compound of formula (IV) is reacted with the compound of formula (V) via condensation to form a compound of formula (VII):

(VII)

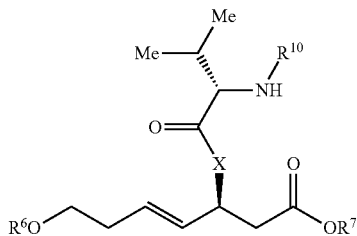

the compound of formula (VII) is reacted with the compound of formula (VI) via amidation to form a compound of formula (VIII):

(VIII)

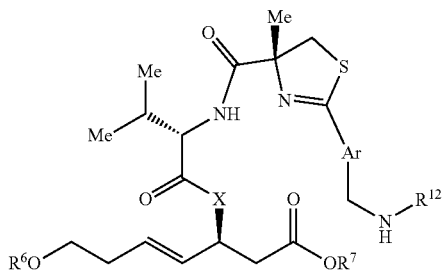

and the compound of formula (VIII) is reacted by amidating ring closure to form the compound of formula (IX), in which $R^6$, $R^7$, $R^{10}$, and $R^{12}$ are as defined elsewhere herein. In some aspects, any N atom is a quaternary ammonium.

In some aspects, $R^6$ is H or a suitable alcohol protecting group; and in reacting the compound of formula (IV) with the compound of formula (V): $R^8$ is H, and when X is N, the N is neutral or positively charged; $R^7$ is a suitable carboxylic acid protecting group; $R^{10}$ is a suitable amine protecting group; and $R^9$ is H, an alkali metal ion, or an alkaline earth metal ion;

in reacting the compound of formula (VI) with the compound of formula (VII): $R^7$ is a suitable carboxylic acid protecting group; $R^{10}$ is H, and optionally $R^{10}$ is attached to a positively charged nitrogen atom; $R^{11}$ is H, an alkali metal ion, or an alkaline earth metal ion; and $R^{12}$ is a suitable amine protecting group; and in reacting the compound of formula (VIII) by amidating ring closure: $R^8$ is H, an alkali metal ion, or an alkaline earth metal ion, and when X is N, the N is neutral or positively charged; and $R^{12}$ is H, and optionally $R^{12}$ is attached to a positively charged nitrogen atom.

In some aspects, selection of a protecting group is properly chosen based on orthogonality with other protecting groups. Suitable methods for removal of protecting groups for a given functional group depends on the nature of protecting groups in the same molecule.

In some aspects, suitable preferred nitrogen protecting groups are Boc or Fmoc. Those protecting groups can be selectively removed by acidic conditions or basic conditions.

In some aspects, suitable carboxylic acid protecting groups are $C_1$-$C_6$ alkyl group, substituted $C_1$-$C_6$ alkyl group, 2-trimethylsilylethyl, benzyl, or substituted benzyl. In some aspects, suitable carboxylic acid protecting groups are methyl, ethyl, or 2-trimethylsilylethyl. Such protecting groups can be selectively removed by basic conditions and acidic conditions.

In some aspects, condensation reagents are used to prepare an ester bond or an amide bond from carboxylic acids and alcohols or amines. In some aspects, condensation reagents include HATU, EDC, DCC, T3P, HBTU, TATU, TBTU, COMU, HOTU, BOP, PyBOP, and PyBroP.

Figure 4:
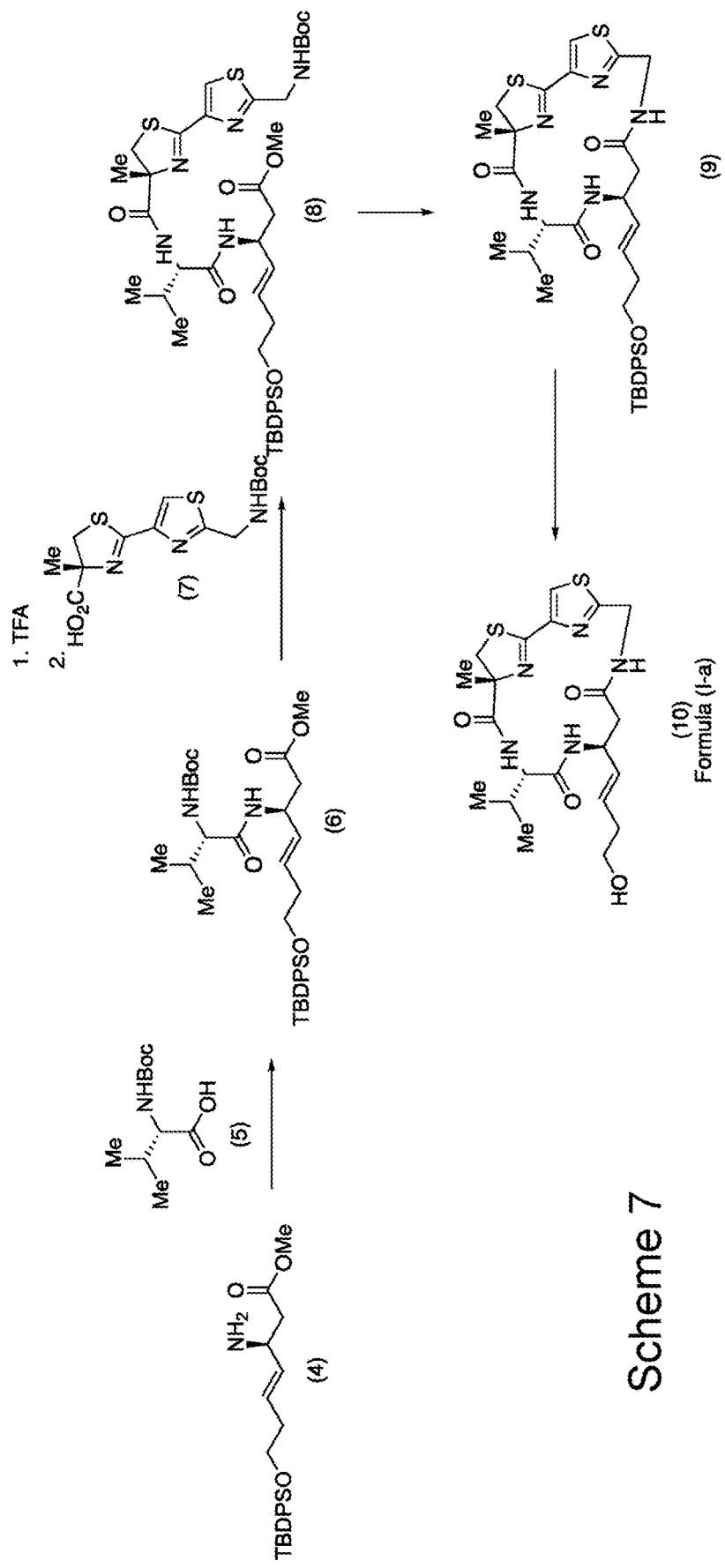
FIG. 4 depicts a chemical reaction scheme, including Scheme 7, that demonstrates certain methods and compounds disclosed herein.

In some aspects, the compound of formula (I-a) is prepared as depicted in Scheme 7 of FIG. 4. Protecting groups and reaction conditions are the same as described elsewhere herein for the same or similarly structured compounds. The protecting groups and reaction conditions depicted in Scheme 7 are merely exemplary and not to be construed as limiting in any way. Compound 7 has been reported in references 1-3, which are hereby incorporated by reference in their entireties for all purposes.

Figure 5:
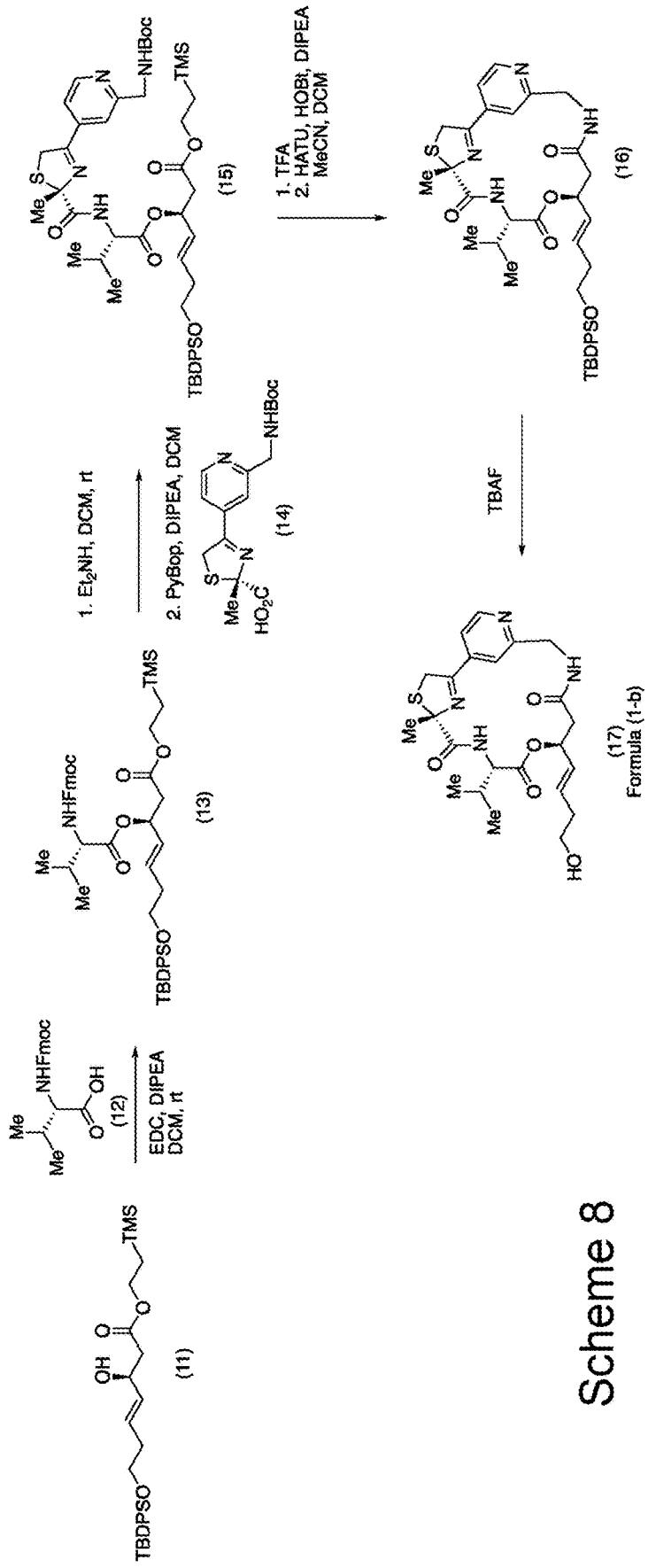
FIG. 5 depicts a chemical reaction scheme, including Scheme 8, that demonstrates certain methods and compounds disclosed herein.

In some aspects, the compound of formula (I-b) is prepared as depicted in Scheme 8 in FIG. 5. The protecting groups and reaction conditions are the same as described elsewhere herein for the same or similarly structured compounds. The protecting groups and reaction conditions depicted in Scheme 8 are merely exemplary and not to be construed as limiting in any way. Preparation of compound 14 has been reported in reference 4, hereby incorporated by reference in its entirety for all purposes.

In some aspects, the compound of formula (I-c) is prepared as depicted in Scheme 9. Protecting groups and reaction conditions are the same as described elsewhere herein for the same or similarly structured compounds. The protecting groups and reaction conditions depicted in Scheme 9 are merely exemplary and not to be construed as limiting in any way. Preparation of compound 18 has been reported in reference 5, hereby incorporated by reference in its entirety for all purposes.

Figure 6:
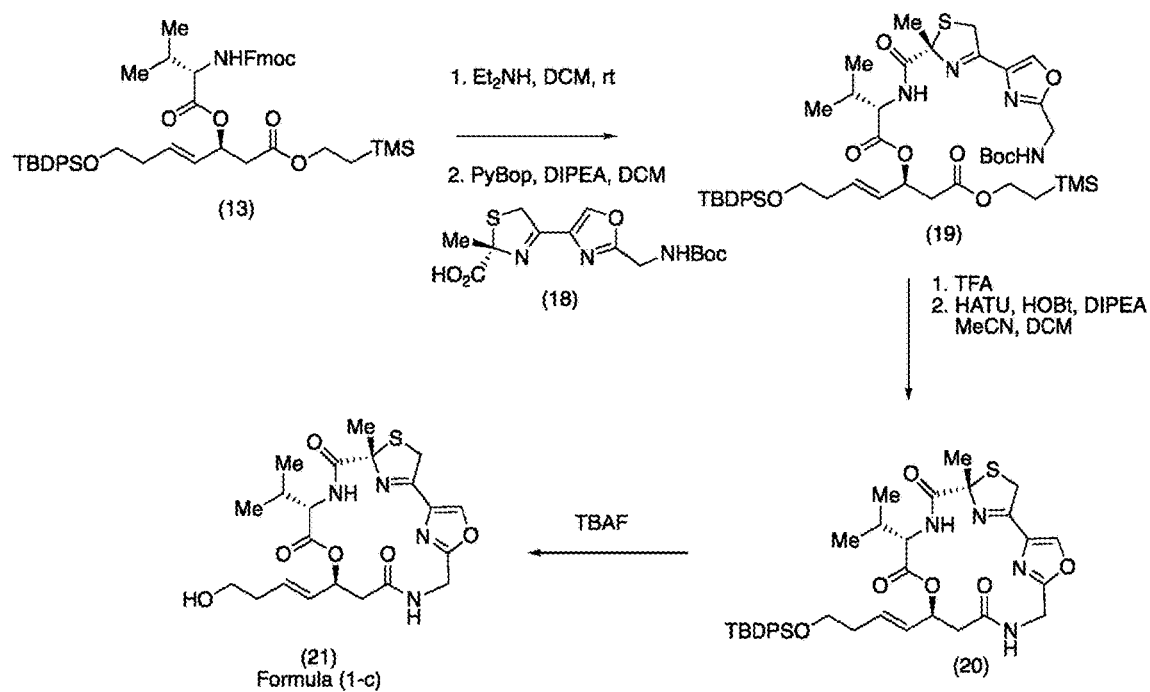
FIG. 6 depicts chemical reaction schemes, including Schemes 9 and 10, that demonstrate certain methods and compounds disclosed herein.
Figure 6:
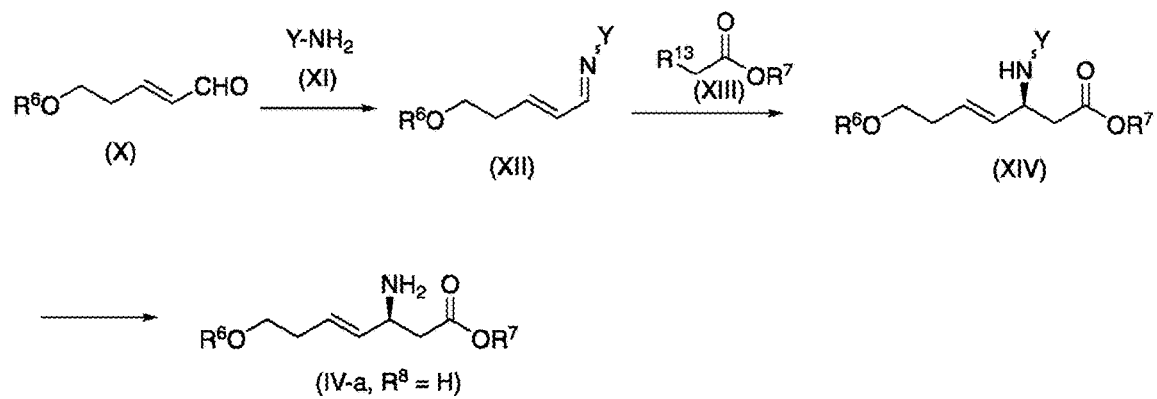

In some aspects, the compound of formula (IV-a, $R^8$=H) is produced by a method, depicted in Scheme 10 of FIG. 6, comprising:

reacting via imine formation a compound of formula (X) with a chiral auxiliary of formula (XI) to form a compound of formula (XII);

reacting the compound of formula (XII) via nucleophilic addition with a compound of formula (XIII) to form the compound of formula (XIV);

and cleaving N—Y bond to from the compound of formula (IV-a, $R^8$=H), in which Y is a chiral group sufficient to effect a diastereoselective nucleophilic addition of the compound of formula (XIII) to a compound of formula (XII) to form the compound of formula (IV-a) as a majority product, in which $R^{13}$ is Cl, Br, I, F, alkali metal, an alkali earth metal, ZnX, CuX, Cu, or a transition metal, in which each X in ZnX or CuX independently is a halide (e.g., F, Cl, Br, or I).

In some aspects, X is NH and the method further comprises producing the compound of formula (IV) by:

reacting via imine formation a compound of formula (X):

(X)

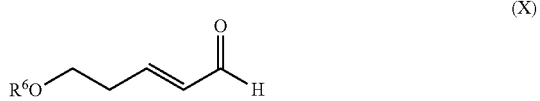

with a chiral auxiliary of formula (XI):

Y—NH$_2$   (XI)

to form a compound of formula (XII):

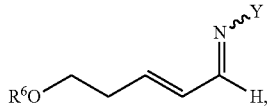
(XII)

reacting the compound of formula (XII) via nucleophilic addition with a compound of formula (XIII):

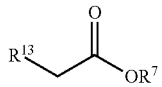
(XIII)

to form the compound of formula (IV) where X is NH and $R^8$ is chiral group Y:

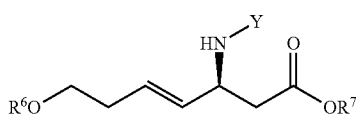
(IV)

and cleaving the N—Y bond to form the compound of formula (IV) where $R^8$ is H, and when X is N, the N is neutral or positively charged,
wherein:
Y is a chiral group sufficient to effect a diastereoselective nucleophilic addition of the compound of formula (XIII) to the compound formula (XII) to form the compound of formula (IV) as a majority product where $R^8$ is chiral group Y,
$R^6$ is a suitable alcohol protecting group,
$R^7$ is a suitable carboxylic acid protecting group;
optionally wherein the carboxylic acid protecting group is selected from $C_1$-$C_6$ linear or branched alkyl, $C_1$-$C_6$ linear or branched alkyl substituted with one or more aryl or heteroaryl in any position, or alkylsilyl;
optionally wherein the $C_1$-$C_6$ linear or branched alkyl, or the $C_1$-$C_6$ linear or branched alkyl substituted with one or more aryl or heteroaryl in any position, is selected from methyl, ethyl, propyl, isopropyl, allyl, butyl, 2-butyl, tert-butyl, benzyl, or substituted benzyl; and
optionally wherein the alkylsilyl is 2-(trimethylsilyl) ethyl; and $R^{13}$ is H, a halide, or a metal comprising Li, Na, K, ZnBr, ZnCl, CuCl, CuBr, CuI, Cu, or any combination thereof.
In some aspects, the chiral auxiliary of formula (XI) is:

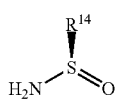
(XI)

wherein $R^{14}$ is $C_{1-6}$ linear and branched alkyl or aromatic or heteroaromatic. In some aspects, $R^{10}$ is tert-butyl, p-tolyl, alkyl, an aromatic group, or any substituted versions thereof. In some aspects, the compound of formula (XI) is (R)-tert-butanesulfinamide.

In some aspects, the compound of formula (XIII) is bromoacetate ester, which is converted to the corresponding Reformatsky type intermediate in the presence of Zn metal with/without Cu(I) halides. The Reformatsky intermediate reacts with imine (XII) to form a compound of formula (XIV).

In some aspects, suitable solvents for Reformatsky type reaction are THF, 2-methyl THF, or a combination thereof.

In some aspects, suitable temperatures for Reformatsky include −20 to 50° C., −15 to 30° C., or 0 to 5° C.

In some aspects, cleavage of the N—Y bond can be done under acidic conditions, such as HCl. Suitable solvents for N—Y bond cleavage are 1,4-dioxane, diethyl ether, THF, MTBE, or a combination thereof.

In some aspects, suitable temperatures for N—Y bond cleavage include −10 to 50° C., −5 to 40° C., or 0 to 30° C.

Figure 7:
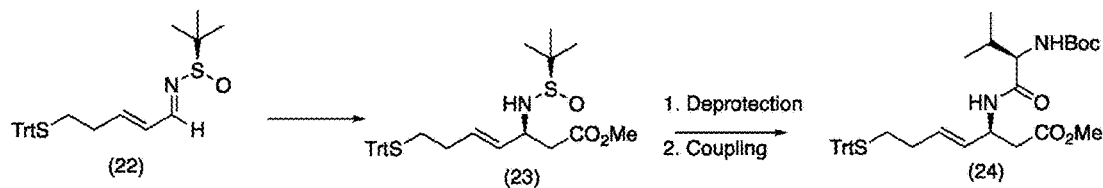
FIG. 7 depicts chemical reaction schemes, including Schemes 11 and 12, that demonstrate certain methods and compounds disclosed herein.
Figure 7:
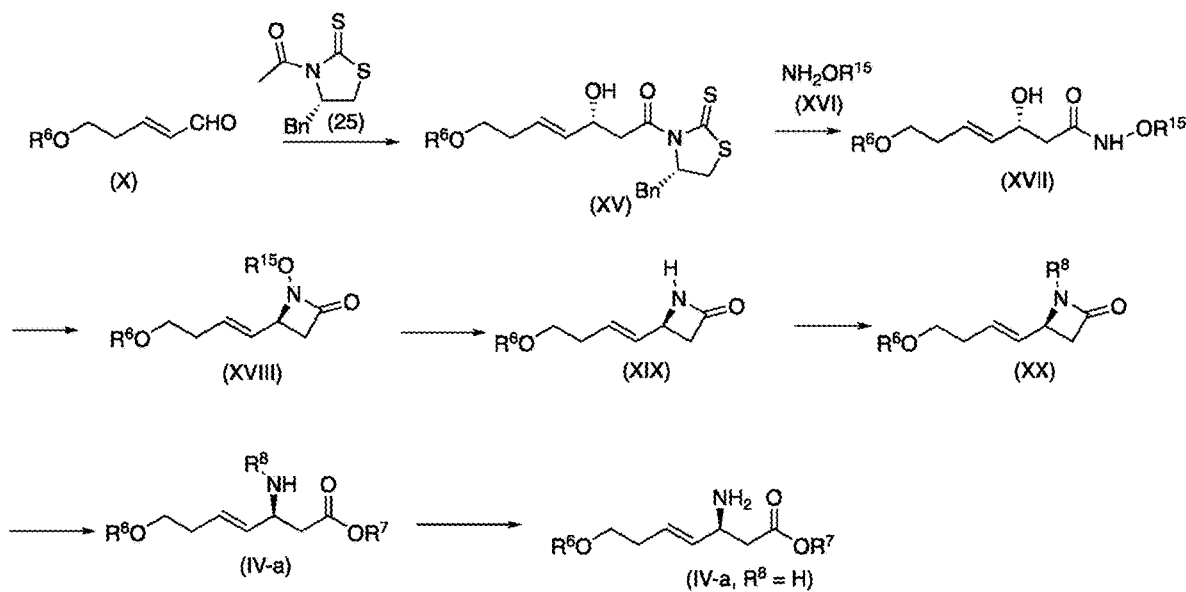

In some aspects, the synthetic method depicted in Scheme 10 in FIG. 6 is applied in the synthesis of the S-Trt protected compound 24 by replacing $OR^6$ with S-Trt as depicted in Scheme 11 in FIG. 7. Preparation of compounds 1 from compound 24 have been reported in reference 1, and preparation of compound 22 has been reported in reference 6, both of which are hereby incorporated by reference in their entireties.

In some aspects, the compound of formula (IV-a) is produced by a method, depicted in Scheme 12 of FIG. 7, comprising:
reacting via Evans type diastereoselective aldol reaction between a compound of formula (X) with Evans chiral auxiliary 25 to form a compound of formula (XV) as a major product;
reacting a compound of formula (XV) with a compound of formula (XVI) to form a compound of formula (XVII);
reacting a compound of formula (XVII) under Mitsunobu reaction conditions to form a compound of formula (XVIII);
reducing N—O bond of a compound of formula (XVIII) to form a compound of formula (XIX);
protecting the resulting free nitrogen of a compound of formula (XIX) with a nitrogen protecting group to form a compound of formula (XX);
opening a beta-lactam of formula (XX) to form a compound of formula (IV-a),
removing the protecting group of a compound of formula (IV-a) to form a compound of formula (IV-a, $R^8$=H);
wherein
$R^6$, $R^7$, and $R^8$ are defined elsewhere herein; $R^{15}$ is $C_1$-$C_6$ alkyl or benzyl. Formula (XVI) may be free base or its salts.

Figure 8:
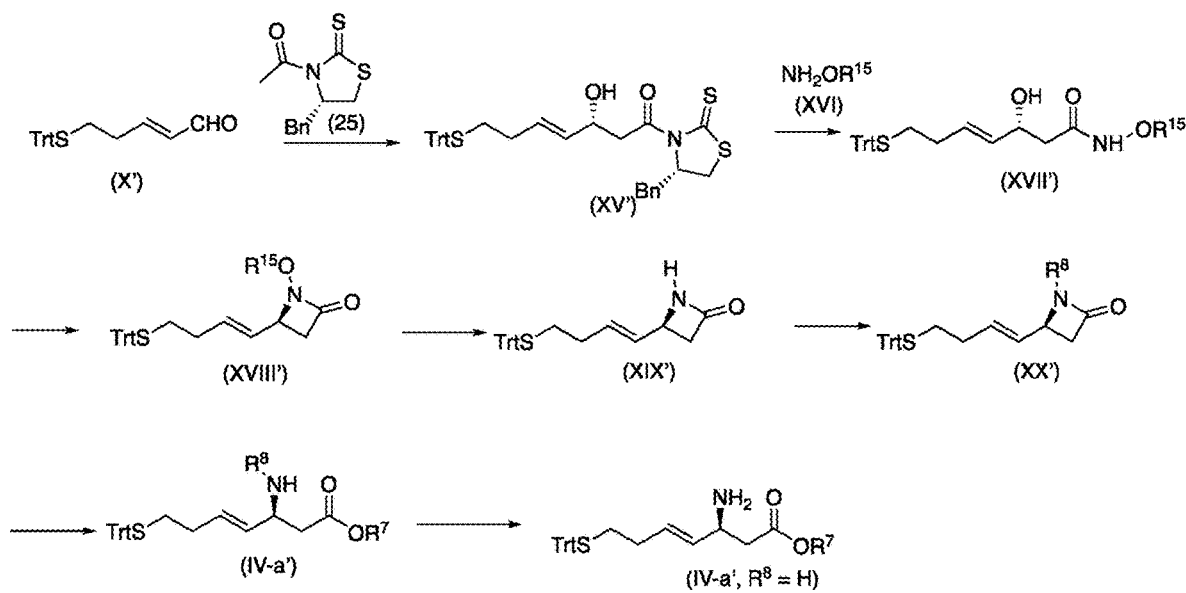
FIG. 8 depicts chemical reaction schemes, including Schemes 13, 14, and 15, that demonstrate certain methods and compounds disclosed herein.
Figure 8:
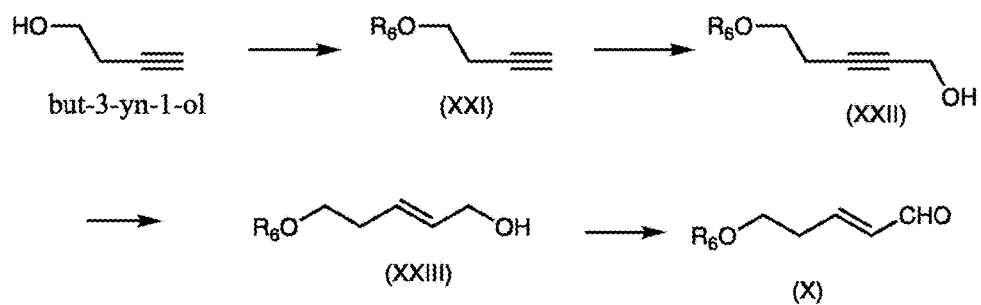
Figure 8:
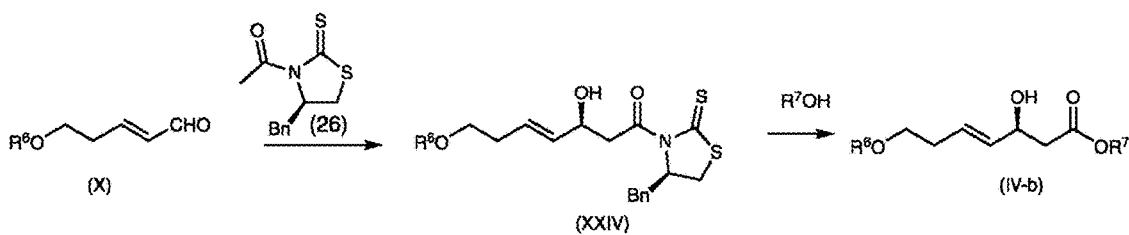

In some aspects, disclosed is a synthetic route depicted in Scheme 13 of FIG. 8 to prepare the corresponding S-Trt derivative (IV-a', $R^8$=H) from a compound (X') by modifying the synthetic route in Scheme 12 of FIG. 7 by replacing $OR^6$ with S-Trt. Preparation of compounds 1 from formula (IV-a', $R^8$=H) have been reported in reference 1, In some aspects, the compound of formula (X) is produced as shown in Scheme 14 of FIG. 8 by a method comprising:
protecting hydroxyl group of but-3-yn-1-ol with a suitable protecting group to form a compound of formula (XXI),
reacting a compound of formula (XXI) with strong base, such as n-BuLi, LDA, LiHMDS, NaHMDS, KHMDS, EtMgX, MeMgX, iPrMgX, to generate the corresponding anion then trapped with formaldehyde, paraformaldehyde, or trioxane to form a compound of formula (XXII), reducing a compound of formula (XXII) with DIBAL to form a compound of formula (XXIII), and oxidizing a compound of formula (XXIII) to form a compound of formula (X).

In some aspects, the compound of formula (IV-b) is produced in Scheme 15 of FIG. 8 by a method comprising:

reacting via Evans type diastereoselective aldol reaction between a compound of formula (X) with Evans chiral auxiliary 26 to form a compound of formula (XXIV) as a major product; and reacting a compound of formula (XXIV) with alcohol ($R^7OH$) to form a compound of formula (IV-b).

In some aspects, X is O, and the method comprises producing the compound of formula (IV) by:

reacting via an aldol addition a compound of formula (X):

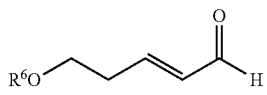

(X)

with a chiral auxiliary of formula (XXVIII):

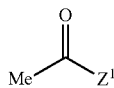

(XXVIII)

wherein $Z^1$ is a chiral group sufficient to effect a diastereoselective aldol addition to form a compound of formula (XXVIX):

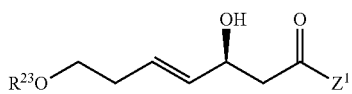

(XXVIX)

and performing an esterification on the compound of formula (XXVIX) to produce the compound of formula (IV) where X is O. In some aspects, the chirality of the $Z^1$ group controls the stereochemistry of a reaction by causing a particular diastereomer to be formed as the majority product in an aldol addition. While at least two products are possible in such an aldol addition, one diastereomeric product is formed in a greater yield than the other possible diastereomeric products. In some aspects, the compound of formula (XXVIII) is any known compound that can effect a such a diastereoselective aldol addition, such as an Evans-type oxazolidinone chiral auxiliary, Evans-type oxazolidinethione chiral auxiliary, Evans-type thiazolidinethione chiral auxiliary, or Crimmins-type thiazolidinethione chiral auxiliary.

Figure 9:
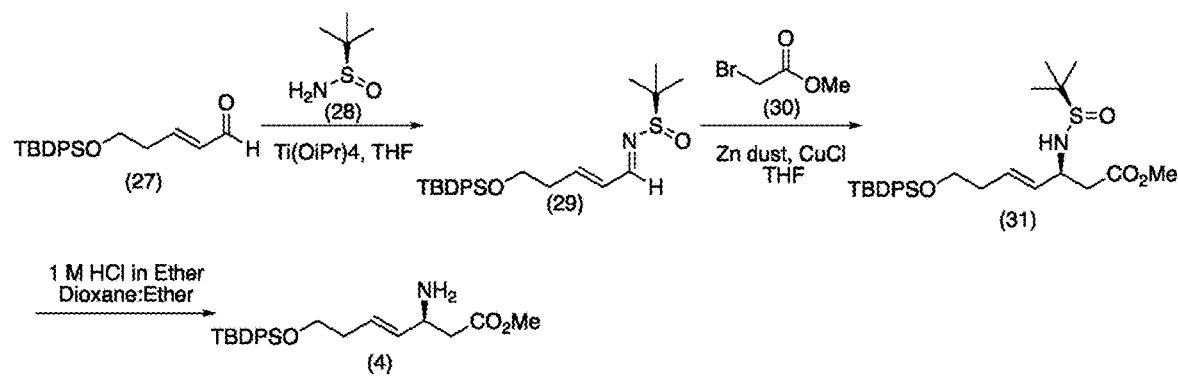
FIG. 9 depicts chemical reaction schemes, including Schemes 16 and 17, that demonstrate certain methods and compounds disclosed herein.
Figure 9:
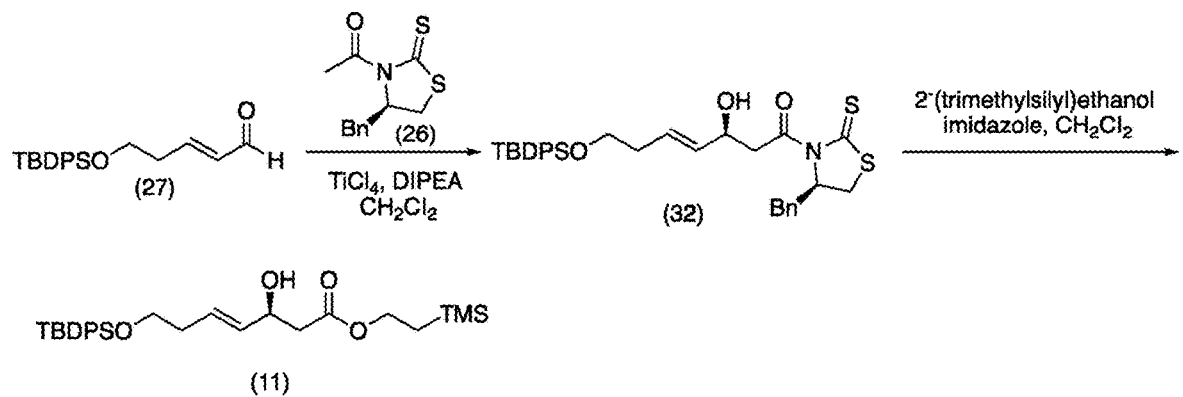

In some aspects, compound 4 is prepared as disclosed elsewhere herein for the same or similarly structured compounds, as shown in Scheme 16 of FIG. 9. The choice of reagents and protective groups is exemplary and not intended to be limiting in any way.

In some aspects, the synthetic method depicted in Scheme 10 of FIG. 6 is applied in the synthesis of TBDPS protected compound 4 by replacing $R^6$ with TBDPS as depicted in Scheme 16 of FIG. 9. Preparation of compound 10 from compound 4 is described elsewhere herein for the same or similarly structured compounds.

In some aspects, compound 11 is prepared as described elsewhere herein for the same or similarly structured compounds, as shown in Scheme 17 of FIG. 9. The choice of reagents and protective groups is exemplary and not intended to be limiting in any way.

In some aspects, disclosed is a compound of formula (XXVI):

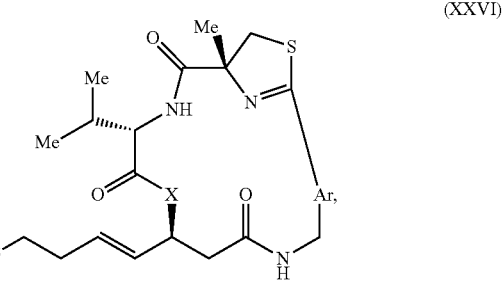

(XXVI)

wherein:

X is O or NH;

Ar is thiazolyl, pyridinyl, or oxazolyl;

$R^{16}$ is OH, $OR^6$, or L;

$R^6$ is a suitable alcohol protecting group; and

L is a leaving group selected from $C_1$-$C_{24}$ linear or branched carbon sulfonate, substituted $C_1$-$C_{24}$ linear or branched sulfonate, arylsulfonate, substituted arylsulfonate, heteroarylsulfonate, substituted heteroarylsulfonate, phosphate, or halogen.

In some aspects, the compound of formula (XXVI) is a compound of formula (I-a), (I-b), or (I-c):

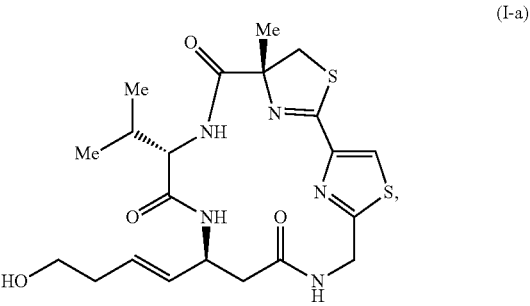

(I-a)

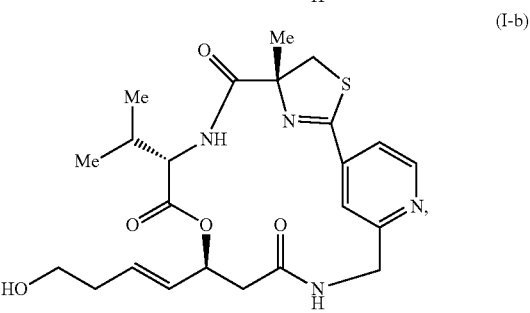

(I-b)

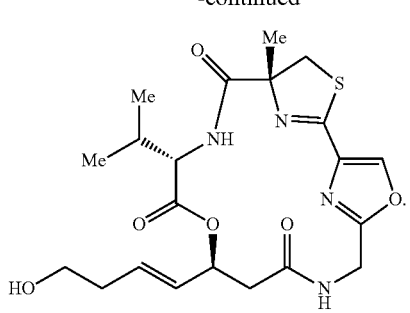
(I-c)

In some aspects, $R^{16}$ is OH. In some aspects, $R^{16}$ is L. In some aspects, $R^{16}$ is $OR^6$.

In some aspects, X is O, and Ar is pyridinyl. In some aspects, X is NH, and Ar is pyridinyl. In some aspects, X is O, and Ar is oxazolyl. In some aspects, X is NH, and Ar is oxazolyl. In some aspects, X is NH, and Ar is thiazolyl. In some aspects, X is O, and Ar is thiazolyl.

In some aspects, disclosed is a compound of formula (XXVII):

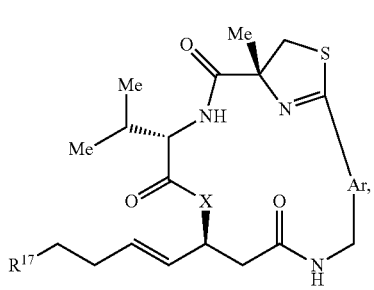
(XXVII)

wherein:
X is O or NH;
Ar is thiazolyl, pyridinyl, or oxazolyl;
$R^{17}$ is $R^2COS$, $R^3S$, or $R^4R^5N$, and
$R^2$, $R^3$, $R^4$, and $R^5$ independently are hydrogen, $C_{1-24}$ linear alkyl (e.g., methyl, ethyl, n-propyl, n-butyl, n-pentyl, n-hexyl, n-heptyl, n-octyl and so forth), $C_1$-$C_{24}$ linear alkyl substituted with one or more aryl or heteroaryl in any position (e.g., substituted with phenyl, pyridinyl, furanyl, pyrrolyl, thiophenyl, and so forth, or any combination thereof), $C_1$-$C_{24}$ branched alkyl (e.g., isopropyl, isobutyl, sec-butyl, tert-butyl, and so forth), $C_1$-$C_{24}$ branched alkyl substituted with one or more aryl or heteroaryl in any position (e.g., isopropyl substituted with phenyl, isobutyl substituted with pyridinyl, and so forth), $C_3$-$C_{24}$ cyclic alkyl (e.g., cylopropyl, cyclobutyl, cyclopentyl, cyclohexyl, methylcyclopropyl, and so forth), $C_3$-$C_{24}$ cyclic alkyl substituted with one or more aryl or heteroaryl in any position (e.g., cyclohexyl substituted with phenyl, and so forth), $C_1$-$C_{24}$ alkenyl, $C_1$-$C_{24}$ alkynyl, aryl (e.g., naphthalenyl, phenyl, pryridinyl, furanyl, pyrrolyl, thiophenyl, and so forth), heteroaryl (e.g., pryridinyl, furanyl, pyrrolyl, thiophenyl, and so forth), diphenyl methyl, triphenylmethyl, or any substituted version thereof. In some aspects, the compound of formula (XXVII) excludes compounds where $R^2$ is unsubstituted $C_7$ linear alkyl when $R^{17}$ is $R^2COS$ (i.e., a proviso where when $R^{17}$ is $R^2COS$ then $R^2$ is not unsubstituted $C_7$ linear alkyl).

Various aspects are contemplated herein, several of which are set forth in the paragraphs below. It is explicitly contemplated that any aspect or portion thereof can be combined to form an aspect.

Aspect 1: A method for preparing a compound of formula (I):

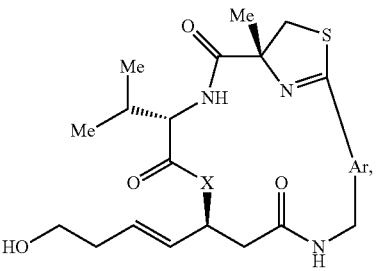
(I)

the method comprising reacting in one or more reactions:
a compound of formula (IV):

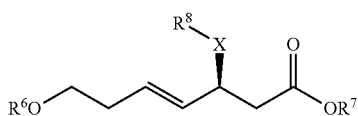
(IV)

a compound of formula (V):

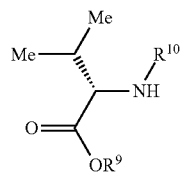
(V)

and a compound of formula (VI):

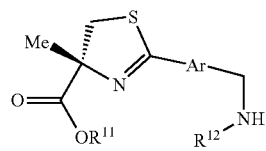
(VI)

wherein:
X is O or NH;
Ar is thiazolyl, pyridinyl, or oxazolyl;
$R^6$ is H or a suitable alcohol protecting group,
$R^8$, $R^{10}$, and $R^{12}$ independently are H, a suitable amine protecting group, or a chiral group,
$R^7$, $R^9$, and $R^{11}$ independently are H, an alkali metal ion, an alkaline earth metal ion, or a suitable carboxylic acid protecting group;
optionally wherein the suitable carboxylic acid protecting group is selected from $C_1$-$C_6$ linear or branched alkyl, $C_1$-$C_6$ linear or branched alkyl substituted with one or more aryl or heteroaryl in any position, or alkylsilyl;

optionally wherein the $C_1$-$C_6$ linear or branched alkyl, or the $C_1$-$C_6$ linear or branched alkyl substituted with one or more aryl or heteroaryl in any position, is selected from methyl, ethyl, propyl, isopropyl, allyl, butyl, 2-butyl, tert-butyl, benzyl, or substituted benzyl; and optionally wherein the alkylsilyl is 2-(trimethylsilyl)ethyl.

Aspect 2: A method for preparing a compound of formula (III):

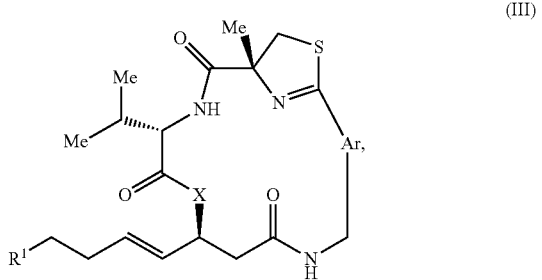

the method comprising:
reacting a compound of formula (I):

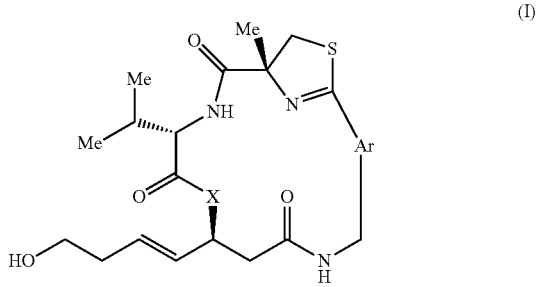

with an activating agent selected from $C_1$-$C_{20}$ linear or branched alkyl-sulfonyl halide, substituted alkyl-sulfonyl halide, arylsulfonyl halide, substituted arylsulfonyl halide, halo-phosphite (e.g., chlorophosphite), or a halogenating reagent, thereby forming a compound of formula (II):

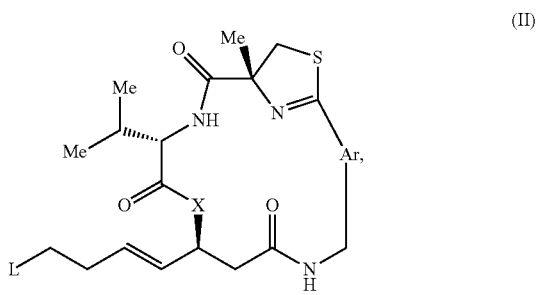

and reacting the compound of formula (II) with a nucleophile comprising an $R^1$ group, thereby forming the compound of formula (III);
wherein:
X is O or NH;
Ar is thiazolyl, pyridinyl, or oxazolyl;
$R^1$ is $R^2COS$, $R^3S$, or $R^4R^5N$;

$R^2$, $R^3$, $R^4$, and $R^5$ independently are hydrogen, $C_1$-$C_{24}$ linear alkyl, $C_1$-$C_{24}$ linear alkyl substituted with one or more aryl or heteroaryl in any position, $C_1$-$C_{24}$ branched alkyl, $C_1$-$C_{24}$ branched alkyl substituted with one or more aryl or heteroaryl in any position, $C_3$-$C_{24}$ cyclic alkyl, $C_3$-$C_{24}$ cyclic alkyl substituted with one or more aryl or heteroaryl in any position, $C_1$-$C_{24}$ alkenyl, $C_1$-$C_{24}$ alkynyl, aryl, heteroaryl, diphenyl methyl, triphenylmethyl, or any substituted version thereof; and L is a leaving group selected from $C_1$-$C_{24}$ linear or branched carbon sulfonate, substituted $C_1$-$C_{24}$ linear or branched sulfonate, arylsulfonate, substituted arylsulfonate, heteroarylsulfonate, substituted heteroarylsulfonate, phosphate, or halogen.

Aspect 3: A method for preparing a compound of formula (III):

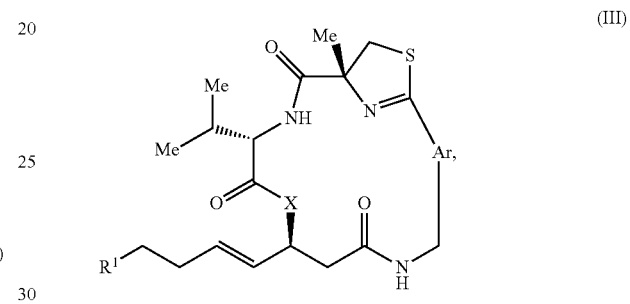

the method comprising:
reacting a compound of formula (II) with a nucleophile comprising an $R^1$ group:

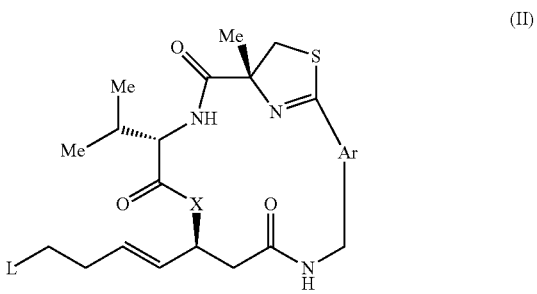

wherein:
X is O or NH;
Ar is thiazolyl, pyridinyl, or oxazolyl;
$R^1$ is $R^2COS$, $R^3S$, or $R^4R^5N$;
$R^2$, $R^3$, $R^4$, and $R^5$ independently are hydrogen, $C_1$-$C_{24}$ linear alkyl, $C_1$-$C_{24}$ linear alkyl substituted with one or more aryl or heteroaryl in any position, $C_1$-$C_{24}$ branched alkyl, $C_1$-$C_{24}$ branched alkyl substituted with one or more aryl or heteroaryl in any position, $C_3$-$C_{24}$ cyclic alkyl, $C_3$-$C_{24}$ cyclic alkyl substituted with one or more aryl or heteroaryl in any position, $C_1$-$C_{24}$ alkenyl, $C_1$-$C_{24}$ alkynyl, aryl, heteroaryl, diphenyl methyl, triphenylmethyl, or any substituted version thereof; and L is a leaving group selected from $C_1$-$C_{24}$ linear or branched carbon sulfonate, substituted $C_1$-$C_{24}$ linear or branched sulfonate, arylsulfonate, substituted arylsulfonate, heteroarylsulfonate, substituted heteroarylsulfonate, phosphate, or halogen.

Aspect 4: The method of aspect 3, or any preceding aspect, further comprising producing the compound of formula (II) from a compound of formula (IX):

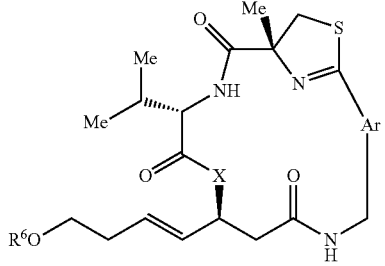
(IX)

by converting OR$^6$ of the compound of formula (IX) into the leaving group L;

wherein R$^6$ is H or a suitable alcohol protecting group.

Aspect 5: The method of aspect 4, or any preceding aspect, wherein converting OR$^6$ into the leaving group L comprises:

when R$^6$ is the suitable alcohol protecting group, deprotecting the suitable alcohol protecting group to provide the compound of formula (IX) where R$^6$ is H; and reacting the compound of formula (IX) where R$^6$ is H with an activating agent selected from C$_1$-C$_{20}$ linear or branched alkyl-sulfonyl halide, substituted alkyl-sulfonyl halide, arylsulfonyl halide, substituted arylsulfonyl halide, halo-phosphite (e.g., chlorophosphite), or a halogenating reagent.

Aspect 6: The method of aspect 4 or aspect 5, or any preceding aspect, wherein the compound of formula (IX) is a compound of formula (I):

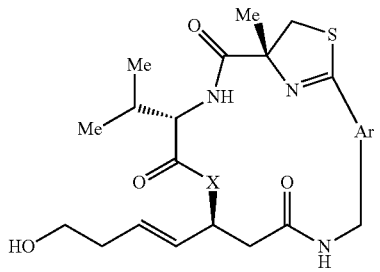
(I)

and the method comprises reacting the compound of formula (I) with an activating agent selected from C$_1$-C$_{20}$ linear or branched alkyl-sulfonyl halide, substituted alkyl-sulfonyl halide, arylsulfonyl halide, substituted arylsulfonyl halide, halo-phosphite (e.g., chlorophosphite), or a halogenating reagent, thereby forming the compound of formula (II).

Aspect 7: The method of any preceding aspect, wherein the compound of formula (I) or the compound of formula (IX) is a compound of formula (I-a), (I-b), or (I-c):

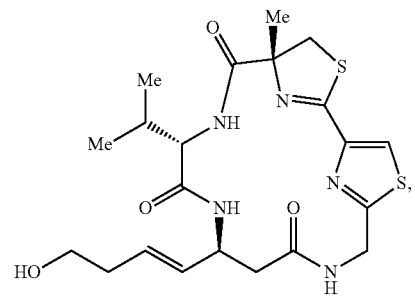
(I-a)

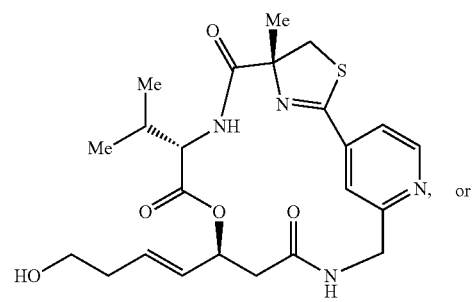
(I-b)

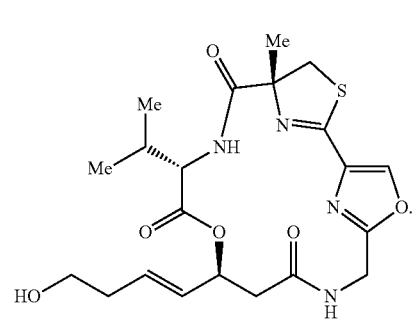
(I-c)

Aspect 8: The method of any preceding aspect, wherein L is OMs, OTs, OTf, 2,2,2-trifluoroethanesulfonate, n-octanesulfonate, benzenesulfonate, OP(=O)(OMe)$_2$, OP(=O)(OEt)$_2$, OP(=O)(OPh)$_2$, I, Br, Cl or F.

Aspect 9: The method of any preceding aspect, wherein Ar is:

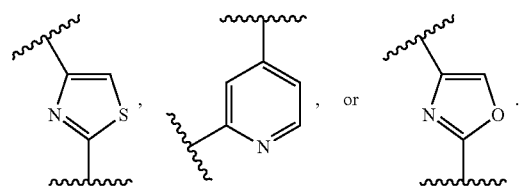 [SMILES: *c1csc(*)n1 ; *c1ccnc(*)c1 ; *c1coc(*)n1]

Aspect 10: The method of any preceding aspect, wherein the nucleophile is thiooctanoic acid, such that the compound of formula (III) is a compound of formula (XXV):

(XXV)

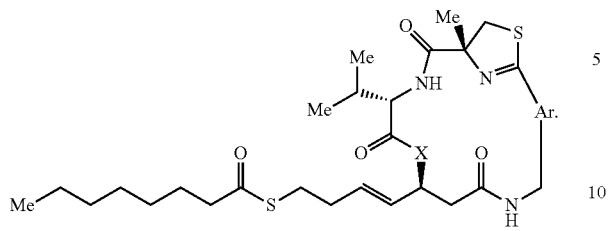

Aspect 11: The method of aspect 10, or any preceding aspect, wherein X is NH and Ar is:

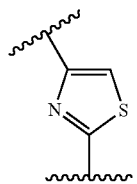 [SMILES: *c1csc(*)n1]

such that the compound of formula (III) is a compound of formula (1):

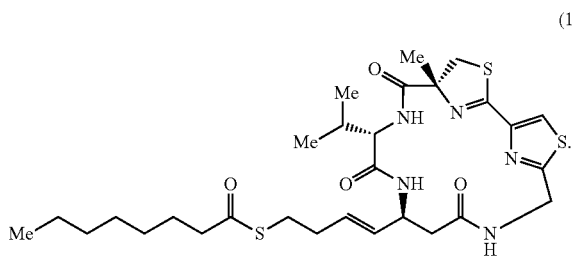
(1)

Aspect 12: The method of aspect 10, or any preceding aspect, wherein X is O and Ar is:

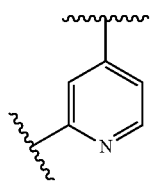 [SMILES: *c1ccnc(*)c1]

such that the compound of formula (III) is a compound of formula (2):

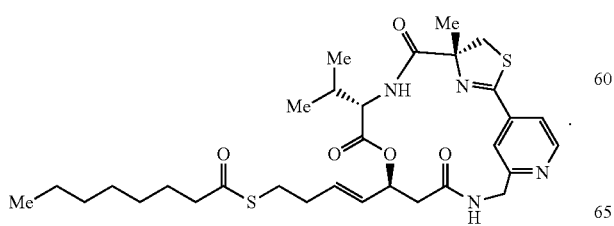
(2)

Aspect 13: The method of aspect 10, or any preceding aspect, wherein X is O and Ar is:

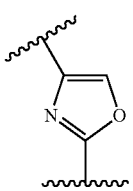 [SMILES: *c1coc(*)n1]

such that the compound of formula (III) is a compound of formula (3):

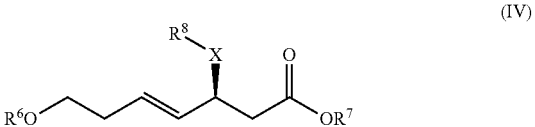
(3)

Aspect 14: The method of any one of aspects 2 or 4-13, or any preceding aspect, wherein the method further comprises producing the compound of formula (I) or the compound of formula (IX) from one or more reactions comprising:

a compound of formula (IV):

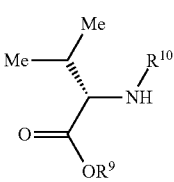
(IV)

a compound of formula (V):

(V)

and a compound of formula (VI):

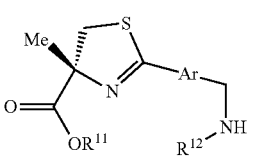
(VI)

wherein:
R$^6$ is H or a suitable alcohol protecting group,
R$^8$, R$^{10}$, and R$^{12}$ independently are H, a suitable amine protecting group, or a chiral group,
R$^7$, R$^9$, and R$^{11}$ independently are H, an alkali metal ion, an alkaline earth metal ion, or a suitable carboxylic acid protecting group;
optionally wherein the suitable carboxylic acid protecting group is selected from C$_1$-C$_6$ linear or branched alkyl, C$_1$-C$_6$ linear or branched alkyl substituted with one or more aryl or heteroaryl in any position, or alkylsilyl;
optionally wherein the C$_1$-C$_6$ linear or branched alkyl, or the C$_1$-C$_6$ linear or branched alkyl substituted with one or more aryl or heteroaryl in any position, is selected from methyl, ethyl, propyl, isopropyl, allyl, butyl, 2-butyl, tert-butyl, benzyl, or substituted benzyl; and
optionally wherein the alkylsilyl is 2-(trimethylsilyl)ethyl.

Aspect 15: The method of aspect 1 or aspect 14, or any preceding aspect, wherein:
the compound of formula (IV) is reacted with the compound of formula (V) via condensation to form a compound of formula (VII):

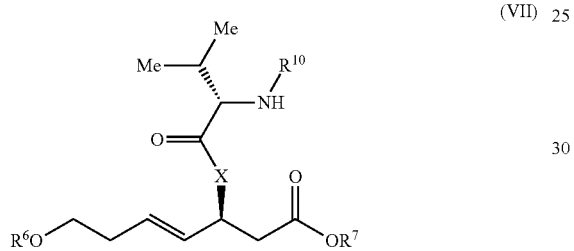

(VII)

the compound of formula (VII) is reacted with the compound of formula (VI) via amidation to form a compound of formula (VIII):

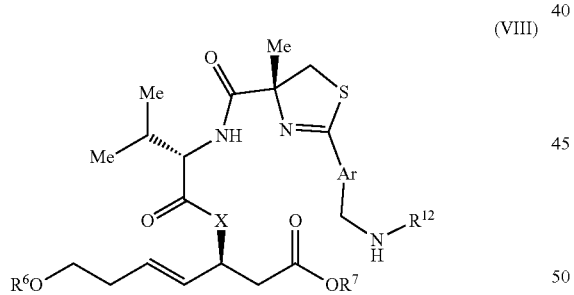

(VIII)

and the compound of formula (VIII) is reacted by amidating ring closure to form the compound of formula (IX) or the compound of formula (I) where R$^6$ is H.

Aspect 16: The method of aspect 15, or any preceding aspect, wherein:
R$^6$ is H or a suitable alcohol protecting group;
in reacting the compound of formula (IV) with the compound of formula (V): R$^8$ is H, and when X is N, the N is neutral or positively charged; R$^7$ is a suitable carboxylic acid protecting group; R$^{10}$ is a suitable amine protecting group; and R$^9$ is H, an alkali metal ion, or an alkaline earth metal ion;
in reacting the compound of formula (VI) with the compound of formula (VII): R$^7$ is a suitable carboxylic acid protecting group; R$^{10}$ is H, and optionally R$^{10}$ is attached to a positively charged nitrogen atom; R$^{11}$ is H, an alkali metal ion, or an alkaline earth metal ion; and R$^{12}$ is a suitable amine protecting group; and
in reacting the compound of formula (VIII) by amidating ring closure: R$^8$ is H, an alkali metal ion, or an alkaline earth metal ion, and when X is N, the N is neutral or positively charged; and R$^{12}$ is H, and optionally R$^{12}$ is attached to a positively charged nitrogen atom.

Aspect 17: The method of any one of aspects 1 or 14-16, or any preceding aspect, wherein X is NH, and the method further comprises producing the compound of formula (IV) by:
reacting via imine formation a compound of formula (X):

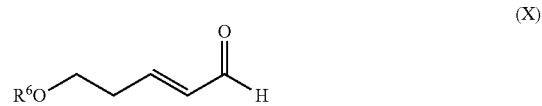

(X)

with a chiral auxiliary of formula (XI):

(XI)

to form a compound of formula (XII):

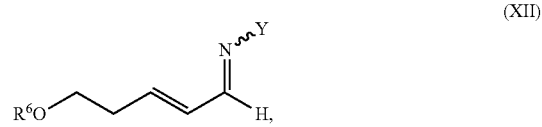

(XII)

reacting the compound of formula (XII) via nucleophilic addition with a compound of formula (XIII):

(XIII)

to form the compound of formula (IV) where X is NH and R$^8$ is chiral group Y:

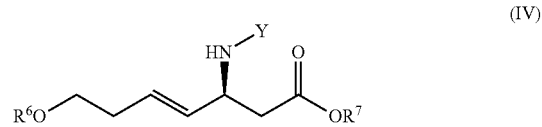

(IV)

and cleaving the N—Y bond to form the compound of formula (IV) where R$^8$ is H, and when X is N, the N is neutral or positively charged,
wherein:
Y is a chiral group sufficient to effect a diastereoselective nucleophilic addition of the compound of formula (XIII) to the compound formula (XII) to form the compound of formula (IV) as a majority product where R$^8$ is chiral group Y,
R$^6$ is a suitable alcohol protecting group,
R$^7$ is a suitable carboxylic acid protecting group;
optionally wherein the carboxylic acid protecting group is selected from C$_1$-C$_6$ linear or branched alkyl, C$_1$-C$_6$ linear or branched alkyl substituted with one or more aryl or heteroaryl in any position, or alkylsilyl;

optionally wherein the $C_1$-$C_6$ linear or branched alkyl, or the $C_1$-$C_6$ linear or branched alkyl substituted with one or more aryl or heteroaryl in any position, is selected from methyl, ethyl, propyl, isopropyl, allyl, butyl, 2-butyl, tert-butyl, benzyl, or substituted benzyl; and optionally wherein the alkylsilyl is 2-(trimethylsilyl)ethyl; and $R^{13}$ is H, a halide, or a metal comprising Li, Na, K, ZnBr, ZnCl, CuCl, CuBr, CuI, Cu, or any combination thereof.

Aspect 18: The method of aspect 17, or any preceding aspect, wherein the chiral auxiliary of formula (XI) is:

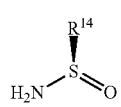

(XI)

wherein $R^{14}$ is tert-butyl, p-tolyl, alkyl, an aromatic group, or any substituted versions thereof.

Aspect 19: The method of aspect 18, or any preceding aspect, wherein $R^{14}$ is tert-butyl, such that the compound of formula (XI) is (R)-tert-butanesulfinamide.

Aspect 20: A compound of formula (XXVI):

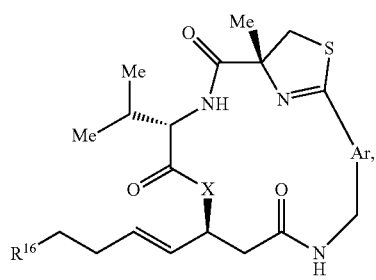

(XXVI)

wherein:
X is O or NH;
Ar is thiazolyl, pyridinyl, or oxazolyl;
$R^{16}$ is OH, $OR^6$, or L;
$R^6$ is a suitable alcohol protecting group; and
L is a leaving group selected from $C_1$-$C_{24}$ linear or branched carbon sulfonate, substituted $C_1$-$C_{24}$ linear or branched sulfonate, arylsulfonate, substituted arylsulfonate, heteroarylsulfonate, substituted heteroarylsulfonate, phosphate, or halogen.

Aspect 21: The compound of aspect 20, or any preceding aspect, wherein the compound of formula (XXVI) is a compound of formula (I-a), (I-b), or (I-c):

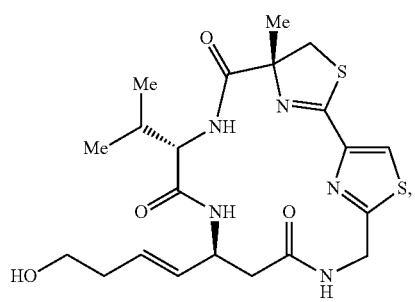

(I-a)

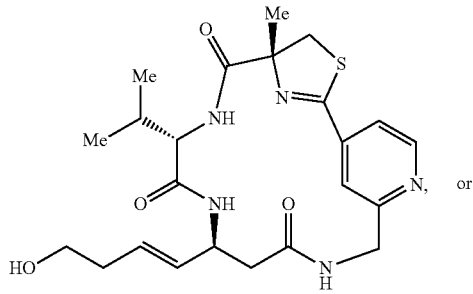

(I-b)

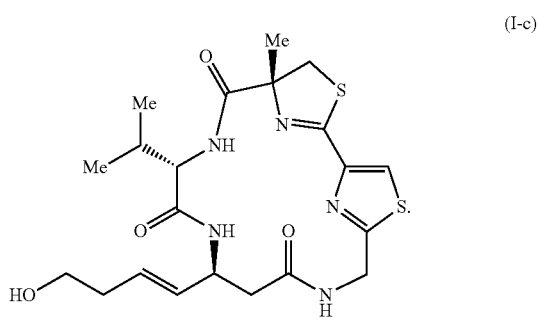

(I-c)

Aspect 22: The compound of aspect 20, or any preceding aspect, wherein $R^{16}$ is OH.

Aspect 23: The compound of aspect 20, or any preceding aspect, wherein $R^{16}$ is L.

Aspect 24: The compound of aspect 20, or any preceding aspect, wherein $R^{16}$ is $OR^6$.

Aspect 25: The compound of any one of aspects 20-24, or any preceding aspect, wherein: X is O; and Ar is pyridinyl.

Aspect 26: The compound of any one of aspects 20-24, or any preceding aspect, wherein: X is O; and Ar is oxazolyl.

Aspect 27: The compound of any one of aspects 20-24, or any preceding aspect, wherein: X is NH; and Ar is thiazolyl.

EXAMPLES

General Methods. Unless otherwise noted, all materials were obtained from commercial sources and used without purification. All reactions requiring anhydrous conditions were performed under a positive pressure of argon using flame-dried glassware. Dichloromethane, tetrahydrofuran, methanol, triethylamine, and acetonitrile were degassed with argon and dried through a solvent purification system (J. C. Meyer of Glass Contour). Flash chromatography was performed on Merck silica gel Kieselgel 60 (230-400 mesh) from EM science with the indicated solvent. $^1$H NMR and $^{13}$C NMR spectra were recorded on Varian 400 MHZ spectrometers unless indicated otherwise. Mass spectra were obtained on Agilent 6224 TOF. Optical rotations were recorded at 24° C. on an Autopol III Automatic Polarimeter (Rudolph Research, Fairfield, NJ). X-ray diffraction (XRD) was recorded on a Brucker D8 Discover DaVinci.

TABLE 1

HDAC Inhibition. Table 1 depicts in vitro histone deacetylase (HDAC) inhibition by thiol-macrocycle and hydroxy-macrocycle, in which HDAC inhibition is shown as $IC_{50}$ (M).

| HDAC Class | Class 1 | | | |
|---|---|---|---|---|
| HDAC Isoform | 1 | 2 | 3 | 8 |
| [thiol-macrocycle structure] | 4.42E−09 | 8.46E−09 | 2.49E−09 | 8.58E−07 |
| [hydroxy-macrocycle structure] (10) | >1.00E−02 | >1.00E−02 | >1.00E−02 | >1.00E−02 |

| HDAC Class | Class 2a | | | | Class 2b | | Class 4 |
|---|---|---|---|---|---|---|---|
| HDAC Isoform | 4 | 5 | 7 | 9 | 6 | 10 | 11 |
| [thiol-macrocycle structure] | 1.00E−03[1] | 1.79E−04 | 1.00E−03[1] | 1.00E−03[1] | 1.38E−07 | n/a | 1.61E−04 |

TABLE 1-continued

HDAC Inhibition. Table 1 depicts in vitro histone deacetylase (HDAC) inhibition by thiol-macrocycle and hydroxy-macrocycle, in which HDAC inhibition is shown as IC$_{50}$ (M).

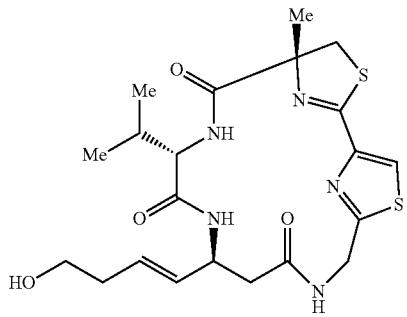 [SMILES: CC(C)[C@@H]1NC(=O)[C@]2(C)CSC(=N2)c2csc(n2)CNC(=O)C[C@@H](/C=C/CCS)NC1=O]

| | >1.00E−02 | >1.00E−02 | >1.00E−02 | >1.00E−02 | >1.00E−02 | n/a | >1.00E−02 |

(10)

HDAC Inhibition as IC$_{50}$ (M)
[1]-Estimates of IC$_{50}$ values

Figure 10:
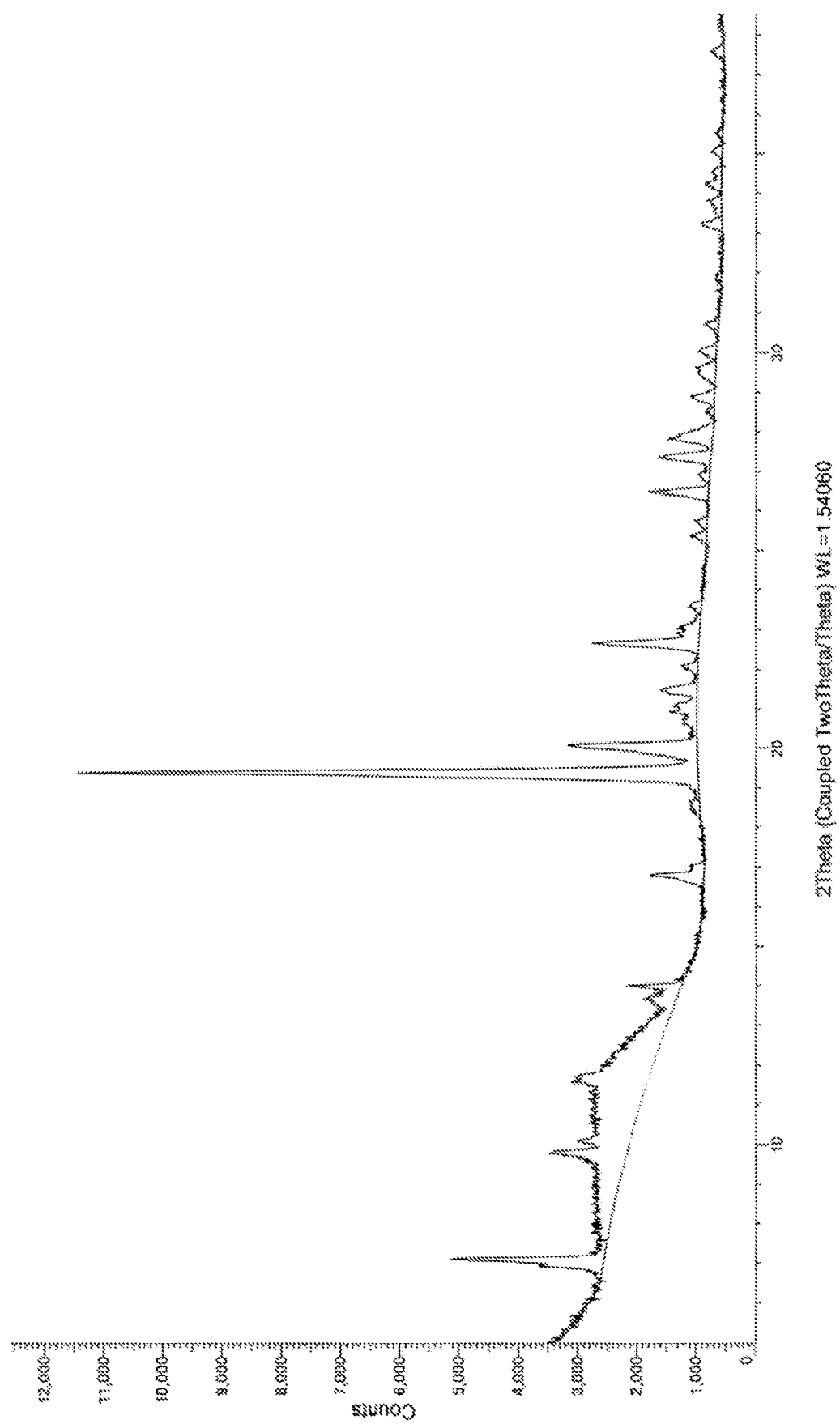
FIG. 10 is an XRD of compound 10 (i.e., the compound of formula (I-a)).

X-ray Diffraction. FIG. 10 is an XRD of compound 10 (i.e., compound of formula (I-a)).

Synthesis of Octanethioic S-acid. To the solution of thioacetamide (4.38 g, 58.3 mmol) in anhydrous toluene (75 mL) was added octanoyl chloride (10.0 mL, 58.3 mmol). The reaction mixture was stirred at 30° C. for 4 h. Then the reaction was cooled to 0° C. followed by addition of 10% aqueous NaOH (20 mL). The biphasic mixture was stirred at room temperature for 30 min and was acidified with aqueous 1M KHSO$_4$ to the pH 2-3. The acidified solution was extracted with ethyl acetate. The combined organic extracts were dried over anhydrous MgSO$_4$ and evaporated in vacuo. The crude product was filtered through silica to give thio-octanoic acid (7.30 g, 78% yield).

(E)-5-((tert-Butyldiphenylsilyl)oxy)pent-2-en-1-ol (34). To a neat mixture of 3-butyn-1-ol (10.0 g, 143 mmol) and imidazole (10.2 g, 171 mmol), tert-butyldiphenylchlorosilane (44.5 mL, 150 mmol) was added dropwise. The reaction mixture was stirred for 3.5 h. The precipitates were filtered and rinsed with diethyl ether. The combined organic extracts were dried over anhydrous Na$_2$SO$_4$. Evaporation of solvent in vacuo gave the crude (but-3-yn-1-yloxy)(tert-butyl)diphenylsilane, which was directly used without further purification.

To a solution of this crude product in anhydrous THF (600 mL) at −78° C., a solution of n-butyllithium (1.6 M, 98.1 mL, 157 mmol) in hexanes was added dropwise. The reaction mixture was stirred at −78° C. for 1 h, warmed to room temperature over 2.5 h, and then cooled again to −78° C. To the reaction mixture, paraformaldehyde (5.57 g, 185 mmol) was added in one portion and the resulting suspension was slowly warmed to room temperature and stirred overnight. The mixture was concentrated in vacuo and then partitioned between diethyl ether and water. The phases were separated, and the aqueous phase was further extracted with diethyl ether. The combined organic extracts were dried over anhydrous Na$_2$SO$_4$ and concentrated in vacuo to give crude propargylic alcohol, which was directly used without further purification.

To a solution of crude propargylic alcohol in anhydrous diethyl ether (500 mL) at 0° C., Red-Al (70% in toluene) (45.6 mL, 152 mmol) was slowly added and the reaction mixture was stirred for 2 h at 0° C. The reaction mixture was quenched carefully with a wet paste of Na$_2$SO$_4$ until the appearance of colorless solid. The aluminum salts were filtered off, and the salts were washed repeatedly with hot THF. The combined filtrates were dried over anhydrous Na$_2$SO$_4$ and concentrated in vacuo. The residue was then purified by column chromatography on silica gel to give the trans-allylic alcohol 34 as a colorless oil (29.1 g, 60% yield over 3 steps). $^1$H NMR (400 MHZ, CDCl$_3$) δ 7.73-7.64 (m, 4H), 7.48-7.35 (m, 6H), 5.74-5.62 (m, 2H), 4.07 (d, J=3.5 Hz, 2H), 3.73 (t, J=6.6 Hz, 2H),), 2.32 (q, J=6.1 Hz, 2H), 1.44 (bs, 1H), 1.07 (s, 9H); $^{13}$C NMR (101 MHZ, CDCl$_3$) δ 135.7, 134.1, 131.1, 129.7, 129.6, 127.7, 63.8, 63.6, 35.7, 27.0, 19.3.

(R)—N-((1E,2E)-5-((tert-Butyldiphenylsilyl)oxy)pent-2-en-1-ylidene)-2-methylpropane-2-sulfinamide (29). To a solution of DMSO (12.1 mL, 171 mmol) in anhydrous CH$_2$Cl$_2$ (200 mL) was added oxalyl chloride (10.8 mL, 128 mmol) over 15 min at −78° C. After stirring for 30 min at −78° C., trans-allylic alcohol 4 (29.1 g, 85.5 mmol) in anhydrous CH$_2$Cl$_2$ (500 mL) was added dropwise over 30 min and stirred at −78° C. for an additional 2.5 h. Then, triethylamine (35.7 mL, 256 mmol) was added dropwise and stirred at −78° C. for an additional hour and allowed to slowly warm to room temperature. After stirring at room temperature for 3 h, the reaction mixture was quenched by addition of water. The organic layer was separated and the aqueous layer was extracted with CH$_2$Cl$_2$. The combined organic extracts were dried over anhydrous Na$_2$SO$_4$ and concentrated in vacuo. The crude aldehyde (27) is immediately subjected to the next reaction without further purification To a solution of this crude aldehyde in anhydrous THF (500 mL) was added Ti(O$^i$Pr)$_4$ (40.5 mL, 137 mmol) at room temperature and was stirred for 10 min. To this, (R)-tert-butanesulfinamide (11.4 g, 94.0 mmol) was added and the reaction stirred at room temperature overnight. The reaction was quenched with saturated aqueous NaCl. The crude mixture was filtered through Celite, and the filter cake was washed with ethyl acetate. The filtrate was then dried over Na$_2$SO$_4$, concentrated in vacuo, and the crude product was purified by column chromatography on silica gel (eluted by 15-85% ethyl acetate in hexanes) to give imine 29 (26.2 g, 71%). $^1$H NMR (400 MHZ, CDCl$_3$) δ 8.18 (d, J=8.7 Hz, 1H), 7.65 (d, J=7.7 Hz, 4H), 7.41 (dq, J=14.0, 6.9 Hz, 6H), 6.60-6.42 (m, 2H), 3.80 (td, J=6.2, 2.1 Hz, 2H),), 2.51 (q, J=6.2 Hz, 2H), 1.20 (s, 9H), 1.05 (s, 9H); $^{13}$C NMR (101 MHZ, CDCl$_3$) δ 164.1, 148.3, 135.7, 133.7, 130.5, 129.9, 127.9, 62.4, 57.3, 36.4, 27.0, 22.6, 19.3; [α]$^{25}_D$: −161.6 (c=1.64, CHCl$_3$).

Methyl (S,E)-7-((tert-butyldiphenylsilyl)oxy)-3-(((R)-tert-butylsulfinyl)amino)hept-4-enoate (31). The oven dried flask was charged with Zn dust (34.0 g, 520 mmol) and CuCl (5.20 g, 52.0 mmol). The two solids were mixed under a slow stream of nitrogen while the flask was flame dried. The flask was allowed to cool to room temperature and anhydrous THF (120 mL) was added to produce a dark slurry. The resulting reaction mixture was heated to reflux and stirred vigorously for 30 min. The heating bath was then removed, and while maintaining vigorous stirring, methyl bromoacetate (30) (19.7 mL, 208 mmol) in anhydrous THF (40 mL) was added slowly via an addition funnel until reflux was re-initiated. The addition was continued at a rate that maintained a controllable reflux. The reaction mixture was stirred for an additional 30 min at room temperature after the addition was complete. Then the mixture was heated to 50° C. for 30 min. The reaction mixture was cooled to 0° C. To the reaction mixture was dropwisely added a solution of tert-butanesulfinyl imine 29 (23.0 g, 52.0 mmol) in anhydrous THF (120 mL) via an additional funnel at 0° C. The reaction mixture was stirred for an additional 18 h at 0° C. The reaction mixture was filtered through a pad of Celite, which was washed with diethyl ether. The filtrate was washed with saturated aqueous NaHCO$_3$, saturated aqueous NaCl. The organic layer was dried over Na$_2$SO$_4$ and concentrated in vacuo. The crude product was purified by column chromatography on silica gel (eluted by 50% ethyl acetate in hexanes) to give methyl ester 31 (20.1 g, 75%). $^1$H NMR (400 MHZ, CDCl$_3$) δ 7.63-7.70 (m, 4H), 7.44-7.36 (m, 6H), 5.74 (dt, J=15.1, 6.9 Hz, 1H), 5.42 (ddt, J=15.4, 7.0, 1.4 Hz, 1H), 4.25 (d, J=5.7 Hz, 1H), 4.15 (p, J=6.2, 1H), 3.71-3.65 (m, 5H), 2.69 (dd, J=15.8, 4.9 Hz, 1H), 2.60 (dd, J=15.9, 7.1 Hz, 1H), 2.36-2.23 (m, 2H), 1.20 (s, 9H), 1.04 (s, 9H); $^{13}$C NMR (101 MHZ, CDCl$_3$) δ 172.0, 135.6, 135.6, 131.2, 130.4, 129.7, 127.7, 63.4, 55.6, 54.1, 51.9, 40.9, 36.0, 37.0, 22.8, 19.3; HRMS (ESI) m/z calcd for C$_{28}$H$_{41}$NNaO$_4$SSi [M+Na]$^+$ 538.2423, found 538.2421; [α]$^{25}_D$: −45.8 (c=0.80, CHCl$_3$).

Methyl (S,E)-3-((S)-2-((tert-butoxycarbonyl)amino)-3-methylbutanamido)-7-((tert-butyldiphenylsilyl)oxy)hept-4-enoate (6). To a solution of 31 (5.5 g, 10.7 mmol) in anhydrous dioxane:ether (1:1, 100 mL), 1 N HCl in Et$_2$O (11 mL, 10.7 mmol) was added. The solution was filtered through a plug of basic alumina, and the solution was concentrated in vacuo. In a separate flask, PyBOP (8.32 g, 16.0 mmol) and DIPEA (5.6 mL, 32.0 mmol) were added to a solution of N-Boc-L-valine (5) (2.78 g, 12.8 mmol) in anhydrous CH$_2$Cl$_2$ (75 mL). The mixture was stirred for 5 min at room temperature before being cooled down to 0° C. The HCl salt form of the deprotected amine was dissolved in anhydrous CH$_2$Cl$_2$ (25 mL) and the solution was added dropwise to the activated acid at 0° C. under argon atmosphere. The mixture was warmed to room temperature and stirred for 8 h. The solvent was removed in vacuo and the crude reaction mixture was purified by column chromatography on silica gel (eluted by 30% ethyl acetate in hexanes) to yield di-peptide 6 (4.1 g, 63% yield over two steps). $^1$H NMR (400 MHz, CDCl$_3$) δ 7.71-7.60 (m, 4H), 7.49-7.31 (m, 6H), 6.53 (d, J=8.4 Hz, 1H), 5.73-5.60 (m, 1H), 5.55-5.46 (m, 1H), 5.05 (d, J=5.4 Hz, 1H), 4.73-4.81 (m, 1H), 3.91-3.83 (m, 1H), 3.68-3.62 (m, 2H), 3.64 (s, 3H), 2.59 (d, J=5.4 Hz, 2H), 2.24-2.29 (q, J=6.7, 2H), 2.04-2.14 (m, 1H), 2.16-2.05 (m, 1H), 1.43 (s, 9H), 1.03 (s, 9H), 0.93 (d, J=6.8 Hz, 3H), 0.87 (d, J=6.8 Hz, 3H); $^{13}$C NMR (101 MHZ, CDCl$_3$) δ 171.9, 170.8, 135.7, 134.1, 133.9, 130.1, 129.8, 129.5, 127.8, 63.5, 51.9, 47.6, 38.9, 35.7, 31.2, 28.4, 27.0, 19.4, 19.3, 17.7; [α]$^{25}_D$: −5.3 (c=0.7, CHCl$_3$).

Methyl (S,E)-3-((S)-2-((R)-2'-(((tert-butoxycarbonyl)amino)methyl)-4-methyl-4,5-dihydro-[2,4'-bithiazole]-4-carboxamido)-3-methylbutanamido)-7-((tert-butyldiphenylsilyl)oxy)hept-4-enoate (8). Compound 6 (1.93 g, 3.20 mmol) was dissolved in anhydrous CH$_2$Cl$_2$ (50 mL) and treated with TFA (7 mL) at 0° C. The resulting solution was warmed to room temperature and stirred for 2 h. The solvent was evaporated in vacuo. The crude TFA salt was then dissolved in toluene, concentrated in vacuo, and dried on high vacuum to remove the residual TFA. In a separate flask, PyBOP (2.48 g, 4.76 mmol) and DIPEA (1.66 mL, 9.52 mmol) was added to a solution of 7 (1.36 g, 3.80 mmol) in anhydrous CH$_2$Cl$_2$ (30 mL). This stirred for 5 min at room temperature before being cooled down to 0° C. The crude TFA-salt was dissolved in anhydrous CH$_2$Cl$_2$ (15 mL) and was added dropwise to the solution of the activated acid. The reaction mixture was stirred at room temperature for 2 h. The mixture was dried in vacuo and the crude residue was immediately purified via column chromatography on silica gel (eluted by 40%-50% ethyl acetate in hexanes) to yield 8 (2.2 g, 2.58 mmol, 81% yield). $^1$H NMR (400 MHZ, CDCl$_3$) δ 7.96 (s, 1H), 7.64 (d, J=8.8 Hz, 4H), 7.46-7.33 (m, 6H), 6.62 (d, J=8.7 Hz, 1H), 5.73-5.61 (m, 1H), 5.51 (dd, J=15.5, 6.3 Hz, 1H), 5.29 (s, 1H), 4.86-4.74 (m, 1H), 4.63 (d, J=6.3 Hz, 2H), 4.17 (dd, J=8.8, 6.3 Hz, 1H), 3.76 (d, J=11.6 Hz, 1H), 3.69-3.61 (m, 3H) 3.65 (s, 3H), 3.33 (d, J=11.6 Hz, 1H), 2.60 (d, J=5.3 Hz, 2H), 2.26 (q, J=6.6 Hz, 2H), 2.18-2.07 (m, 1H), 1.58 (s, 3H), 1.47 (s, 9H), 1.03 (s, 9H), 0.85 (dd, J=15.5, 6.8 Hz, 3H), 0.81 (d, J=6.8 Hz, 3H); $^{13}$C NMR (101 MHZ, CDCl$_3$) δ 174.8, 171.8, 169.9, 169.8, 163.2, 155.7, 135.6, 134.0, 133.9, 130.1, 129.7, 129.5, 127.7, 85.1, 80.5, 63.4, 58.6, 51.8, 47.6, 42.4, 41.6, 38.8, 35.7, 30.8, 28.4, 26.9, 24.8, 19.4, 19.3, 17.8; [α]$^{25}_D$: −39.5 (c=1.2, CHCl$_3$).

(12Z,22Z,24R,5S,8S)-8-((E)-4-((tert-butyldiphenylsilyl)oxy)but-1-en-1-yl)-5-isopropyl-24-methyl-24,25-dihydro-4,7,11-triaza-1(4,2),2(2,4)-dithiazolacyclododecaphane-3,6,10-trione (9). To a solution of methyl ester 8 (2.0 g, 2.40 mmol) in a THF:water (50 mL, 2:1) was added LiOH·H$_2$O (0.12 g, 4.6 mmol). The reaction was stirred for 30 min, The reaction mixture was cooled to 0° C. and acidified to pH ~3-4 by dropwise addition of 1M aqueous KHSO$_4$. The solution was diluted with water and extracted with CH$_2$Cl$_2$. The combined organic extracts were dried over Na$_2$SO$_4$, and concentrated in vacuo to provide the corresponding acid, which was used without further purification. To a solution of the acid in anhydrous CH$_2$Cl$_2$ (100 mL) at 0° C. was added TFA (7 mL). The mixture was stirred at room temperature for 2 h. The solvent was removed in vacuo. The crude salt was then dissolved in toluene, concentrated in vacuo, and dried on high vacuum to remove residual TFA. To a solution of HATU (2.70 g, 7.10 mmol), HOBt·H$_2$O (0.650 g, 4.80 mmol) and DIPEA (2.4 mL, 14.2 mmol) in anhydrous CH$_3$CN (1850 mL) at 0° C. was added a solution the TFA salt in anhydrous CH$_3$CN (50 mL) dropwise over 20 h via a syringe pump at 0° C. After complete addition, the resulting mixture was stirred at 0° C. for 8 h and room temperature for an additional 15 h. The solvent of the reaction mixture was evaporated in vacuo. The resulting residue was dissolved in CH$_2$Cl$_2$ (50 mL), filtered through a Celite pad and dried over anhydrous MgSO$_4$. The solvent was evaporated in vacuo, and the resulting residue was purified by chromatography column on silica gel (eluted by 3% methanol in CH$_2$Cl$_2$) to give macrocyclic core 9 (1.08 g, with 64% yield). $^1$H NMR (400 MHZ, CDCl$_3$) δ 7.78 (s, 1H), 7.64 (d, J=6.6 Hz, 4H), 7.43-7.34 (m, 6H), 6.50 (d, J=10.7 Hz, 1H), 6.38 (d, J=8.9 Hz 1H), 6.19 (d, J=8.2 Hz 1H), 5.75-5.63 (m, 1H), 5.50 (dd, J=15.5, 5.9 Hz, 1H), 5.24 (dd, J=17.6, 8.9 Hz, 1H), 4.98 (s, 1H), 4.53 (dd, J=10.7, 3.2 Hz, 1H), 4.24 (dd, J=17.7, 3.2 Hz, 1H), 3.90 (d, J=11.6 Hz, 1H), 3.70-3.62 (m, 2H), 3.37 (d, J=11.6 Hz, 1H), 2.72 (dd, J=15.4, 4.0 Hz, 1H) 2.55-2.20 (m, 2H), 2.27 (q, J=6.6 Hz, 2H), 1.86 (s, 3H), 1.04 (s, 9H), 0.77 (d, J=6.9 Hz, 3H), 0.36 (d, J=6.8 Hz, 3H);$^{13}$C NMR (101 MHZ, CDCl$_3$) δ 173.8, 170.0, 169.9, 168.7, 165.9, 135.7, 134.0, 130.9, 129.8, 128.5, 127.8, 124.2, 84.7, 63.5, 58.3, 48.1, 43.9, 40.9, 40.8, 35.7, 32.1, 27.0, 24.3, 19.6, 19.4, 15.3; HRMS (ESI) m/z calcd for C$_{37}$H$_{47}$N$_5$NaO$_4$S$_2$Si [M+Na]$^+$ 740.2736, found 740.2736; $[α]^{25}_D$: +23.4 (c=0.29, CHCl$_3$).

(12Z,22Z,24R,5S,8S)-8-((E)-4-hydroxybut-1-en-1-yl)-5-isopropyl-24-methyl-24,25-dihydro-4,7,11-triaza-1(4,2), 2(2,4)-dithiazolacyclododecaphane-3,6,10-trione (10). To a solution of compound 9 (1.00 g, 1.40 mmol) in CH$_2$Cl$_2$: methanol (1:1, 60 mL) at 0° C. was added p-toluenesulfonic acid monohydrate (148 mg). The reaction mixture was stirred for 12 h at room temperature. The reaction was quenched with solid NaHCO$_3$ (176 mg) and was filtered through a Celite pad, which was washed with CH$_2$Cl$_2$: methanol (1:1) followed by evaporation in vacuo. The crude residue was purified over column chromatography on silica gel (eluted by 5% methanol in CH$_2$Cl$_2$) to afford compound 10 as a colorless solid (0.600 g, 90% yield). $^1$H NMR (400 MHZ, CDCl$_3$:CD$_3$OD=4:1) δ 7.76 (s, 1H), 7.40-7.34 (m, 1H), 6.51 (d, J=10.8 Hz, 1H), 5.59-5.50 (m, 1H), 5.40 (dd, J=15.5, 15.7 Hz, 1H), 5.22 (d, J=17.8 Hz, 1H), 4.79-4.74 (m, 1H), 4.50 (d, J=10.8 Hz, 1H), 4.22 (d, J=17.8 Hz, 1H), 3.87 (d, J=11.8 Hz, 1H), 3.56-3.49 (m, 2H), 3.30-3.41 (m, 1H), 2.92-2.96 (m, 1H), 2.57-2.48 (m, 2H), 2.40-2.32 (m, 1H), 2.20 (q, J=7.2, 6.8 Hz, 2H), 1.85 (s, 3H), 1.40-1.30 (m, 1H), 0.66 (d, J=6.9 Hz, 3H), 0.18 (d, J=6.8 Hz, 3H); $^{13}$C NMR (101 MHZ, CDCl$_3$:CD$_3$OD=4:1) δ 174.0, 170.8, 170.7, 168.5, 167.5, 146.6, 131.5, 128.2, 124.5, 84.0, 61.2, 58.3, 49.1, 43.6, 40.7, 40.5, 35.6, 32.3, 24.0, 19.4, 15.0; HRMS (ESI) m/z calcd. for C$_{21}$H$_{29}$N$_5$NaO$_4$S$_2$ [M+Na]$^+$ 502.1559, found 502.1568; $[α]^{25}_D$: +79.7 (c=0.4, CH$_3$OH).

S—((E)-4-((12Z,22Z,24R,5S,8S)-5-isopropyl-24-methyl-3,6,10-trioxo-24,25-dihydro-4,7,11-triaza-1(4,2), 2(2,4)-dithiazolacyclododecaphane-8-yl)but-3-en-1-yl)octanethioate (1). To a solution 10 (0.400 g, 0.800 mmol) in anhydrous CH$_2$Cl$_2$ (10 mL) at 0° C, triethylamine (0.240 mL, 1.60 mmol) was added, followed by dropwise addition of 1-octanesulfonyl chloride (0.240 mL, 1.00 mmol) over 5 min. The reaction mixture was stirred for further 15 min. Then, the reaction mixture was washed with ice-cold water, 0.01 N aqueous HCl, saturated aqueous Na$_2$CO$_3$ solution and saturated aqueous NaCl solution in turns. The organic layer was dried over Na$_2$SO$_4$ and evaporated to give as a colorless solid. The crude compound and anhydrous K$_2$CO$_3$ (0.240 g, 1.60 mmol) were added sequentially to the solution of thiooctanoic acid 10 (0.800 g, 2.40 mmol) in anhydrous acetone (2 mL). The reaction mixture was stirred at room temperature for 12 h, then was diluted with acetone (2 mL), filtered through Celite and rinse with 4 mL of acetone then concentrated in vacuo. The crude product was purified by column chromatography on silica gel to give 1 as a colorless solid (0.310 g, 64% yield) (eluted by 3% MeOH in CH$_2$Cl$_2$). $^1$H NMR (400 MHZ, CDCl$_3$) δ 7.78 (s, 1H), 6.51 (d, J=10.9 Hz, 1H), 6.49-6.40 (m, 1H), 6.26 (d, J=8.2 Hz, 1H), 5.72-5.60 (m, 1H), 5.52 (dd, J=15.5, 5.7 Hz, 1H), 5.28 (d, J=17.6 Hz, 1H), 5.01-4.92 (m, 1H), 4.54 (dd, J=3.1, 10.8 Hz, 1H), 4.32 (dd, J=3.4, 17.7 Hz, 1H), 3.89 (d, J=11.8 Hz, 1H), 3.38 (d, J=11.6 Hz, 1H), 2.89 (t, J=7.1 Hz, 2H), 2.74 (dd, J=15.4, 3.9 Hz, 1H), 2.57-2.48 (m, 3H), 2.40-2.32 (m, 2H), 2.16 (q, J=7.2, 6.8 Hz, 1H), 1.89 (s, 3H), 1.71-1.56 (m, 2H), 1.38-1.20 (m, 8H), 0.91-0.80 (m, J=6.6 Hz, 3H), 0.77 (d, J=6.9 Hz, 3H), 0.35 (d, J=6.8 Hz, 3H); $^{13}$C NMR (101 MHZ, CDCl$_3$) δ 199.7, 173.8, 170.0, 169.7, 168.7, 147.4, 130.8, 129.5, 124.3, 84.9, 58.3, 47.9, 44.3, 43.9, 41.0, 40.8, 32.4, 32.1, 31.7, 29.0, 28.9, 28.3, 25.8, 24.3, 22.7, 19.6, 15.6, 14.2; HRMS (ESI) m/z calcd for C$_{29}$H$_{43}$N$_5$NaO$_4$S$_3$ 644.2375 [M+Na]$^+$, found 644.2379; $[α]^{25}_D$: +21.2 (c=0.30, CHCl$_3$), (lit. $[α]^{25}_D$: +23.2 (c=0.25, CHCl$_3$)).

Compound 1 was also prepared from compound 10 using a similar method that employed toluenesulfonyl chloride instead of 1-octanesulfonyl chloride with 50% yield.

Compound 1 was also prepared from compound 10 under a similar method that employed methanesulfonyl chloride instead of 1-octanesulfonyl chloride with 61% yield.

(S,E)-1-((R)-4-Benzyl-2-thioxothiazolidin-3-yl)-7-((tert-butyldiphenylsilyl)oxy)-3-hydroxyhept-4-en-1-one (32). To a cooled (0° C.) solution of (R)-1-(4-benzyl-2-thioxothiazolidin-3-yl) ethanone (26) (7.90 g, 31.5 mmol) in dry CH$_2$Cl$_2$ (100 mL) was added titanium (IV) chloride (34.2 mmol, 3.60 mL) dropwise, and the solution was allowed to stir for 5 min, during which the reaction mixture turned yellow in color. DIPEA (5.90 mL, 34.2 mmol) was then added to the reaction mixture. The yellowish slurry turned dark red and was stirred for 20 min at 0° C. To this dark red solution, compound 27 (8.90 g, 26.3 mmol) in dry CH$_2$Cl$_2$ (10 mL) was added dropwise, and the reaction mixture was stirred for 1 h at 0° C. After completion of the reaction, the reaction was quenched with ammonium chloride solution and then extracted into CH$_2$Cl$_2$. The combined organic layer was dried with anhydrous Na$_2$SO$_4$ and concentrated in vacuo to yield a crude residue, which was purified by silica gel column chromatography (eluted by hexane/EtOAc, 8:2) to afford 32 (11.0 g, 71%). $^1$H NMR (400 MHZ, CDCl$_3$) δ 7.73-7.64 (m, 4H), 7.48-7.29 (m, 11H), 5.85-5.74 (m, 1H), 5.68-5.58 (m, 1H), 5.40 (ddd, J=10.7, 7.0, 4.0 Hz, 1H), 4.73-4.59 (m, 1H), 3.74 (t, J=6.6 Hz, 2H), 3.62 (dd, J=17.7, 2.9 Hz, 1H), 3.46-3.18 (m, 4H), 3.12-2.98 (m, 1H), 2.91 (d, J=11.6 Hz, 1H), 2.40-2.28 (m, 2H), 1.08 (s, 9H). $^{13}$C NMR (101 MHZ, CDCl$_3$) δ 201.3, 172.4, 136.8, 136.1, 133.7, 132.8, 131.4, 129.5, 129.1, 128.6, 128.1, 127.7, 69.3, 67.0, 63.3, 45.8, 37.4, 36.2, 34.9, 31.6, 26.8. HRMS (ESI) m/z calcd for C$_{33}$H$_{39}$NNaO$_3$S$_2$Si 612.2038 [M+Na]$^+$, found 612.2024.

2-(Trimethylsilyl)ethyl (S,E)-7-((tert-butyldiphenylsilyl)oxy)-3-hydroxyhept-4-enoate (11). To a solution of thiazoline-thione 32 (9.30 g, 15.8 mmol) was dissolved in 150 mL CH$_2$Cl$_2$ was added 2-trimethylsilylethanol (22.6 mL, 158 mmol), followed by imidazole (1.60 g, 23.6 mmol). The resulting solution was stirred overnight. The reaction mixture was concentrated in vacuo and purified by flash-column chromatography (eluted by hexanes/EtOAc, 8:1) to provide compound 11 (7.10 g, 91%) as a clear oil. $^1$H NMR (400 MHZ, CDCl$_3$) δ 7.51-7.30 (m, 10H), 5.66-5.58 (m, 1H) 5.43 (dd, J=15.3, 7.5 Hz 1H), 4.65-4.51 (m, 1H), 4.22-4.10 (m, 3H), 3.64 (t, J=6.6 Hz, 2H), 2.61 (dd, J=16.8, 6.1 Hz, 1H), 2.47 (dd, J=16.8, 8.0 Hz, 1H) 2.24-2.36 (m, 2H), 1.06 (s, 9H), 0.97-0.92 (m, 2H), 0.03 (s, 9H). $^{13}$C NMR (101 MHZ, CDCl$_3$) δ 171.9, 135.7, 133.8, 132.3, 131.8, 129.3, 127.4, 69.3, 67.0, 63.3, 46.4, 33.8, 31.5, 26.8, 19.4, −1.3.

2-(Trimethylsilyl)ethyl (S,E)-3-(((((9H-fluoren-9-yl)methoxy)carbonyl)-L-valyl)oxy)-7-((tert-butyldiphenylsilyl)oxy)hept-4-enoate (13). To a solution of compound 11 (7.00 g, 14.0 mmol) in CH$_2$Cl$_2$ (150 mL) at room temperature was added N-Fmoc-L-valine (12) (14.2 g, 42.1 mmol), EDCl-HCl (10.8 g, 56.1 mmol), DMAP (0.17 g, 1.40 mmol), and DIPEA (9.80 mL, 56.1 mmol). After stirring for 18 h, the reaction mixture was concentrated in vacuo. The crude residue was purified by flash-column chromatography (eluted by hexanes/EtOAc, 9:1) to provide compound 13 (7.34 g, 75%) as a clear oil. $^1$H NMR (400 MHZ, CDCl$_3$) δ 7.74 (d, J=7.6 Hz, 2H), 7.68-7.51 (m, 6H), 7.45-7.26 (m, 10H), 5.83 (dt, J=14.5, 6.9 Hz, 1H), 5.66 (td, J=7.7, 5.4 Hz, 1H), 5.49 (dd, J=15.5, 7.5 Hz, 1H), 5.28 (d, J=9.1 Hz, 1H), 4.49-4.05 (m, 4H), 3.65 (t, J=6.6 Hz, 2H), 2.68 (dd, J=15.8, 8.0 Hz, 1H), 2.54 (dd, J=15.7, 5.5 Hz, 1H), 2.08-2.31 (m, 3H), 1.02 (s, 9H), 0.98-0.84 (m, 5H), 0.80 (d, J=6.9 Hz, 3H), −0.01 (s, 9H). $^{13}$C NMR (101 MHZ, CDCl$_3$) δ 170.8, 169.6, 156.1, 143.9, 143.8, 141.2, 135.5, 133.7, 132.6, 129.6, 128.2, 127.6, 127.6, 127.0, 125.1, 119.9, 72.0, 66.9, 63.0, 58.7, 47.2, 39.7, 35.5, 31.3, 26.8, 19.1, 18.9, 17.2, 14.1, −1.6.

2-(Trimethylsilyl)ethyl (S,E)-3-((((R)-2-(6-(((tert-butoxycarbonyl)amino) methyl)pyridin-2-yl)-4-methyl-4,5-dihydrothiazole-4-carbonyl)-L-valyl)oxy)-7-((tert-butyldiphenylsilyl)oxy)hept-4-enoate (15). Compound 13 (1.10 g, 1.57 mmol) was dissolved in anhydrous CH$_3$CN (50 mL) and treated with Et$_2$NH (5 mL) at room temperature under argon. The resulting solution was warmed to room temperature and stirred for 2 h. The solvent was evaporated in vacuo. The resulted crude compound was then dissolved in EtOAc, concentrated in vacuo, and dried on high vacuum to remove the residual Et$_2$NH. In a separate flask, PyBOP (1.23 g, 2.36 mmol) and DIPEA (0.55 mL, 3.15 mmol) was added to a solution of pyridine thiazolene fragment[2] 14 (0.66 g, 1.89 mmol) in anhydrous CH$_2$Cl$_2$ (30 mL) under argon at room temperature. This stirred for 5 min at room temperature before being cooled down to 0° C. The amine was dissolved in anhydrous CH$_2$Cl$_2$ (15 mL) and was added dropwise to the solution of the activated acid at 0° C. under argon. The reaction mixture was stirred at room temperature for 4 h. The mixture was concentrated in vacuo and the crude residue was immediately purified via column chromatography on silica gel (eluted by hexanes/EtOAc, 7:3) to yield 15 (1.04 g, 71%). $^1$H NMR (400 MHZ, CDCl$_3$) δ 8.64-8.57 (m, 1H), 7.68-7.53 (m, 6H), 7.43-7.30 (m, 6H), 7.13 (d, J=9.0 Hz, 1H), 5.83 (dt, J=14.7, 6.8 Hz, 1H), 5.71-5.60 (m, 1H), 5.57-5.44 (m, 2H), 4.54-4.40 (m, 3H), 4.21-4.06 (m, 2H), 3.81 (d, J=11.6 Hz, 1H), 3.64 (t, J=6.7 Hz, 2H), 3.37 (dd, J=11.5, 1.9 Hz, 1H), 2.75-2.61 (m, 1H), 2.55 (dd, J=15.8, 5.5 Hz, 1H), 2.31-2.06 (m, 3H), 1.55 (s, 3H), 1.44 (s, 9H), 1.06-0.87 (m, 11H), 0.81 (d, J=7.1 Hz, 3H), 0.73 (d, J=7.1 Hz, 3H), −0.01 (d, J=1.9 Hz, 9H). $^{13}$C NMR (101 MHZ, CDCl$_3$) δ 173.9, 170.3, 169.7, 167.0, 149.8, 140.4, 135.5, 133.7, 132.6, 129.6, 128.2, 127.6, 120.3, 119.9, 85.4, 72.0, 63.1, 63.1, 56.8, 41.7, 39.8, 35.5, 31.1, 28.4, 26.8, 24.5, 19.1, 19.0, 17.3, 17.3, −1.5. HRMS (ESI) m/z calcd. for C$_{49}$H$_{71}$N$_4$O$_8$SSi$_2$ [M+H]$^+$ 931.4531, found 931.4540.

(14R,7S,10S,Z)-7-((E)-4-((Tert-butyldiphenylsilyl)oxy) but-1-en-1-yl)-10-isopropyl-14-methyl-14, 15-dihydro-8-oxa-4,11-diaza-1(2,4)-thiazola-2(2,6)-pyridinacyclododecaphane-5,9,12-trione (16). To a solution of the compound 15 (0.10 g, 0.11 mmol) in anhydrous CH$_2$Cl$_2$ (10 mL) at 0° C. was added TFA (1 mL) under argon. The mixture was stirred at room temperature for 12 h. The solvent was removed in vacuo. The resulted crude salt was then dissolved in toluene, concentrated in vacuo, and dried on high vacuum to remove residual TFA. To a solution of HATU (0.12 g, 0.32 mmol), HOBt·H$_2$O (0.03 g, 0.21 mmol) and DIPEA (0.10 mL, 0.54 mmol) in anhydrous CH$_3$CN/CH$_2$Cl$_2$ (120 mL, 1:1) at room temperature was added a solution the TFA salt in anhydrous CH$_3$CN/CH$_2$Cl$_2$ (1:1) dropwise over 10 h via a syringe pump at 0° C. After complete addition, the resulting mixture was stirred for 8 h. The solvent of the reaction mixture was evaporated in vacuo. The resulting residue was dissolved in CH$_2$Cl$_2$ (5 mL), filtered through a Celite pad and dried over anhydrous MgSO$_4$. The solvent was evaporated in vacuo, and the resulting residue was purified by column chromatography on silica gel (eluted by 3% CH$_3$OH in CH$_2$Cl$_2$) and the solution was evaporated to dryness in vacuo and to give macrocyclic core 16 (15.0 mg, 20% yield). $^1$H NMR (400 MHZ, CDCl$_3$) δ 8.69 (d, J=5.1 Hz, 1H), 7.80 (s, 1H), 7.64 (dq, J=6.4, 1.7 Hz, 4H), 7.44-7.35 (m, 6H), 6.91 (d, J=9.1 Hz, 1H), 6.11 (dd, J=8.4, 4.7 Hz, 1H), 5.93 (dtd, J=15.1, 6.9, 1.0 Hz, 1H), 5.80-5.68 (m, 1H), 5.66-5.58 (m, 1H), 5.09 (dd, J=17.6, 8.4 Hz, 1H), 4.58 (dd, J=9.1, 3.6 Hz, 1H), 4.22 (dd, J=17.6, 4.6 Hz, 1H), 4.06 (d, J=11.5 Hz, 1H), 3.76-3.66 (m, 2H), 3.38 (d, J=11.6 Hz, 1H), 3.22-3.15 (m, 2H), 2.81-2.72 (m, 1H), 2.39-2.10 (m, 3H), 1.78 (s, 3H), 1.04 (s, 9H), 0.75 (d, J=6.9 Hz, 3H), 0.65 (d, J=6.8 Hz, 3H). $^{13}$C NMR (101 MHZ, CDCl$_3$+CD$_3$OD) δ 173.9, 170.5, 170.1, 168.4, 167.3, 146.5, 135.5, 135.4, 133.8, 131.2, 129.6, 127.7, 127.6, 124.2, 84.0, 63.4, 58.1, 48.7, 43.6, 35.5, 32.2, 26.8, 24.1, 19.4, 19.1, 14.9. HRMS (ESI) m/z calcd. for C$_{39}$H$_{48}$N$_4$NaO$_5$SSi [M+Na]$^+$ 735.3012, found 735.3021.

(14R,7S,10S,Z)-7-((E)-4-Hydroxybut-1-en-1-yl)-10-isopropyl-14-methyl-14,15-dihydro-8-oxa-4,11-diaza-1(2,4)-thiazola-2(2,6)- pyridinacyclododecaphane-5,9,12-trione (17). To a solution of compound 16 (15.0 mg, 0.02 mmol) in THF (2 mL) at 0° C. was added 1 M TBAF solution (0.7 ml, 0.07 mmol) under argon. The reaction mixture was stirred for 4 h at room temperature. The reaction was quenched with aq. NH$_4$Cl and was work up with CH$_2$Cl$_2$ (3×2 mL) followed by evaporation in vacuo. The crude residue was purified over column chromatography on silica gel (eluted by 5% CH$_3$OH in CH$_2$Cl$_2$) to afford compound 17 as a viscous liquid (9.0 mg, 90% yield). $^1$H NMR (400 MHZ, CDCl$_3$) δ 8.63 (d, J=5.0 Hz, 1H), 8.42 (t, J=6.0 Hz, 1H), 7.88 (s, 1H), 7.35-7.29 (m, 1H), 7.12 (d, J=9.0 Hz, 1H), 6.00-5.72 (m, 3H), 4.86 (dd, J=17.3, 6.6 Hz, 1H), 4.53 (dd, J=9.0, 4.4 Hz, 1H), 4.41 (dd, J=17.3, 5.5 Hz, 1H), 3.98 (d, J=11.5 Hz, 1H), 3.75-3.50 (m, 2H), 3.06 (dd, J=15.6, 6.9 Hz, 1H), 2.83 (dd, J=15.6, 4.1 Hz, 1H), 2.49-2.04 (m, 4H), 1.78 (s, 3H), 0.81 (d, J=6.9 Hz, 3H), 0.73 (d, J=6.8 Hz, 3H). $^{13}$C NMR (101 MHZ, CDCl$_3$+CD$_3$OD) δ 173.5, 170.6, 169.3, 168.6, 159.6, 150.1, 140.1, 131.1, 129.0, 120.9, 117.3, 84.3, 72.5, 60.8, 58.0, 43.9, 43.3, 40.0, 35.3, 33.4, 24.6, 18.8, 17.0. HRMS (ESI) m/z calcd. For C$_{23}$H$_{30}$N$_4$NaO$_5$S [M+Na]$^+$ 497.1835, found 497.1828.

S—((E)-4-((14R,7S,10S,Z)-10-Isopropyl-14-methyl-5,9,12-trioxo-14,15-dihydro-8-oxa-4,11-diaza-1(2,4)-thiazola-2(2,6)- pyridinacyclododecaphane-7-yl)but-3-en-1-yl) octanethioate (2). (CAS Number: 1800584-53-5)4: Compound 2 was obtained using the same procedure for the preparation of compound 1, except that 17 was used instead of 10, (7.5 mg, 64% yield). $^1$H NMR (400 MHZ, CDCl$_3$) δ 8.70 (d, J=5.0 Hz, 1H), 7.81 (s, 1H), 7.39 (dd, J=5.0, 1.6 Hz, 1H), 6.92 (d, J=9.1 Hz, 1H), 6.21 (dd, J=8.4, 4.8 Hz, 1H), 5.89 (dt, J=15.4, 6.8 Hz, 1H), 5.81-5.69 (m, 1H), 5.64 (dd, J=15.5, 6.7 Hz, 1H), 5.12 (dd, J=17.6, 8.4 Hz, 1H), 4.60 (dd, J=9.1, 3.7 Hz, 1H), 4.29 (dd, J=17.6, 4.7 Hz, 1H), 4.06 (d, J=11.6 Hz, 1H), 3.39 (d, J=11.6 Hz, 1H), 3.07-2.73 (m, 4H), 2.52 (t, J=7.6 Hz, 2H), 2.41-2.26 (m, 2H), 2.26-2.07 (m, 1H), 1.82 (s, 3H), 1.72-1.54 (m, 2H), 1.40-1.10 (m, 8H), 0.97-0.84 (m, 3H), 0.76 (d, J=6.9 Hz, 3H), 0.66 (d, J=6.8 Hz, 3H). $^{13}$C NMR (101 MHZ, CDCl$_3$) δ 199.3, 173.1, 170.1, 168.5, 168.3, 159.3, 150.8, 140.1, 132.7, 128.4, 120.9, 116.9, 84.6, 72.0, 57.9, 44.4, 44.1, 43.6, 40.5, 33.7, 32.3, 31.6, 28.9, 27.9, 25.6, 24.9, 22.6, 18.9, 17.1, 14.0. HRMS (ESI) m/z calcd for $C_{31}H_{45}N_4O_5S_2$ [M+H]$^+$ 617.2826 found 617.2829; $[\alpha]^{25}{}_D$: +86.9 (c=0.6, CHCl$_3$), (lit. $[\alpha]^{25}{}_D$: +94.3 (c=0.62, CHCl$_3$)).

2-(Trimethylsilyl)ethyl (S,E)-3-((((R)-2-(2-(((tert-butoxycarbonyl)amino) methyl)oxazol-4-yl)-4-methyl-4,5-dihydrothiazole-4-carbonyl)-L-valyl)oxy)-7-((tert-butyldiphenylsilyl)oxy)hept-4-enoate (19). Compound 19 was obtained using the same procedure for the preparation of compound 15, except that 18 was used instead of 14 and with elution by 50% ethyl acetate in hexanes, (0.79 g, 71% yield). The yield is in relation to base fragment (compound 13). $^1$H NMR (400 MHZ, CDCl$_3$) δ 8.12 (s, 1H), 7.68-7.60 (m, 4H), 7.32-7.44 (m, 6H), 7.11 (d, J=9.0 Hz, 1H), 5.84 (dt, J=14.4, 6.9 Hz, 1H), 5.61-5.69 (m, 1H), 5.56-5.45 (m, 1H), 5.19 (bs, 1H), 4.43-4.52 (m, J=3H), 4.22-4.08 (m, 2H), 3.77 (d, J=11.5 Hz, 1H), 3.66 (t, J=6.6 Hz, 2H), 3.30 (d, J=11.5 Hz, 1H), 2.70 (dd, J=15.7, 7.9 Hz, 1H), 2.56 (dd, J=15.7, 5.6 Hz, 1H), 2.28 (q, J=6.8 Hz, 2H), 2.08-2.18 (m, 1H), 1.57 (s, 3H), 1.46 (s, 9H), 1.06-0.92 (m, 11H), 0.83 (d, J=6.8 Hz, 3H), 0.76 (d, J=6.8 Hz, 3H), 0.03 (s, 9H). $^{13}$C NMR (101 MHZ, CDCl$_3$) δ 174.2, 170.3, 169.6, 161.9, 160.7, 139.3, 135.5, 135.5, 133.7, 133.7, 132.4, 129.6, 128.3, 127.6, 85.2, 71.9, 63.0, 56.8, 41.2, 39.7, 35.5, 31.1, 28.3, 26.8, 24.6, 19.1, 19.0, 17.4, 17.2, −1.6. HRMS (ESI): m/z calcd for $C_{47}H_{69}N_4O_9SSi_2$ (M+H)$^+$: 921.4323, found: 921.4329.

(12Z,22Z,24R,5S,8S)-8-((E)-4-((tert-butyldiphenylsilyl)oxy)but-1-en-1-yl)-5-isopropyl-24-methyl-24,25-dihydro-7-oxa-4,11-diaza-1(4,2)-oxazola-2(2,4)-thiazolacyclododecaphane-3,6, 10-trione (20). Compound 20 was obtained using the same procedure for the preparation of compound 16, except that 19 was used instead of 15 and with elution by 5% CH$_3$OH in CH$_2$Cl$_2$, (19 mg, 25% yield). $^1$H NMR (400 MHZ, CDCl$_3$) δ 7.95 (s, 1H), 7.65-7.58 (m, 4H), 7.45-7.30 (m, 6H), 7.05 (d, J=8.9 Hz, 1H), 6.15 (dd, J=9.7, 3.8 Hz, 1H), 5.87 (dt, J=14.5, 6.9 Hz, 1H), 5.57-5.66 (m, 1H), 5.49 (dd, J=15.6, 7.2 Hz, 1H), 4.92 (dd, J=17.6, 9.7 Hz, 1H), 4.50 (dd, J=8.9, 3.4 Hz, 1H), 4.03-3.90 (m, 2H), 3.67 (t, J=6.4 Hz, 2H), 3.21 (d, J=11.4 Hz, 1H), 2.85 (dd, J=16.6, 10.3 Hz, 1H), 2.61 (dd, J=16.6, 2.9 Hz, 1H), 2.33-2.19 (m, 2H), 2.00-2.12 (m, 1H), 1.79 (s, 3H), 1.01 (s, 9H), 0.65 (d, J=6.9 Hz, 3H), 0.61 (d, J=6.9 Hz, 3H). $^{13}$C NMR (101 MHZ, CDCl$_3$) δ 173.5, 170.7, 168.7, 163.3, 161.9, 141.2, 135.5, 135.0, 133.8, 133.8, 132.3, 129.6, 128.4, 127.7, 83.8, 72.2, 63.0, 58.1, 50.8, 43.3, 40.3, 37.2, 35.6, 34.2, 26.8, 26.8, 23.8, 23.5, 20.2, 19.2, 18.7, 17.2. HRMS (ESI): m/z calcd for $C_{37}H_{46}N_4NaO_5SSi$ (M+Na)$^+$: 725.2805, found: 725.2810.

(12Z,22Z,24R,5S,8S)-8-((E)-4-hydroxybut-1-en-1-yl)-5-isopropyl-24-methyl-24,25-dihydro-7-oxa-4,11-diaza-1(4,2)-oxazola-2(2,4)-thiazolacyclododecaphane-3,6,10-trione (21). Compound 21 was obtained using the same procedure for the preparation of compound 17, except that 20 was used instead of 16 and with elution by 5% CH$_3$OH in CH$_2$Cl$_2$, (8.8 mg, 89% yield). $^1$H NMR (400 MHZ, CDCl$_3$) δ 7.97 (s, 1H), 7.54-7.46 (m, 1H), 7.06 (d, J=8.9 Hz, 1H), 5.85-5.76 (m, 1H), 5.69-5.54 (m, 2H), 4.82-4.65 (m, 1H), 4.56-4.34 (m, 1H), 4.10-3.85 (m, 2H), 3.72-3.46 (m, 2H), 3.24-3.18 (m, 1H), 2.98-2.74 (m, 2H), 2.60 (dd, J=15.8, 3.4 Hz, 1H), 2.25 (q, J=6.3 Hz, 2H), 2.06-1.91 (m, 1H), 1.77 (s, 3H), 0.66 (d, J=6.3 Hz, 3H), 0.61 (d, J=6.3 Hz, 3H). $^{13}$C NMR (101 MHZ, CDCl$_3$) δ 173.4, 173.4, 170.7, 168.7, 163.7, 141.3, 134.6, 131.4, 129.2, 83.3, 72.0, 60.9, 58.5, 42.9, 40.4, 37.2, 35.4, 33.8, 23.7, 18.6, 17.3. HRMS (ESI): m/z calcd for $C_{21}H_{28}N_4NaO_5S$ (M+Na)$^{30}$: 487.1627, found: 487.1623.

S—((E)-4-((12Z,22Z,24R,5S,8S)-5-isopropyl-24-methyl-3,6, 10-trioxo-24,25-dihydro-7-oxa-4, 11-diaza-1(4,2)-oxazola-2(2,4)- thiazolacyclododecaphane-8-yl)but-3-en-1-yl) octanethioate (3). (CAS Number: 1800584-53-5)[4]: Compound 3 was obtained using the same procedure for the preparation of compound 1, except that 21 was used instead of 10 and with elution by 5% CH$_3$OH in CH$_2$Cl$_2$ (6.3 mg, 60% yield). (eluted by 3% CH$_3$OH in CH$_2$Cl$_2$). $^1$H NMR (400 MHZ, CDCl$_3$) 7.99 (s, 1H), 7.09 (d, J=9.0 Hz, 1H), 6.13 (dd, J=4.2, 8.6 Hz, 1H), 5.88-5.78 (m, 1H), 5.68-5.60 (m, 1H), 5.58-5.50 (m, 1H), 4.99 (dd, J=9.8, 17.6 Hz, 1H,), 4.55 (dd, J=3.5, 10.7 Hz, 1H), 4.10-3.97 (m, 2H), 3.25 (d, J=11.5 Hz, 1H), 2.95-2.83 (m, 3H), 2.69 (dd, J=2.9, 16.4 Hz, 1H), 2.53 (t, J=7.7 Hz, 2H), 2.32 (q, 2H), 2.17-2.03 (m, 1H), 1.85 (s, 3H), 1.72-1.57 (m, 2H), 1.38-1.18 (m, 8H), 0.88 (t, J=6.6 Hz, 3H), 0.69 (d, J=6.9 Hz, 3H), 0.65 (d, J=6.9 Hz, 3H). $^{13}$C NMR (101 MHZ, CDCl$_3$) δ 199.3, 173.4, 170.5, 168.7, 163.2, 161.8, 141.1, 135.0, 132.7, 128.4, 83.8, 71.9, 58.1, 44.1, 43.3, 40.3, 37.3, 34.2, 32.2, 31.6, 28.9, 27.9, 25.6, 23.8, 22.6, 18.7, 17.2, 14.1. HRMS (ESI): m/z calcd for $C_{29}H_{43}N_4O_6S_2$ (M+H)$^+$: 607.2624, found: 607.2632. $[\alpha]^{25}{}_D$: +19.9 (c=0.7, CH$_2$Cl$_2$), (lit. $[\alpha]^{25}{}_D$: +18 (c=0.7, CH$_2$Cl$_2$)).

REFERENCES

Each of the following references, or any other reference disclosed elsewhere herein, is hereby incorporated by reference in its entirety for all purposes.

1. Bowers, A. A.; Greshock, T. J.; West, N.; Estiu, G.; Schreiber, S. L.; Wiest, O.; Williams, R. M.; Bradner, J. E., *J. Am. Chem. Soc.*, 2009, 131, 2900-2905.
2. Seiser, T.; Kamena, F.; Cramer, N., *Angew. Chem., Int. Ed.* 2008, 47, 6483-6485.
3. Chen, Q.-Y.; Chaturvedi, P. R.; Luesch, H. *Org. Process, Res. & Dev.*, 2018, 22, 190-199.
4. Clausen, D. J.; Smith, W. B.; Haines, B. E.; Wiest, O.; Bradner, J. E.; Williams, R. M., *Bioorg. & Med. Chem.*, 2015, 23, 5061-5074.
5. Guerra-Bubb, J. M.; Bowers, A. A.; Smith, W. B.; Paranal, R.; Estiu, G.; Wiest, O.; Bradner, J. E.; Williams, R. M., *Bioorg. & Med. Chem. Lett.*, 2013, 23, 6025-6028.
6. Zhang, B.; Liu, J.; Gao, D.; Yu, X.; Wang, J.; Lei, X., *Eur. J. Med. Chem.*, 2019, 182, 111672.
7. Akoto, D. O.; Rainier, J. D., *Synthesis* 2019; 51, 3529-3535

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred aspects, exemplary aspects and optional features, modification and variation of the concepts herein disclosed may be resorted to by those skilled in the art, and that such modifications and variations are considered to be within the scope of this invention as defined by the appended claims. The specific aspects provided herein are examples of useful aspects of the present invention and it will be apparent to one skilled in the art that the present invention may be carried out using a large number of variations of the devices, device components, methods steps set forth in the present description. As will be obvious to one of skill in the art, methods, and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomer and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups groups from which a proton can be removed (e.g., —COOH) or added (e.g., amines) or which can be quaternized (e.g., amines). All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, a carbon atom range, or a composition or concentration range, all intermediate ranges, and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific aspects that are in the prior art. For example, when composition of matter is claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred aspects and optional features, modification and variation of the concepts herein disclosed may be resorted to by those skilled in the art, and that such modifications and variations are considered to be within the scope of this invention as defined by the appended claims.

We claim:

1. A method for preparing a compound of formula (III):

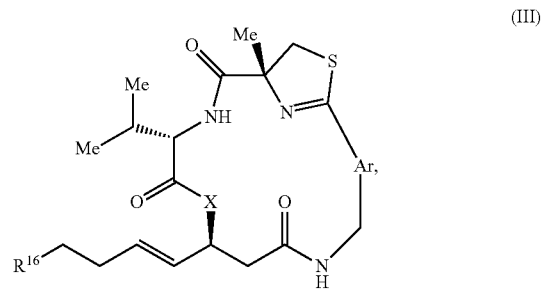

the method comprising:
reacting a compound of formula (I):

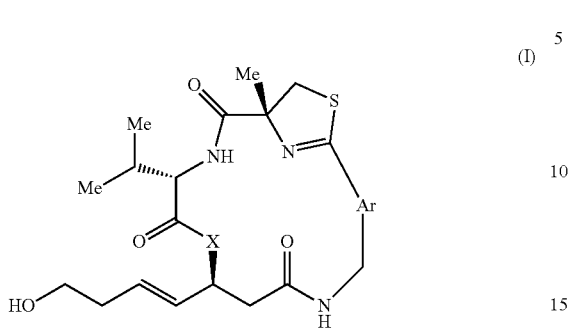

with an activating agent selected from $C_1$-$C_{20}$ linear or branched alkyl-sulfonyl halide, substituted alkyl-sulfonyl halide, arylsulfonyl halide, substituted arylsulfonyl halide, halo-phosphite, or a halogenating reagent, thereby forming a compound of formula (II):

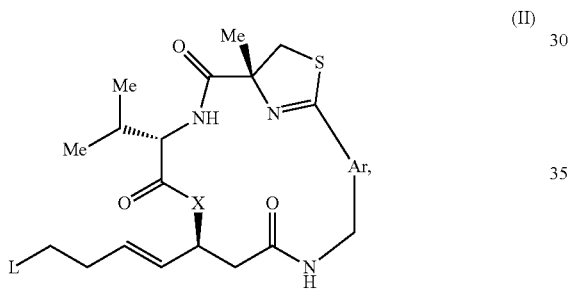

and reacting the compound of formula (II) with a nucleophile comprising an $R^1$ group, thereby forming the compound of formula (III);

wherein:

X is O or NH;

Ar is thiazolyl, pyridinyl, or oxazolyl;

$R^1$ is $R^2COS$, $R^3S$, or $R^4R^5N$;

$R^2$, $R^3$, $R^4$, and $R^5$ independently are hydrogen, $C_1$-$C_{24}$ linear alkyl, $C_1$-$C_{24}$ linear alkyl substituted with one or more aryl or heteroaryl in any position, $C_1$-$C_{24}$ branched alkyl, $C_1$-$C_{24}$ branched alkyl substituted with one or more aryl or heteroaryl in any position, $C_3$-$C_{24}$ cyclic alkyl, $C_3$-$C_{24}$ cyclic alkyl substituted with one or more aryl or heteroaryl in any position, $C_2$-$C_{24}$ alkenyl, $C_2$-$C_{24}$ alkynyl, aryl, heteroaryl, diphenyl methyl, or triphenylmethyl; and L is a leaving group selected from $C_1$-$C_{24}$ linear or branched carbon sulfonate, substituted $C_1$-$C_{24}$ linear or branched sulfonate, arylsulfonate, substituted arylsulfonate, heteroarylsulfonate, substituted heteroarylsulfonate, phosphate, or halogen.

2. A method for preparing a compound of formula (III):

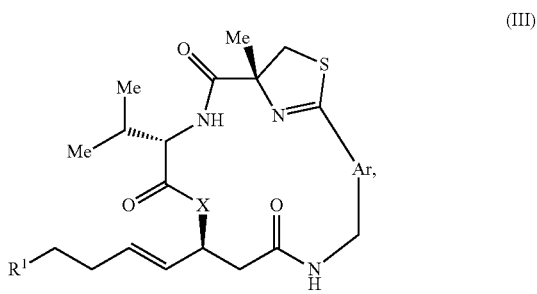

the method comprising:
reacting a compound of formula (II) with a nucleophile comprising an $R^1$ group:

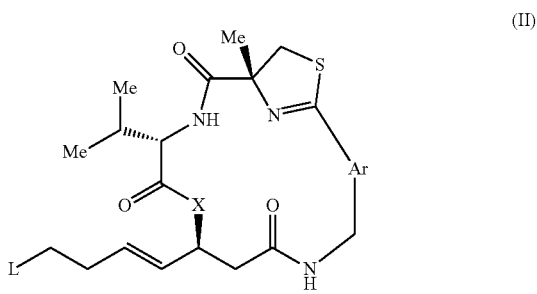

wherein:

X is O or NH;

Ar is thiazolyl, pyridinyl, or oxazolyl;

$R^1$ is $R^2COS$, $R^3S$, or $R^4R^5N$;

$R^2$, $R^3$, $R^4$, and $R^5$ independently are hydrogen, $C_1$-$C_{24}$ linear alkyl, $C_1$-$C_{24}$ linear alkyl substituted with one or more aryl or heteroaryl in any position, $C_1$-$C_{24}$ branched alkyl, $C_1$-$C_{24}$ branched alkyl substituted with one or more aryl or heteroaryl in any position, $C_3$-$C_{24}$ cyclic alkyl, $C_3$-$C_{24}$ cyclic alkyl substituted with one or more aryl or heteroaryl in any position, $C_2$-$C_{24}$ alkenyl, $C_2$-$C_{24}$ alkynyl, aryl, heteroaryl, diphenyl methyl, triphenylmethyl; and L is a leaving group selected from $C_1$-$C_{24}$ linear or branched carbon sulfonate, substituted $C_1$-$C_{24}$ linear or branched sulfonate, arylsulfonate, substituted arylsulfonate, heteroarylsulfonate, substituted heteroarylsulfonate, phosphate, or halogen; and producing the compound of formula (II) from a compound of formula (IX):

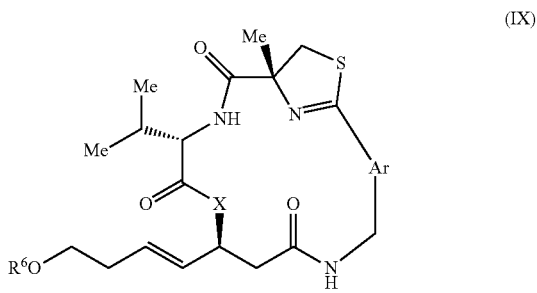

by converting OR$^6$ of the compound of formula (IX) into the leaving group L;
wherein R$^6$ is H or a suitable alcohol protecting group.

3. The method of claim 2, wherein converting OR$^6$ into the leaving group L comprises:
when R$^6$ is the suitable alcohol protecting group, deprotecting the suitable alcohol protecting group to provide the compound of formula (IX) where R$^6$ is H; and
reacting the compound of formula (IX) where R$^6$ is H with an activating agent selected from C$_1$-C$_{20}$ linear or branched alkyl-sulfonyl halide, substituted alkyl-sulfonyl halide, arylsulfonyl halide, substituted arylsulfonyl halide, halo-phosphite, or a halogenating reagent.

4. The method of claim 2, wherein the compound of formula (IX) is a compound of formula (I):

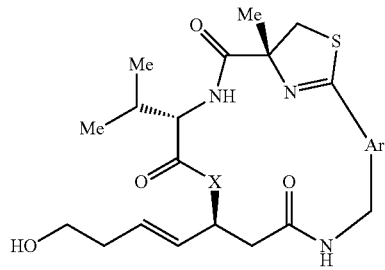
(I)

and the method comprises reacting the compound of formula (I) with an activating agent selected from C$_1$-C$_{20}$ linear or branched alkyl-sulfonyl halide, substituted alkyl-sulfonyl halide, arylsulfonyl halide, substituted arylsulfonyl halide, halo-phosphite, or a halogenating reagent, thereby forming the compound of formula (II).

5. The method of claim 2, wherein the compound of formula (IX) is a compound of formula (I-a), (I-b), or (I-c):

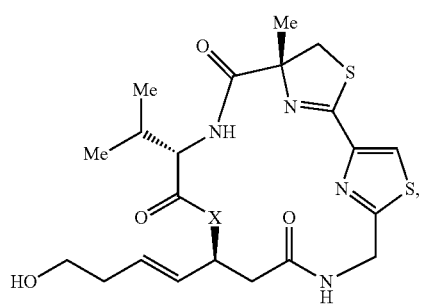
(I-a)

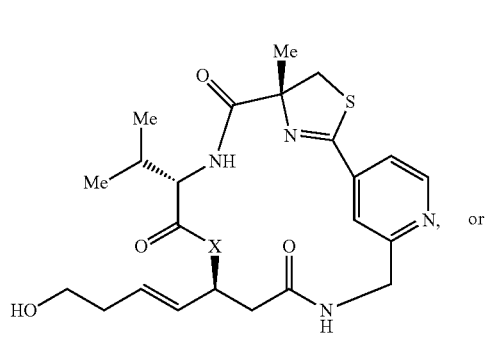
(I-b)

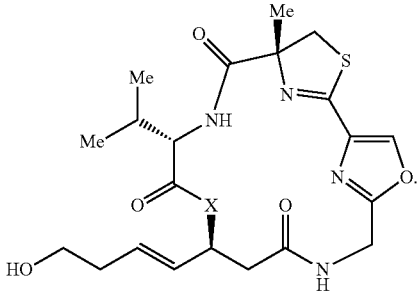
(I-c)

6. The method of claim 1, wherein L is OMs, OTs, OTf, 2,2,2-trifluoroethanesulfonate, n-octanesulfonate, benzenesulfonate, OP(=O)(OMe)$_2$, OP(=O)(OEt)$_2$, OP(=O)(OPh)$_2$, I, Br, Cl or F.

7. The method of claim 1, wherein Ar is:

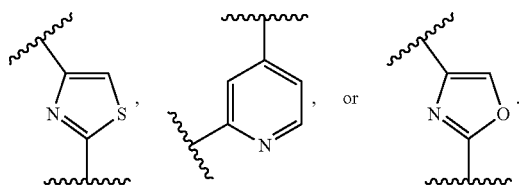 [SMILES: *c1csc(*)n1 ; *c1ccnc(*)c1 ; *c1coc(*)n1]

8. The method of claim 1, wherein the nucleophile is thiooctanoic acid, such that the compound of formula (III) is a compound of formula (XXV):

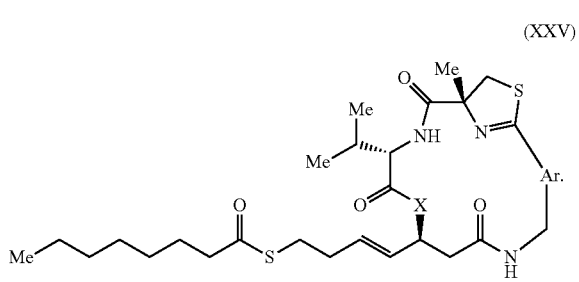
(XXV)

9. The method of claim 8, wherein:
X is NH and Ar is:

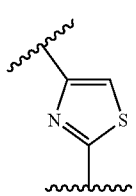 [SMILES: *c1csc(*)n1]

such that the compound of formula (III) is a compound of formula (1):

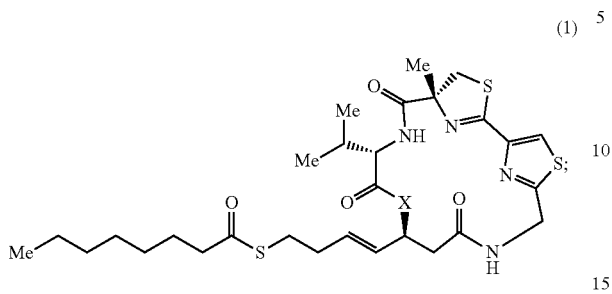

X is O and Ar is:

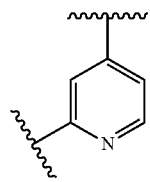 [SMILES: *c1ccnc(*)c1]

such that the compound of formula (III) is a compound of formula (2):

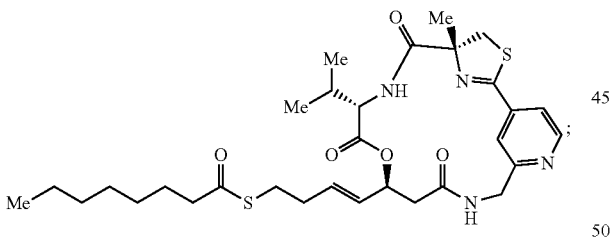

or
X is O and Ar is:

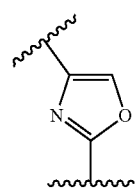

such that the compound of formula (III) is a compound of formula (3):

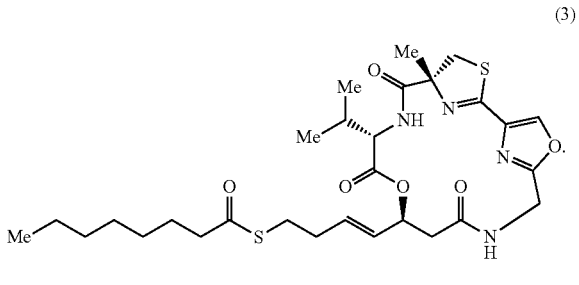 [SMILES: CCCCCCCC(=O)SCC/C=C/[C@@H]1CC(=O)NCc2nc(co2)C2=N[C@@](C)(CS2)C(=O)N[C@@H](C(C)C)C(=O)O1]

10. The method of claim 2, wherein the method further comprises producing a compound of formula (I) or the compound of formula (IX) from one or more reactions comprising:

a compound of formula (IV):

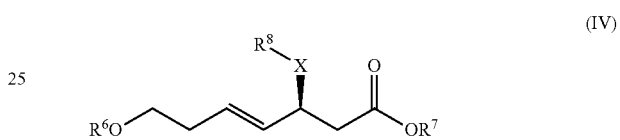

a compound of formula (V):

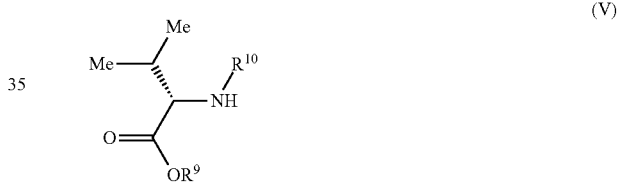

and a compound of formula (VI):

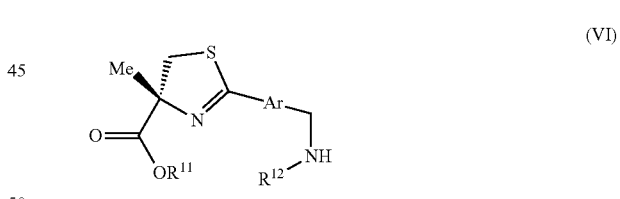

wherein:
$R^6$ is H or a suitable alcohol protecting group,
$R^8$, $R^{10}$, and $R^{12}$ independently are H, a suitable amine protecting group, or a chiral group,
$R^7$, $R^9$, and $R^{11}$ independently are H, an alkali metal ion, an alkaline earth metal ion, or a suitable carboxylic acid protecting group;
optionally wherein the suitable carboxylic acid protecting group is selected from $C_1$-$C_6$ linear or branched alkyl, $C_1$-$C_6$ linear or branched alkyl substituted with one or more aryl or heteroaryl in any position, or alkylsilyl;
optionally wherein the $C_1$-$C_6$ linear or branched alkyl, or the $C_1$-$C_6$ linear or branched alkyl substituted with one or more aryl or heteroaryl in any position, is selected from methyl, ethyl, propyl, isopropyl, allyl, butyl, 2-butyl, tert-butyl, benzyl, or substituted benzyl; and
optionally wherein the alkylsilyl is 2-(trimethylsilyl)ethyl.

11. The method of claim 10, wherein:
the compound of formula (IV) is reacted with the compound of formula (V) via condensation to form a compound of formula (VII):

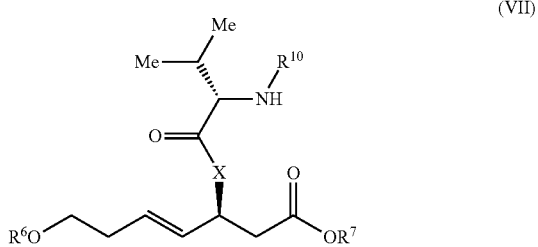
(VII)

the compound of formula (VII) is reacted with the compound of formula (VI) via amidation to form a compound of formula (VIII):

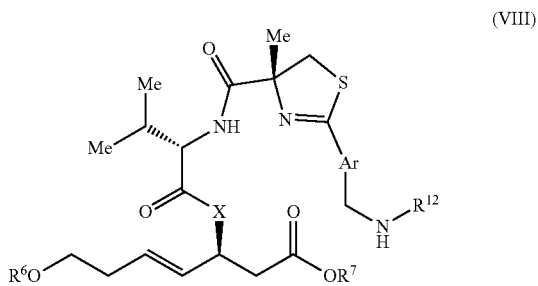
(VIII)

and the compound of formula (VIII) is reacted by amidating ring closure to form the compound of formula (IX) or a compound of formula (I)

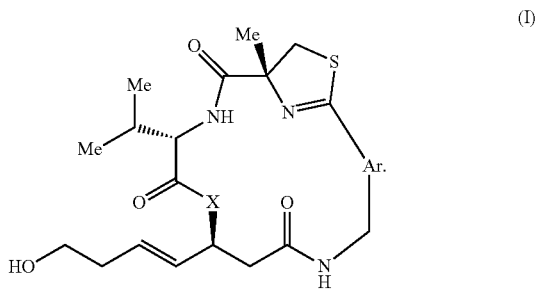
(I)

12. The method of claim 11, wherein:
$R^6$ is H or a suitable alcohol protecting group;
in reacting the compound of formula (IV) with the compound of formula (V): $R^8$ is H, and when X is N, the N is neutral or positively charged; $R^7$ is a suitable carboxylic acid protecting group; $R^{10}$ is a suitable amine protecting group; and $R^9$ is H, an alkali metal ion, or an alkaline earth metal ion;
in reacting the compound of formula (VI) with the compound of formula (VII): $R^7$ is a suitable carboxylic acid protecting group; $R^{10}$ is H, and optionally $R^{10}$ is attached to a positively charged nitrogen atom; $R^{11}$ is H, an alkali metal ion, or an alkaline earth metal ion; and $R^{12}$ is a suitable amine protecting group; and
in reacting the compound of formula (VIII) by amidating ring closure: $R^6$ is H or a suitable alcohol protecting group; $R^7$ is H, an alkali metal ion, or an alkaline earth metal ion; and $R^{12}$ is H, and optionally $R^{12}$ is attached to a positively charged nitrogen atom.

13. The method of claim 10, wherein X is NH, and the method further comprises producing the compound of formula (IV) by:
reacting via imine formation a compound of formula (X):

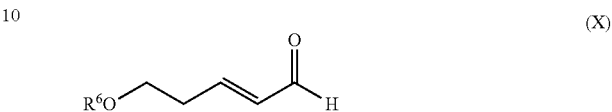
(X)

with a chiral auxiliary of formula (XI-a):

(XI-a)

to form a compound of formula (XII):

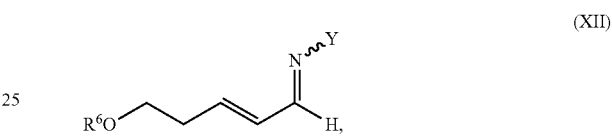
(XII)

reacting the compound of formula (XII) via nucleophilic addition with a compound of formula (XIII):

(XIII)

to form the compound of formula (IV) where X is NH and $R^8$ is chiral group Y:

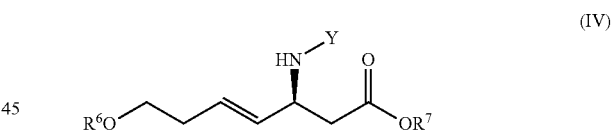
(IV)

and cleaving the N—Y bond to form the compound of formula (IV) where $R^8$ is H, and when X is N, the N is neutral or positively charged,
wherein:
Y is a chiral group sufficient to effect a diastereoselective nucleophilic addition of the compound of formula (XIII) to the compound formula (XII) to form the compound of formula (IV) as a majority product where $R^8$ is chiral group Y,
$R^6$ is a suitable alcohol protecting group,
$R^7$ is a suitable carboxylic acid protecting group;
optionally wherein the carboxylic acid protecting group is selected from $C_1$-$C_6$ linear or branched alkyl, $C_1$-$C_6$ linear or branched alkyl substituted with one or more aryl or heteroaryl in any position, or alkylsilyl;
optionally wherein the $C_1$-$C_6$ linear or branched alkyl, or the $C_1$-$C_6$ linear or branched alkyl substituted with one or more aryl or heteroaryl in any position, is selected from methyl, ethyl, propyl, isopropyl, allyl, butyl, 2-butyl, tert-butyl, benzyl, or substituted benzyl; and optionally wherein the alkylsilyl is 2-(trimethylsilyl)ethyl; and
$R^{13}$ is H, a halide, or a metal comprising Li, Na, K, ZnBr, ZnCl, CuCl, CuBr, CuI, Cu, or any combination thereof.
14. The method of claim 13, wherein Y is $R^{14}$—S=O such that the chiral auxiliary is of formula (XI-b):
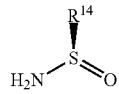
(XI-b)
wherein $R^{14}$ is tert-butyl such that the compound of formula (XI-b) is (R)-tert-butanesulfinamide.
* * * * *

UNITED STATES PATENT AND TRADEMARK OFFICE
CERTIFICATE OF CORRECTION

PATENT NO. : 12,227,522 B2
APPLICATION NO. : 18/255969
DATED : February 18, 2025
INVENTOR(S) : Robert M. Williams et al.

Page 1 of 1

It is certified that error appears in the above-identified patent and that said Letters Patent is hereby corrected as shown below:

In the Claims

In Claim 1, Column 48, Line 55-65, please delete the structure:

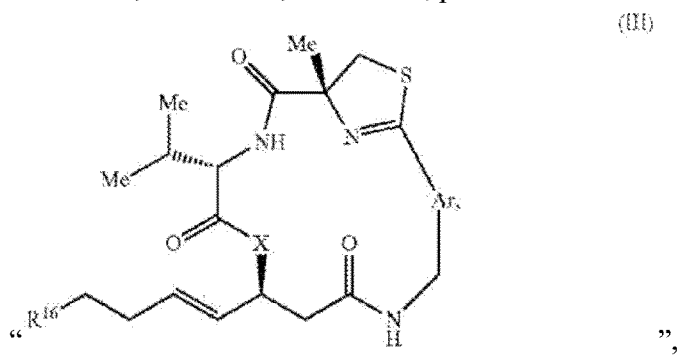

",

And replace with the following structure:

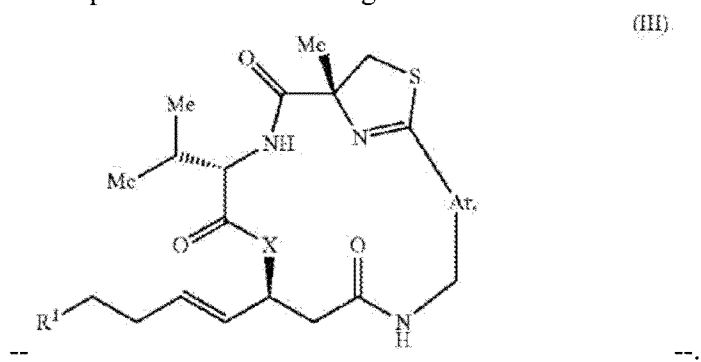

--.

Signed and Sealed this
Twenty-sixth Day of August, 2025

Coke Morgan Stewart
*Acting Director of the United States Patent and Trademark Office*